(12) United States Patent
Bertelsen et al.

(10) Patent No.: US 6,761,904 B2
(45) Date of Patent: Jul. 13, 2004

(54) PHARMACEUTICAL KIT COMPRISING MIDODRINE AS ACTIVE DRUG SUBSTANCE

(75) Inventors: Poul Bertelsen, Vanløse (DK); Annette Skinhøj, Rødovre (DK); Peder Mohr Olsen, Kirke Hyllinge (DK)

(73) Assignee: Nycomed Austria GmbH, Linz (AT)

( * ) Notice: Subject to any disclaimer, the term of this patent is extended or adjusted under 35 U.S.C. 154(b) by 0 days.

(21) Appl. No.: 09/823,093

(22) Filed: Mar. 29, 2001

(65) Prior Publication Data

US 2002/0193445 A1 Dec. 19, 2002

Related U.S. Application Data

(60) Provisional application No. 60/203,783, filed on May 12, 2000.

(30) Foreign Application Priority Data

May 31, 2000 (DK) ........................................ 2000 00549
May 26, 2000 (DK) ........................................ 2000 00841

(51) Int. Cl.[7] .............................. A61K 9/20; A61K 9/50; A61K 31/165
(52) U.S. Cl. ........................ 424/464; 424/465; 424/468
(58) Field of Search ................................ 424/464, 465, 424/468

(56) References Cited

U.S. PATENT DOCUMENTS

| 5,128,144 A | * | 7/1992 | Korsatko-Wabnegg et al. | .. 424/464 |
| 5,183,666 A | | 2/1993 | Korsatko-Wabnegg et al. | .. 424/464 |

FOREIGN PATENT DOCUMENTS

| AT | 383 270 | 5/1984 | ............ A61K/9/26 |
| AT | 383 270 B | 5/1984 | ............ A61K/9/26 |
| DE | 393536 A1 | 5/1991 | ............ A61K/9/22 |
| EP | 0 164 571 | 5/1985 | ............ A61K/9/22 |
| EP | A 0 164 571 | 12/1985 | ............ A61K/9/22 |

OTHER PUBLICATIONS

Derwent Abstract of EP 0 164 571, Issued Dec. 19, 1985.
Korsatko–Wabnegg,B. "Entwicklung von Manteltabletten mit 'Controlled–Release'–Effekt auf der Basis von Poly–D(–)–3–hydroxybuttersaure", Pharmazie 45 (1990): pp. 842–844.
Korsato–Wabnegg, B., et al. "Uber den Einsatz von Ploy–D(–)–3–Hydroxybuttersaure zur Formuloierung von Manteltabletten mit 'Delayed–Release'–Effeky" Pharmazie 46 (1991): pp. 204–206.
Derwent abstract of DE 3935736A, Issued May 2, 1991.

* cited by examiner

*Primary Examiner*—Thurman K. Page
*Assistant Examiner*—Rachel M. Bennett
(74) *Attorney, Agent, or Firm*—David G. Conlin; Peter F. Corless; Dianne M. Rees

(57) ABSTRACT

The invention provides a novel pharmaceutical kit comprising a controlled release pharmaceutical compositions for oral use containing midodrine and/or its active metabolite desglymidodrine. The controlled release composition is designed to release midodrine and/or desglymidodrine after oral intake in a manner which enables absorption to take place in the gastrointestinal tract so that a relatively fast peak plasma concentration of the active metabolite desglymidodrine is obtained, followed by a prolonged and relatively constant plasma concentration of desglymidodrine. The invention also provides a method for treating orthostatic hypotension and/or urinary incontinence, the method comprising administration to a patient in need thereof of an effective amount of midodrine and/or desglymidodrine in a kit.

104 Claims, 24 Drawing Sheets

PHARMACEUTICAL KIT COMPRISING MIDODRINE AS ACTIVE DRUG SUBSTANCE

This application claims priority to U.S. Provisional Application No. 60/203,783, filed May 12, 2000 and is incorporated herein by reference.

The present Invention relates to a method for treating mammals (such as, e.g., humans) in need thereof with a novel controlled release pharmaceutical composition for oral use containing midodrine and/or its active metabolite desglymidodrine together with a relatively fast onset composition of midodrine and/or its active metabolite desglymidodrine. The present invention also relates to a kit comprising a controlled release composition, e.g. intended for administration once or twice daily, together with one or more relatively fast onset compositions for supplemental and individual administration.

The invention also relates to a pharmaceutical composition comprising comprising midodrine (ST 1085) or a pharmaceutically acceptable salt thereof and/or its active metabolite desglymidodrine (ST 1059) or a pharmaceutically acceptable salt thereof, the composition being adapted to provide midodrine and/or desglymidodrine in such a manner that a relatively fast therapeutically effective concentration of desglymidodrine is obtained after administration of the composition.

The novel controlled release compositions are designed to release midodrine and/or desglymidodrine after oral intake in a manner which enables absorption to take place in the gastrointestinal tract so that a relatively fast peak plasma concentration of the active metabolite desglymidodrine is obtained followed by a prolonged and relatively constant plasma concentration of desglymidodrine. However, the patient may due to individual needs or because of activities during the day experience situations where an increase in the plasma concentration is needed for an optimal treatment regimen. Therefore, the patient may on an individual basis supply the controlled release composition with one or more administrations of a quick release composition or another composition providing a relatively fast onset.

The indications of midodrine include symptomatic orthostatic hypotension, orthostatic intolerance, symptomatic hypotension (e.g. hypotension associated with infections, the convalescent period, surgical operations, delivery, changes in the weather as well as what is called "difficulties in getting started in the mornings"), as well as in the control of hypotensive side effects of hypnotics and psychotropics. Futhermore, midodrine is expected to be effective in the treatment of urinary incontinence. Many of these indications call for a very individual treatment regimen where a basic "all day" treatment supplied with one or more fast onset formulations are very beneficial.

In another aspect, the invention relates to a method for treating hypotension and/or urinary incontinence, the method comprising administration to a patient in need thereof of an effective amount of midodrine and/or desglymidodrine in a controlled release composition according to the invention together with one or more fast onset compositions comprising an effective amount of midodrine and/or desglymidodrine.

One of the advantages of the invention is that the controlled release composition provides a base line plasma concentration, which during most of the day is therapeutically effective. When a higher concentration is needed, only a minor supply of active drug substance is necessary to obtain a very fast relief from symptoms. If the constant base line plasma concentration was absent, it would be necessary to use a relative higher fast onset dose to reach the high therapeutically effective level. The high therapeutically effective level may be due to individual circumstances in the patient or may be a consequence of physical routines and/or the nature of the underlying disease. The situations and symptoms are often well recognized and experienced by the patient himself. The kit according to the present invention is a superior tool for obtaining an optimal treatment with a minimum of active drug substance.

The novel compositions are also designed for administration once or twice daily, preferably once daily, i.e. a therapeutically effective concentration of desglymidodrine is maintained for a period of at least 10–16 hours followed by a wash out period of about 8–12 hours in order to avoid the well-known midodrine related side effect with respect to supine hypertension. In the present context a therapeutically effective concentration of desglymidodrine is defined as a plasma concentration of desglymidodrine of at least about 3 ng/ml such as, e.g. at least about 3.2 ng/ml, at least about 3.5 ng/ml, at least about 3.7 ng/ml, at least about 4.0 ng/ml, at least about 4.2 ng/ml, at least about 4.5 ng/ml, at least about 4.7 ng/ml or at least about 5 ng/ml.

BACKGROUND OF THE INVENTION

Controlled release midodrine compositions are known from the prior art, e.g. U.S. Pat. No. 5,128,144 (Korsatko-Waabnegg et al.), EP-B-0 164 571 (CL Pharma Aktiengesellschaft) and AT-8-B-383 270 (Chemie Linz Aktiengesellschaft). However, in none of these documents are any compositions intended for less frequent administration such as, e.g., once or twice daily and furthermore, there is no indication of absorption of midodrine (or its active metabolite) from the colon.

DISCLOSURE OF THE INVENTION

Midodrine is a prodrug, which is activated within the human body by an enzymatic hydrolysis to release the therapeutically active metabolite desglymidodrine. Desglymidodrine acts by a stimulation of $\alpha_1$ receptors. Midodrine is used in the treatment of symptomatic orthostatic hypotension. Disorders causing orthostatic hypotension are Generalized Primary Autonomic Failure
    Pure autonomic failure or idiopathic orthostatic hypotension (Bradbury-Eggleston syndrome)
    Pure autonomic failure with multiple-system atrophy or Shy-Drager syndrome
    Acute pandysautonomia (panautonomic neuropathy)
    Familial dysautonomia (Riley-Day syndrome)
Partial Primary Autonomic Failure
    Dopamine E-hydroxylase deficiency
    Postural orthostatic tachycardia syndrome (length-dependent autonomic neuropathy)
    Monoamine oxidase deficiency
    Pure vasomotor failure
Disorders of Idiopathic Orthostatic Intolerance
    Postural orthostatic tachycardia syndrome
    Mitral valve prolapse
    Due to prolonged bed rest or space flight
    Due to asthenic habitus
Disorders of the Central Nervous System
    Tumors (hypothalamic, parasellar, posterior fossa)
    Multiple cerebral infarcts
    Wernicke's encephalopathy Tabes dorsalis
Traumatic and inflammatory myelopathies
Parkinson's disease
Hereditary system degenerations
Syringomyelia
Dysautonomia of advanced age
Multiple sclerosis
Systemic Diseases with Autonomic Neuropathy
  Botulism
  Diabetic neuropathy
  Primary systemic amyloidosis
  Guillain-Barrésyndrome
  Porphyria
  Lambert-Eaton myasthenic syndrome
  Paraneoplastic autonomic neuropathy
  Uremic neuropathy
  Connective tissue disease
  Tangier and Fabry's diseases
  Vincristine and heavy metal neuropathies
  Leprosy
  $B_{12}$ deficiency
  4 Chronic Chagas' disease
  Propafenone neuropathy (16)
Endorcine-metabolic Disorders
  Primary and secondary adrenocortical insufficiency
  Pheochromocytoma
  Marked potassium depletion
  Severe hypoaldosteronism
Latrogenic Causes
  Antihypertensive drugs (Δ-methyldopa, guanethidine, prazosin, E blockers)
  Psychotropic drugs (phenothiazines, butyrophenones)
  Antiparkinsonian drugs (Sinemet, Parlodel)
  Vasodilator drugs (nitrates)
  Certain illicit drugs (marijuana)
  Thoracolumbar sympathectomy
Disorders with Diminished Cardiac Output
  Reduced intravascular volume
  Acute and chronic blood loss
  Fluid loss due to vomiting, diarrhea, diuretics
  Gastrectomy with the dumping syndrome
  Salt-losing nephropathy
  Altered capillary permeability
  Impaired venous return
  Severe varicose veins
  Venous obstruction (late pregnancy)
  Reflex and pharmacologic vasodilatation
  Muscle wasting and prolonged recumbency
  Intrinsic cardiac disease
  Myocardial infarct
  Arrhythmias
  Restrictive pericardial/myocardial diseases
Miscellaneous Causes
  Hyperbradykinnism
  Chronic renal hemodialysis
  Anorexia nervosa
  Reduced aortic compliance
  Mastocytosis
  Baroreflex failure.

Furthermore, midodrine may be used in disorders retrograde ejaculation; disorder of semen ejaculation, or to attenuate symptoms of chronic orthostatic hypotension due to autonomic failure in patients with Bradbury-Eggleston, Shy-Drager syndromes, diabetes mellitus disease and Parkinson's disease.

Midodrine is approved in a variety of European and overseas countries including the U.S.A. mainly for the treatment of symptomatic orthostatic hypotension. FDA has recommended a dosing of midodrine of up to 10 mg 3 times daily for the treatment of hypotension. According to FDA, the latest dose must not be given later than 6 pm for safety reasons in order to avoid or reduce the risk of supine hypertension. Other countries recommend that the latest dose must not be given later than 4 hours before bedtime.

Midodrine for use in stress urinary incontinence is a very promising use with a tremendous market potential also due to the ageing population. Current conservative therapeutic approaches are α-sympathomimetics, pelvic floor exercises and estrogens, or surgery, which are rather complementary than competitive.

Due to the rather short half-life of the active metabolite of approximately 3 hours midodrine normally must be administered 2–4 times daily. Considering the chronic nature of the diseases in question, which requires a long term treatment as well as the correlation between plasma levels and the incidence and severity of adverse events, the development of a controlled release form is highly desired.

It has now been found that absorption takes place through the whole gastrointestinal tract, Thus, it has been found that when midodrine reaches the colon (about 8 hours after intake of a single unit capsule containing midodrine) the prodrug midodrine is not measured in plasma at least not at a therapeutic level while the extent of absorption of the active metabolite is identical to that of a solution. In other words, with respect to absorption from the colon it has been found that it is not midodrine, which is measured after oral intake of midodrine but instead it is the active metabolite desglymidodrine itself.

After colon absorption a maximum plasma concentration of desglymidodrine is found to take place at approximately 3 hours after application, i.e. $t_{max}$ corresponds to approx. 3 hours. In contrast thereto, a $t_{max}$ of about 1–2 hour for desglymidodrine is observed after oral intake of midodrine and the corresponding value for midodrine itself is a $t_{max}$ of about 30 min.

The finding that midodrine is converted to the active metabolite before or during absorption from the colon is of importance with respect to the present invention. A further important issue is the fact that FDA has recommended that the latest dose of midodrine is taken not later than 6 pm for safety reasons, thus a wash out period through the night is desirable.

Based on the above findings and the therapeutic needs, the present inventors have developed a kit containing at least two different parts each containing midodrine and/or its active metabolite desglymidodrine. In the present context the term kit is intended to include
  i) a package comprising at least a first and a second pharmaceutical composition, wherein the first composition is designed to release the active drug substance relatively fast in order to obtain a relatively fast onset of the therapeutic effect and the second composition is in the form of a controlled release composition (cf. a co-pending patent application by the same inventors)

which is designed to give a release pattern as described below in order to utilize the possibility of having the active drug substance absorbed not only in the upper part of the gastrointestinal tract but also during its passage through colon, the first and the second composition may be of the same kind, e.g. in the form of tablets or capsules or they may be in the form of two different types of pharmaceutical compositions e.g. the first composition may be in the form of plain tablets or a nasal spray and the second composition may be in the form of controlled release tablets or capsules, and ii) a pharmaceutical composition which include a first and a second part, wherein the first part is designed to release the active drug substance relatively fast in order to obtain a relatively fast onset of the therapeutic effect and the second part is a controlled release part (cf. a co-pending patent application by the same inventors) which is designed to give a release pattern as described below in order to utilize the possibility of having the active drug substance absorbed not only in the upper part of the gastrointestinal tract but also during its passage through colon, and the first and the second part are presented in the form of a single composition such as, e.g. in the form of a tablet, a capsule (e.g. containing pellets which may be the same or different), sachets, powders etc In the following details on the controlled release compositions are given. Whenever relevant, the initial relase described for the controlled release composition also applies for the composition or part of the composition of the kit intended for a relatively fast release of the active substance.

Based on the above findings, the present inventors have developed a pharmaceutical kit comprising as one part or one composition a controlled release composition for oral use containing midrodrine and/or desglymidodrine and the composition is designed to the release of midodrine and/or desglymidodrine in at least the following consecutive steps:

| Step 1 | an initial relatively fast release of midodrine and/or desglymidodrine (in order to obtain a relatively fast onset of action), |
| Step 2 | a steady release or a slower release than in step 1 of midodrine and/or desglymidodrine (in order to maintain a plasma concentration of desglymidodrine which is prolonged and relatively constant), |
| Step 3 | a second rise in release of midodrine and/or desglymidodrine (in order to take advantage of absorption from the colon, i.e. such a second rise release is designed to take place when the composition (or the disintegrated parts of the composition) reaches the colon; normally this is regarded to take about 8 hours after oral intake, and |
| Step 4 | a decline in release rate corresponding to that essentially all midodrine and/or desglymidodrine have been released from the composition. |

The first part or first composition of the kit according to the invention (i.e. the part or composition giving rise to a relatively fast onset of midodrine and/or desglymidodrine) releases the active drug substance as described in step 1 above. Whenever relevant, details relating to such a first step including the relevant formulation techniques as well as the relevant pharmacokinetic parameters (absorption, metabolism and elimination) also apply to the first part or first composition of the kit.

The above release pattern is contemplated in order to obtain the desired plasma concentration of desglymidodrine during day and night after administration orally once daily. Thus, the release pattern above is based on the following requirements with respect to the plasma concentration of desglymidodrine:

1. an initial rise in plasma concentration until a peak concentration is reached (in the present Context "a peak concentration" is intended to mean a peak value, a shoulder value or a plateau value in the concentration),
2. a relatively constant plasma concentration of desglymidodrine for approximately about 4.5–14 hours such as, e.g., about 5–14 hours, about 6–14 hours, about 7–14 hours, about 8–13 hours, about 9–13 hours, about 10–14 hours, about 10–13 hours, or such as, e.g. for at least about 4.5 hours, at least about 5 hours, at least about 6 hours, at least about 7 hours, at least about 8 hours, at least about 9 hours, at least about 10 hours, or at least about 11 hours. In some case, the constant plasma concentration of desglymidodrine may last for at least about 12 hours, at least about 13 hours or at least about 14 hours,
3. a decline in plasma concentration with a half-life of e.g. about 3–4 hours to avoid supine hypertension but other half-lives may also be acceptable e.g. reflecting a continous release of midodrine and/or desglymidodrine from the composition.

Compositions according to the invention are therefore designed based on the following principle; the term "part" is intended to include a separate part within the composition (the composition may contain pellets of e.g. two different types or an integrated element of the composition, e.g. a multilayer tablet):

1. The composition contains a part intended for relatively fast release of midodrine and/or desglymidodrine
2. The composition contains a part intended for prolonged release of midodrine and/or desglymidodrine, and the prolonged release is intended to last for at least about 7–8 hours.
3. The composition contains a part intended to release midodrine and/or desglymidodrine relatively fast when the composition (or the disintegrated parts of the composition) reaches the colon, i.e. about 6–10 hours such as, e.g., about 8 hours after oral administration.
4. The release of midodrine and/or desglymidodrine from a composition according to the invention is terminated at the most about 12–16 hours after administration in order to obtain a wash out period during night.

In one aspect the kit according to the invention comprises a controlled release pharmaceutical composition for oral use comprising midodrine (ST 1085) or a pharmaceutically acceptable salt thereof and/or its active metabolite desglymidodrine (ST 1059) or a pharmaceutically acceptable salt thereof, the composition being adapted to release midodrine and, when present, desglymidodrine in such a manner that a relatively fast peak plasma concentration of desglymidodrine is obtained and that a therapeutically effective plasma concentration of desglymidodrine is maintained for at least about 9 hours such as, e.g. at least about 10 hours, at least about 11 hours, at least about 12 hours, at least about 13 hours, or at least about 14 hours.

More specifically, a relatively fast peak (or shoulder or plateau) plasma concentration of desglymidodrine is obtained about 15 min–6 hours such as, e.g. about 0.5–6 hours, about 1–6 hours, about 2–5.5 hours, or about 2.5–5.2 hours after oral administration of a composition according to the invention.

As mentioned above, it is important to keep the plasma concentration at a relatively constant level and, therefore, the plasma concentration of desglymidodrine after administration of midodrine and/or desglymidodrine is preferably maintained at a therapeutically active level for about 5–16 hours, such as, e.g., about 6–16 hours, about 7–16, about 8–15, about 9–15, about 10–15, about 11–14, about 12–14 or about 13, or least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours or at least about 16 hours.

In the present context, the term "relatively constant level" means that n is n±60%, such as, e.g., n±50% or n±40% and wherein n is the plasma concentration in ng/ml and monitored in a healthy person. The determination of the "relatively constant level" is performed as described in Example 15 herein.

It should be noted that the initial fast release from the controlled release composition may be supplemented with or replaced by a separate fast onset composition (i.e. a first composition of the kit) resulting in a peak plasma concentration within the period stated for the initial rise in plasma concentration. A separate fast onset composition gives a flexibility with respect to the dose administered, i.e. if needed a relatively low or a relatively high dose of the active drug substance may be administered dependent on the patient's needs. Thus, in other aspects the invention relates to such relatively fast onset compositions.

In principle, relevant active drug substances for use in a composition according to the invention are any drug substance for which a dissolution pattern as described below is of relevance. The most interesting drug substances in this respect and with respect to treatment of orthostatic hypotension and urinary incontinence are the prodrug midodrine and its active metabolite desglymidodrine. In a preferred aspect, a composition according to the invention includes midodrine alone, desglymidodrine alone, or a combination of midodrine and desglymidodrine. Of course such compositions may also contain other active drug substances, if relevant.

Generally, after oral administration of a composition according to the invention containing midodrine, a peak plasma concentration of midodrine is obtained 15–90 min after oral administration. Moreover, the plasma concentration of midodrine after oral administration is maintained at a relatively constant level for about 0.7–4 hours such as, e.g. at least about 0.7 hours, at least about 1 hour, at least about 2 hours, at least about 3 hours, or at least about 4 hours.

To this end, the term "relatively constant" is intended to mean m is m±60%, such as, .e.g., m±50% or m±40% and wherein m is the plasma concentration in ng/ml and monitored in a healthy person The determination of the "relatively constant level" is performed as described in Example 15 herein.

The relatively fast onset compositions in a kit according to the invention may be in the form of tablets such as, e.g, conventional tablets, melt tablets, coated tablets, buccal tablets, capsules, sachets, drops, dispersions, solutions, emulsions, suspensions, gels, hydro gels, nasal compositions such as, e.g. nasal spray or nasal powder compositions, compositions for pulmonary administration such as, e.g inhalators, chewing compositions such as, e.g., chewing gum, etc. Especially suited compositions for a fast onset is compositions in fluid form and in the form of nasal compositions as well as quick release tablets.

In the following further details on a controlled release composition of the kit according to the invention is given.

Examples on relatively fast onset compositions are illustrated in the Examples.

Dissolution Requirements

As described in the following, a target plasma profile and release profile can be designed for the controlled release composition or the controlled release part of the kit comprising midodrine and/or the active metabolite desglymidodrine.

Based on our knowledge of the plasma profile of a midodrine solution and obtained $C_{max}$ values for inactive midodrine and active metabolite desglymidodrine after tablet administration a target in vivo profile has been estimated (FIGS. 1 and 2).

The target profile is based on the findings discussed above and the assumption that it would be preferable to have a fast onset of action and a relatively stable plasma level for 8–11 hours and thereafter to eliminate the drug during the night phase to avoid supine hypertension.

The presumptions made in estimating this target profile were:

i) a fast peak and an effective concentration of the active metabolite for approximately 14 hours are desired from a therapeutic point of view (FDA recommendation: latest dose at 6 pm), ii) that the first fraction of the composition should have an absorption rate similar to that of plain tablets, iii) that the peak concentration should not be higher than the peak concentration observed after administration of 33% of the total dose in the form of a plain tablet, iv) that the plateau level for midodrine should last for approximately 8 hours and for desglymidodrine for approximately 11 hours, v) that the drug reaches colon after approximately 8 hours, vi) that midodrine is absorbed in the colon with a $t_{max}$ of 3 hours (desglymidodrine) compared to a $t_{max}$ of ½ hour (midodrine) when absorbed in the small intestine, vii) that midodrine will not be measured after the colon absorption as midodrine but only as desglymidodrine, viii) that $t_{max}$ of desglymidodrine will appear 1 hour after oral administration of midodrine, ix) that $t_{1/2}$ for midodrine is ½–1 hour and for desglymidodrine 3–4 hours, and x) that $C_{max}$ after 7.5 mg midodrine is approximately 11 ng/ml (midodrine) and approximately 3.75 ng/ml (desglymidodrine).

Based on the fact that midodrine plain tablets are dosed from 2.5 mg–10 mg up to 4 times daily and that an individual variation in need for midodrine is known, the level of the target plasma profile may vary a factor 0.1–5. The shape of the profile is more important than the exact level of plasma concentrations.

The estimated target plasma profile has been deconvoluted with plasma concentrations from an oral solution for both midodrine and desglymidodrine to give an estimated in vivo dissolution profile (FIGS. 3 and 4). All data were normalised to a dose of 7.5 mg before deconvolution. In the deconvolution a time interval of 0.5 hours was employed (cf: Langenbucher F., Möller H. Correlation of in vito drug release with in vivo response kinetics. Part I: mathematical treatment of time functions. Pharm. Ind.1983;45:623–8, and Langenbucher F., Möller H. Correlation of in vitro drug release with in vivo response kinetics. Part II: Use of function parameters. Pharm. Ind. 1983;45:629–33).

The presumption in making this deconvolution was that the daily dose of midodrine is the same irrespective of whether the new CR composition or a plain tablet or a solution were administered.

Using this deconvolution, the in vitro dissolution profile for a composition according to the invention is estimated.

Presumptions for this Estimation are
i) that the in vitro-in vivo correlation will be 1:1
ii) that it is possible with the new invention to make a product with essential 100% release after 10–14 hours
iii) that midodrine is absorbed as such or as the active metabolit through the whole gastrointestinal tract (including colon) in order not to loose any amount of active drug substance ready for absorption into the circulatory system.

Target Release in vitro Profile Estimated as Described Above

| Time (hours) | % w/w released midodrine |
| --- | --- |
| 0.5 | 25 |
| 1 | 35 |
| 2 | 39 |
| 3 | 47 |
| 4 | 53 |
| 5 | 60 |
| 6 | 66 |
| 7 | 73 |
| 8 | 80 |
| 9 | 87 |
| 10 | 93 |
| 12 | 100 |

In order to reflect the second rise in release of midodrine corresponding to the time when the composition reaches the colon, the following target profile is also relevant:

| Time (hours) | % w/w released midodrine |
| --- | --- |
| 0.5 | 25 |
| 1 | 35 |
| 2 | 39 |
| 3 | 47 |
| 4 | 53 |
| 5 | 60 |
| 6 | 66 |
| 7 | 75 |
| 8 | 90 |
| 9 | 95 |
| 10 | 97 |
| 11 | 99 |
| 12 | 100 |

As apparent from the above, an initial relatively fast release of midodrine is suitable and after about 6–8 hours a second rise in release should be observed. Accordingly, a target release rate profile is as follow (the release rate is given in % dissolved/hour):

about 35%/hour about 30 min after start of the dissolution test,
about 12%/hour about 1 hour after start of the dissolution test,
about 6%/hour about 2 hours after start of the dissolution test,
about 7%/hour about 3 hours after start of the dissolution test,
about 6.5%/hour about 4 hours after start of the dissolution test,
about 6.5%/hour about 5 hours after start of the dissolution test,
about 7.5%/hour about 6 hours after start of the dissolution test,
about 12%/hour about 7 hours after start of the dissolution test,
about 10%/hour about 8 hours after start of the dissolution test,
about 3.5%/hour about 9 hours after start of the dissolution test
about 2%/hour about 10 hours after start of the dissolution test
about 1%/hour about 12 hours after start of the dissolution test.

In FIG. 5 is given a target dissolution profile and a target release rate curve.

As dissolution test any acceptable method may be applied, preferably a method according to USP or Ph.Eur. Throughout the examples 1, 3–10, the following method has been employed: the in vitro dissolution method according to USP and Ph.Eur. employing dissolution apparatus 2 (paddle), 100 rpm, 0.1 N hydrochloric acid as dissolution medium and a temperature of 37° C. It is contemplated that other dissolution media may be suitable as well as another rotation speed.

Reference is given to the claims herein where further details concerning the dissolution patterns and the release rates of a controlled release composition of a kit according to the invention are given.

With respect to the release of midodrine and/or desglymidodrine from the relatively fast onset composition or part of the kit, the following applies:

Tablets (plain): disintegration time less than 5 min and often less than 5 min such as, e.g. 1–3 min.

Sublingual, buccal and melt tablets: by mould technique: disintegration time less than about 30 sec such as, e.g. about 2–10 sec; by compression or compacting, disintegration time less than about 4 min such as, e.g. about 2–3 min.

Other compositions normally contain midodrine and/or desglymidodrine in dissolved form. Thus, no retardation of the release of the active drug substance from such compositions is expected.

Specific Embodiments of Interest are as Follows

Controlled release compositions of the kit according the invention wherein the release pattern of midodrine from the controlled release composition—when tested in vitro using Dissolution Method I or II described in the Experimental part herein and employing a basket according to USP and Ph. Eur, 100 rpm, 600 ml 1 N hydrochloric acid as dissolution medium and a temperature of 37° C.—is:

1–15% w/w is released from the composition within the first 30 min after start of the test,
10–35% (25%) w/w is released about 30 min after start of the test,
15–40% (35%) w/w is released about 1 hour after start of the test
20–50% (39%) w/w is released about 2 hours after start of the test,
20–55% (47%) w/w is released about 3 hours after start of the test,
25–75% such as, e.g., 25–65% (53%) w/w is released about 4 hours after start of the test,
30–74% (66%) w/w is released about 6 hours after start of the test,
40–85% (80%) w/w is released about 8 hours after start of the test,
65–100% (93%) w/w is released about 10 hours after start of the test,
90–110% (100%) w/w is released about 12 hours after start of the test.

A release pattern of midodrine from a controlled release composition of the kit according to the invention—when tested in vitro using Dissolution Method III or IV described herein and employing a basket according to USP and Ph. Eur, 100 rpm, a first dissolution medium with a pH of about 1.0 for the first 2 hours of the testing followed by a second dissolution medium with a pH of about 6.0 for the next 5.5 hours and finally a third dissolution medium with a pH of about 7.5 until the end of the testing, and a temperature of 37° C.—may also be:

- 1–15% w/w is released from the composition within the first 30 min after start of the test,
- 10–35% (25%) w/w is released about 30 min after start of the test,
- 15–40% (35%) w/w is released about 1 hour after start of the test
- 20–50% (39%) w/w is released about 2 hours after start of the test,
- 20–55% (47%) w/w is released about 3 hours after start of the test,
- 25–75% such as, e.g., 25–65% (53%) w/w is released about 4 hours after start of the test,
- 30–74% (66%) w/w is released about 6 hours after start of the test,
- 40–95% such as, e.g., 45–85% (80%) w/w is released about 8 hours after start of the test,
- 65–100% (93%) w/w is released about 10 hours after start of the test,
- 75–110% (100%) w/w is released about 12 hours after start of the test.

Another release pattern of midodrine from a controlled release composition of a kit according to the present invention—when tested in vitro employing any of Dissolution Method I, II, III or IV as described herein,—is as follows (±30% w/w such as, e.g., ±25%, ±20%, ±15% or ±10% of the values stated below):

- about 25% w/w is released about 30 min after start of the test,
- about 35% w/w is released about 1 hour after start of the test,
- about 39% w/w is released about 2 hours after start of the test,
- about 47% w/w is released about 3 hours after start of the test,
- about 53–56% such as, e.g., about 53% w/w is released about 4 hours after start of the test,
- about 66–72% such as, e.g., about 66% w/w is released about 6 hours after start of the test,
- about 80–85% w/w is released about 8 hours after start of the test,
- about 93% w/w is released about 10 hours after start of the test,
- about 100% w/w is released about 12 hours after start of the test.

A still further release pattern of midodrine from a controlled release composition of a kit according to the invention—when tested in vitro employing any of Dissolution Method I, II, III or IV as described herein—is:

- 1–15% w/w is released from the composition within the first 30 min after start of the test,
- 10–35% (25%) w/w is released about 30 min after start of the test,
- 15–40% (35%) w/w is released about 1 hour after start of the test,
- 20–50% (39%) w/w is released about 2 hours after start of the test,
- 20–55% (47%) w/w is released about 3 hours after start of the test,
- 25–75% such as 25–65% (53%) w/w is released about 4 hours after start of the test,
- 30–74% (66%) w/w is released about 6 hours after start of the test,
- 35–85% (75%) w/w is released about 7 hours after start of the test,
- 45–95% (90%) w/w is released about 8 hours after start of the test,
- 65–100% (97%) w/w is released about 10 hours after start of the test,
- 90–110% (100%) w/w is released about 12 hours after start of the test.

Another suitable release pattern of midodrine from a controlled release composition of a kit according to the invention—when tested in vitro employing any of Dissolution Method I, II, III or IV as described herein—is:

- 1–15% w/w is released from the composition within the first 30 min after start of the test,
- 15–35% (25%) w/w is released about 30 min after start of the test,
- 20–40% (35%) w/w is released about 1 hour after start of the test,
- 25–50% (39%) w/w is released about 2 hours after start of the test,
- 30–55% (47%) w/w is released about 3 hours after start of the test,
- 40–75% such as, e.g., 40–65% (53%) w/w is released about 4 hours after start of the test,
- 50–74% (66%) w/w is released about 6 hours after start of the test,
- 60–85% (75%) w/w is released about 7 hours after start of the test,
- 70–95% (90%) w/w is released about 7 hours after start of the test,
- 80–100% (97%) w/w is released about 10 hours after start of the test,
- 90–110% (100%) w/w is released about 12 hours after start of the test.

In other aspects, the release pattern of midodrine from a controlled release composition of a kit according to the invention—when tested in vitro employing any of Dissolution Method I, II, III or IV as described herein—is as follows (±30% w/w, ±20% w/w, ±10% w/w, ±7.5% w/w or ±5% w/w of the values stated below):

- about 25% w/w is released about 30 min after start of the test,
- about 35% w/w is released about 1 hour after start of the test,
- about 39% w/w is released about 2 hours after start of the test,
- about 47% w/w is released about 3 hours after start of the test,
- about 53% w/w is released about 4 hours after start of the test,
- about 66 w/w is released about 6 hours after start of the test,
- about 75% w/w is released about 7 hours after start of the test, about 80% w/w is released about 8 hours after start of the test, about 90% w/w is released about 10 hours after start of the test, about 100% w/w is released about 12 hours after start of the test, or about 28% w/w is released about 30 min after start of the test, about 35% w/w is released about 1 hour after start of the test, about 41% w/w is released about 2 hours after start of the test, about 45% w/w is released about 3 hours after start of the test, about 55% w/w is released about 4 hours after start of the test, about 70 w/w is released about 6 hours after start of the test, about 78% w/w is released about 7 hours after start of the test, about 90% w/w is released about 8 hours after start of the test, about 95% w/w is released about 10 hours after start of the test, about 100% w/w is released about 12 hours after start of the test.

As seen in the examples herein it is possible to obtain a release pattern. which corresponds to the above-mentioned values ±7.5% or ±5%.

In another aspect, the invention relates to a kit comprising a controlled release composition, wherein the release pattern of midodrine from the composition—when tested in vitro employing any of Dissolution Method I, II, III or IV as described herein—is as follows (±30% w/w, ±20% w/w, ±10% w/w, ±7.5% w/w or ±5% w/w of the values stated below):

about 20% w/w is released about 30 min after start of the test, about 20% w/w is released about 1 hour after start of the test, about 20% w/w is released about 2 hours after start of the test, about 20% w/w is released about 3 hours after start of the test about 25% w/w is released about 4 hours after start of the test, about 45 w/w is released about 6 hours after start of the test, about 75% w/w is released about 7 hours after start of the test, about 90% w/w is released about 8 hours after start of the test, about 95% w/w is released about 10 hours after start of the test, about 100% w/w is released about 12 hours after start of the test.

In those cases where the controlled release composition of a kit according to the invention contains desglymidodrine or a pharmaceutically acceptable salt thereof then the release pattern of desglymidodrine generally follows the patterns given above for midodrine.

If the controlled release composition of a kit according to the invention contains midodrine or a pharmaceutically acceptable salt thereof and desglymidodrine or a pharmaceutically acceptable salt thereof, then the release pattern of the sum of midodrine and desglymidodrine is calculated on a molar basis follows the patterns given above for midodrine.

As earlier discussed the release rate of midodrine (and/or desglymidodrine) is important in order to achieve a suitable release pattern. Thus, a controlled release composition of a kit according to the present invention normally has a release rate of midodrine—when tested in vitro employing any of Dissolution Method I, II, III or IV—that corresponds to a curve that has a shape corresponding to i) a relatively fast first initial release followed by ii) a steady release or a slower release than in step i) above, which is followed by iii) a second rise in release rate and. finally, iv) a decline in release rate.

In general, the second rise in release rate takes place 5–10 hours such as, e.g., about 5–9 hours, about 6–8 hours after start of the dissolution test, or 6.5–9 hours after start of the dissolution test simulating the time it takes to reach the colon after oral administration.

With respect to the steady release period, it normally starts about 1–3 hours after the start of the dissolution test, and the steady release is maintained for at least 2 hours such as, e.g. at least 3 hours, at least 4 hours, at least 5 hours, at least 6 hours, at least 7 hours, at least 8 hours such as about 6–8 hours.

More specifically, the release rate of midodrine (or desglymidodrine or the sum of midodrine and desglymidodrine on a molar basis) from a controlled release composition of a kit according to the invention—when tested in vitro employing dissolution apparatus 2 (paddle) according to USP and Ph. Eur, 100 rpm, 0.1 N hydrochloric acid as dissolution medium or any of Dissolution Method I, II , III or IV as described herein and a temperature of 37° C.—in %/hour is as follows (±10–40% such as, e.g. ±10–30% or ±10%, ±15% or ±20% of the values stated below):

about 35%/hour about 30 min after start of the test(range e.g. 15–40%/hour), about 12%/hour about 1 hour after start of the test (range e.g 4–15%/hour), about 6%/hour about 2 hours after start of the test (range e.g. 2–10%/hour), about 7%/hour about 3 hours after start of the test (range e.g. 2–10%/hour), about 6.5%/hour about 4 hours after start of the test (range e.g. 2–15%/hour), about 7.5%/hour about 6 hours after start of the test (range e.g. 2–30% such as, e.g., 2–10%/hour), about 10%/hour about 8 hours after start of the test (range e.g. 2–15%/hour), about 2%/hour about 10 hours after start of the test (range e.g. 0–10%/hour), about 1%/hour about 12 hours after start of the test (range e.g. 0–10%/hour).

A controlled release composition of a kit according to the invention is normally suitable for administration once or twice daily, and it differs from a plain tablet composition, e.g. Gutron® tablets, in many ways. In the following is given pharmacokinetic values of importance for achievement of a prolonged therapeutic effect of a composition according to the invention. Further details concerning the definition of the parameters and the method of obtaining relevant values are given in Example 15 herein.

When tested as described in Example 15 herein, $W_{50}$ of midodrine (defined as corresponding to the time the plasma concentration curve is or is above 50% of the $C_{max}$ value) is from about 1 to about 9 hours such as, e.g. from about 1.3 to about 8 hours such as, e.g. at least about 1.4 hours, at least about 1.5 hours, or at least about 1.7 hours.

Compared with a standard midodrine composition, $W_{50}$ is increased with a factor of at least 2 such as, e.g., at least 2.5. A suitable comparison is performed against a plain Gutron® tablet administered in the same dose and $W_{50}$ is determined from a plasma concentration versus time curve. The plasma concentration reflects the sum concentration in nmol/l of midodrine and desglymidodrine.

Analogously, $W_{75}$, (T>75% $C_{max}$) is increased with a factor of at least 2 when compared with a plain Gutron® tablet administered in the same dose. $W_{75}$ (T>75% $C_{max}$) is determined from a plasma concentration versus time curve and the plasma concentration reflects the sum concentration in nmol/l of midodrine and desglymidodrine.

Likewise, $W_{50}$ of desglymidodrine (defined as corresponding to the time the plasma concentration curve is or is above 50% of the $C_{max}$ value) is from about 5 to about 12 hours such as, e.g. from about 6 to about 11 hours such as, e.g. at least about 7 hours.

Furthermore, $T_{max}$ is increased with a factor of at least 2 when compared with a plain Gutron® tablet administered in the same dose. $T_{max}$ is determined from a plasma concentration versus time curve and the plasma concentration reflects the sum concentration in nmol/l of midodrine and desglymidodrine.

MRT (mean residence time) is increased with a factor of at least 1.5 such as, e.g., at least 2, at least 2.5 or at least 3 when compared with a plain Gutron® tablet administered in the same dose. MRT is determined from a plasma concentration versus time curve and the plasma concentration reflects the sum concentration in nmol/l of midodrine and desglymidodrine.

MRT for midodrine is at least about 1.5 hours such as, e.g., at least about 2 hours, at least about 2.5 hours or at least about 3 hours, and/or MRT for desglymidodrine is at least about 6 hours such as, e.g., at least about 7 hours, at least about 7.5 hours, at least about 8 hours, at least about 8.5 hours, at least about 9 hours, or at least about 9.5 hours.

Active Drug Substances

As mentioned above, a kit according to the invention is suitable for use for any active drug sustance for which a dissolution pattern as described above is of relevance, and which beneficially can be administered only once or twice daily.

With respect to treatment of orthostatic hypotension and the other conditions mentioned above, midodrine and its active metabolite desglymidodrine are drugs of choice.

Midodrine as well as desglymidodrine exist in racemic form and in the form of the two enantiomeric species.

Midodrine is also known as ST 1085, or 2-amino-N-[2-(2,5-dimethoxyphenyl)-2-hydroxyethyl]-acetamide. It may be in present in racemic form, i.e. as (±)-midodrine, (±)-ST 1085, or (±)-2-amino-N-[2-(2,5-dimethoxyphenyl)-2-hydroxyethyl]-acetamide, (±)-2-amino-N-[2-2-(2,5-dimethoxyphenyl)-2-hydroxyethyl]-acetamide, or in its enatiomeric form as (−)-midodrine, (R)-midodrine, (−)-ST 1085, (R)-ST 1085, (−)-2-amino-N-[2-(2,5-dimethoxyphenyl)-2-hydroxyethyl]-acetamide, or (R)-2-amino-N-[2-(2,5-dimethoxyphenyl)-2-hydroxyethyl]-acetamide, or in its other enantiomeric form (+)-midodrine or (S)-midodrine, (+)-ST 1085, or (S)-ST 1085, (+)-2-amino-N-[2-(2,5-dimethoxyphenyl)-2-hydroxyethyl]-acetamide or (S)-2-amino-N-[2-(2,5-dimethoxyphenyl)-2-hydroxyethyl]-acetamide.

Desglymidodrine is also known as ST 1059, alpha-(aminomethyl)-2,5-dimethoxy-benzenemethanol. It may be present in racemic form, i.e. as (±)-desglymidodrine, (±)-ST 1059 or (±)-alpha-(aminomethyl)-2,5-dimethoxy-benzenemethanol, or in its enantiomeric form as (−)-desglymidodrine, (R)-desglymidodrine, (−)-ST1059, (R)-ST1059, (−)-alpha-(aminomethyl)-2,5-dimethoxy-benzenemethanol or (R)-alpha-(aminomethyl)-2,5-dimethoxy-benzenemethanol, or in its other enatiomeric form (+)-desglymidodrine, (S)-desglymidodrine, (+)-ST1059(S)-ST1059(+)-alpha-(aminomethyl)-2,5dimethoxy-benzenemethanol or (S)-alpha-(aminomethyl)-2,5-dimethoxy-benzenemethanol.

A composition of a kit according to the invention may therefore include midodrine in the racemic form (RS), in the enantiomeric form (R), in the enantiomeric form (S) or in mixtures thereof.

In an embodiment according to the invention the kit comprises a composition which includes at least 90% w/w such as, e.g., at least 95% w/w, at least 97% w/w, at least 98% w/w, at least 99% w/w of midodrine in the therapeutically active enantiomeric form; and the therapeutically active enantiomeric form of midodrine is (−)-2-amino-N-(β-hydroxy-2,5-dimethoxyphenethyl)-acetamide or the (R) form of midodrine.

In another embodiment according to the invention, a composition contains the active metabolite desglymidodrine (ST 1059), and desglymidodrine is present in the form of (±)-α-(aminomethyl)-2,5-dimethoxy-benzenemethanol (±ST 1059), (+)-α-(aminomethyl)-2,5-dimethoxy-benzenemethanol (+ST 1059), (−)-α-(aminomethyl)-2,5-dimethoxy-benzenemethanol (−ST 1059) or mixtures thereof.

In a still further embodiment a composition of a kit according to the invention contains desglymidodrine in the racemic form (RS), in the enantiomeric form (R), in the enantiomeric form (S) or in mixtures thereof, or it contains at least 90% w/w such as, e.g., at least 95% w/w, at least 97% w/w, at least 98% w/w, at least 99% w/w of desglymidodrine is present in the therapeutically active enantiomeric form. The therapeutically active enantiomeric form of desglymidodrine is contemplated to be (−)-α-(aminomethyl)-2,5-dimethoxy-benzenemethanol (−ST 1059) or the (R) form of desglymidodrine ((R) ST 1059).

In a composition according to the invention midodrine and/or desglymidodrine are present in the form of a pharmaceutically acceptable salt such as a salt formed between midodrine and/or desglymidodrine and an inorganic acid such as e.g., a hydrochloride, a hydrobromide, a hydroiodide, a nitrate, a nitrite, a $H_3PO_3$ salt, a $H_3PO_4$ salt, a $H_2SO_3$ salt, a sulfate, a $H_2SO_5$ salt, or a salt formed between midodrine and/or desglymidodrine and an organic acid such as organic acids like e.g. $H_2CO_3$, acetic acid, $C_2H_5COOH$, $C_3H_7COOH$, $C_4H_9COOH$, $(COOH)_2$, $CH_2(COOH)_2$, $C_2H_5(COOH)_2$, $C_3H_6(COOH)_2$, $C_4H_3(COOH)_2$, $C_5H_{10}(COOH)_2$, fumaric acid, maleic acid, lactic acid, tartaric acid, citri acid, ascorbic acid, benzoic acid, salicylic acid and phthalic acid A composition according to the invention may comprise a further active drug substance, i.e. the composition may be in the form of a so-called combination composition comprising at least two different active drug substances. The further active drug substance may be any active drug substance, which beneficially is used in combination with midodrine and/or desglymidodrine. Interesting examples of further active drug substances are steroids like e.g. hydrocortisone or fludrocortisone or somatostin analogoues like e.g. octreotide.

Dosage

In general, the dosage of the active drug substance present in a composition according to the invention depends inter alia on the specific drug substance, the age and condition of the patient and of the disease to be treated.

A composition according to the present inventions aims at a dosage once or twice daily, preferably once daily. In the present context the term "once daily"/"once-a-day" is intended to mean that it is only necessary to administer the pharmaceutical composition once a day in order to obtain a suitable therapeutic and/or prophylactic response; however, any administration may comprise co-administration of more than one dosage unit such as, e.g. 2–4 dosage units.

In agreement with the above-mentioned definition of "once daily"/"once-a-day", "twice daily"/"twice-a-day" is supposed to mean that it is only necessary to administer the controlled release composition of the kit at the most twice a day in order to obtain a suitable therapeutic and/or prophylactic response in the patient which can form a basis for an individual supply with the relatively fast onset composition.

Irrespective of the above-mentioned definitiones of "once" and "twice" daily, a dosage unit constructed to deliver the active ingredient after only one daily administration is preferred. However, due to individual circumstances some patients may need a new dosage after e.g. 7–18 hours such as, e.g. about 7–8 hours or about 12 or about 18 hours if the patient e.g. has abnormal absorption or bowel transit time. If the individual has a relatively fast bowel transit time, some of the active drug substance may be excreted before the full dosage is released.

With respect to midodrine, the normal daily dose is from 2.5 to 10 mg three or up to four times daily (calculated as midodrine hydrochloride), i.e. a daily dose of from about 7.5 mg to about 40 mg in the treatment of orthostatic hypertension. However, the daily dose in the treatment of urinary incontinence may be different and, accordingly, a composition according to the present invention typically contains from about 2.5mg to about 50 mg midodrine such as, e.g. 2.5 mg, 5 mg, 7.5 mg, 10 mg. 12.5 mg, 15 mg, 17.5 mg, 20 mg, 25 mg, 30 mg, 35 mg, 40 mg, 45 mg or 50 mg. In the cases, where midodrine is employed in another form e.g. in another salt form than midodrine hydrochloride, the above-mentioned dosage ranges are of course to be recalculated so that the same dosage is employed on a molar basis.

The total daily doses of midodrine will depend on the indication for the treatment and the individually tolerated doses. The kit of the present invention provides a possibility of a treatment regimen adapted for the specific patient The individual fast onset doses of the kit of the invention may be from 0.2 mg to 10 mg, preferreably from 0.5 mg to 7.5 mg such as of 0.75 mg, 1 mg, 1.25 mg, 1.5 mg, 2 mg, 2.5 mg, 3mg, 4mg, or 5 mg.

As discussed above, midodrine may be present as the racemic form or in one of its enantiomeric forms, preferably the therapeutically active enantiomeric form. In those cases where midodrine is present in its therapeutically active enantiomeric form a reduction in the above-mentioned dosage ranges may be relevant.

With respect to the dosage in those cases where desglymidodrine is employed it is envisaged that the same dosages as mentioned above are relevant, Formulation Techniques In principle any relevant controlled formulation technique for preparing an oral controlled release composition may be applied. Thus, the dosage form may be in the form of a liquid having e.g. particles dispersed in a dispersion medium or it may be in the form of a single or a multiple unit dosage form intended for use as such as for dispersing in a dispersion medium before use Any relevant formulation technique for preparing pharmaceutical compositions may be applied when formulating the relatively fast onset composition. A person skilled in the art of pharmaceutical formulation techniques can find guidance in the handbook Remington's Pharmaceutical Sciences and in the Examples herein.

In the following is given a short review on general controlled release formulation techniques with an aim of obtaining the type of dissolution profile described above. In the compositions described below a person skilled in the art will know how to incorporate a part that gives rise to a relatively fast release of the active drug substance. As an example, such a part may be incorporated in an outermost coating layer comprising the active substance or it may be incorporated in the form of pellets formulated without retarding agents neither in the cores nor in a coating.

Examples of Different Controlled Release Technologies are
1, Single units
1.1 Coated matrix
1.2 Double or triple compression
1.3 Multilayer coating
2. Multiple units
2.1 Units having a controlled release coating
2.2 Units having a controlled release matrix
2.3 Units having a controlled release compression coating
2.4 Units with a multilayer coating.

Coated Matrix

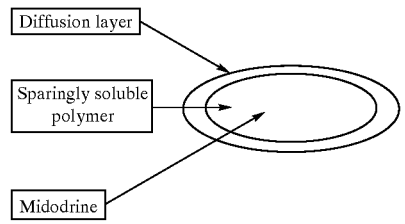

The idea behind the use of this technology is to coat a sparingly soluble and/or swellable polymer, in which midodrine (and/or any relevant substance such as, e.g. desglymidodrine) is embedded, with an insoluble diffusion barrier. The diffusion of midodrine is controlled by the matrix and the coat. This technique will cover the type of dissolution profile described in step 2 above.

If a soluble outer film layer containing midodrine is applied on the coated matrix, step 1 is achievable too.

Step 3 can be covered by including enteric coated units embedded in the matrix.

Double or Triple Compression

The basic idea for such a formulation is a core of a polymer having midodrine and/or desglymidodrine incorporated. This core is compression coated with a polymer with midodrine incorporated in the same or another concentration than in the core. When triple compression is employed, the coated core is compression coated once more with a polymer with midodrine in the same or another concentration as in the first coat Finally, the doble or triple compression unit is spray coated and midodrine is incorporated in the coat. However, the concentrations of midodrine in the different coats may vary markedly. The idea behind the multiple layers is that when the midodrine of the first layer has been almost depleted, the next layer takes over and levels out or changes the release profile.

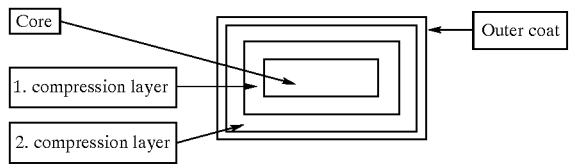

The spray coating with midodrine and/or desglymidodrine gives an immediate burst of the active compound.

Steps 1, 2 and 3 can be covered by use of this technique.

Multilayer Coating

The idea with this type of formulation is to coat an inert core with several layers of diffusion barriers, each barrier containing different concentrations of midodrine. The concentration should be highest in the inner coat and lowest in the outer coat The purpose of the concentration gradient is to compensate for the increasing diffusion distance closer to the core. If the thickness of the diffusion barriers and the concentration gradients are correctly adjusted, steps 1, 2 and 3 will be obtainable.

Use of Enteric Coating

The correct start of step 3 in the triple compression and multilayer technologies might be optimized by the use of an enteric polymer.

Use of Amylose as Colon Degradable Excipient

The correct start of step 3 in the triple compression and multilayer technologies might also be optimized by the use of an amylose containing film coating such as a coating containing ethylcellulose and amylose or Eudragit RS and amylose.

Multiple Unit Systems

The units comprise pellets, granules, crystals, mini tablets or mixtures thereof.

Step 1 can be covered by an uncoated unit.

Step 2 can be covered by the application of a controlled release coating or by formulating the unit as a matrix or a coated matrix Step 3 can be covered by the use of an enteric polymer or amylose, or by having units compressed as described in the triple compression technology.

In specific embodiments, a composition of a kit according to the invention is in the form of a solid dosage form such as, e.g., tablets, capsules, sachets, solid dispersion, crystals, granules and the like.

A controlled release composition of a kit according to the invention can also comprise at least two parts such as at least a first and a second part, each part contains midodrine and/or, if present, desglymidodrine and the first part being adapted to release midodrine and/or, if present, desglymidodrine, in a controlled manner during the first 0–14 such as, e.g. 0–11 hours after oral intake and the second part being adapted to release midodrine and/or, if present, desglymidodrine, starting at least 6 hours after oral intake.

In such a composition at least one of the at least two parts is present in the composition in the form of a multiplicity of individual units such as, e.g. pellets or minitablets.

The two parts of the at least two parts may also be present in the composition in the form of a multiplicity of individual units such as, e.g. pellets or minitablets, and the two parts may be in admixture.

A controlled release composition of a kit according to the invention may also be in multiple unit dosage form such as, e.g., wherein at least one of the at least two parts comprises at least two different types of pellets, the first type of pellets corresponding to a first fraction and the second type of pellets corresponding to a second fraction.

Moreover, the at least two parts of the controlled release composition may comprise at least two different types of pellets, the first type of pellets corresponding to the first part and the second type of pellets corresponding to the second part.

A controlled release composition of a kit according to the invention may also as individual units contain minitablets, i.e. be in the form of a multiple unit dosage form comprising at least two different types of minitablets, the first type of minitablets corresponding to the first part and the second type of minitablets corresponding to the second part. In the present context a minitablet is a tablet having a size in a range corresponding to from about 0.7 mm to about 7 mm in diameter such as, e.g., in a range corresponding to from about 1 to about 7 mm, from about 1.5 to about 6 mm, from about 2 mm to about 5 mm, from about 2 mm to about 4 mm such as in a range corresponding to from about 2 to about 3 mm in diameter.

A controlled release composition of a kft according to the invention may also as individual units contain relatively large crystals of the active drug substance. In such cases, the size of the unit is at the most about 1 mm such as, e.g., in a range corresponding to from about 0.1 to about 1 mm, from about 0.2 mm to about 0.8 mm, from about 0.2 mm to about 0.7 mm or from about 0.3 mm to about 0.7 mm.

A controlled release composition of a kit according to the invention may be in the form of a multiple unit dosage form, wherein the first or the second part is in the form of minitablets, in the form of pellets or in the form of large crystals of the active drug substance.

Moreover, at least two fractions may be present in a tablet such as, e.g. a multilayer tablet and the at least first and the second part are each comprised in a layer in the tablet.

Furthermore, a composition of a kit according to the invention may comprise a third part adapted to release midodrine and, if present, desglymidodrine relatively fast from the composition and/or a fourth part adapted to release midodrine and/or desglymidodrine from the composition 6–10 hours after oral intake.

In one embodiment the third and/or, if present, the fourth part comprise pellets or minitablets or are a layer in a tablet.

With respect to release kinetics, a controlled release composition of a kit according to the invention may have a first part, a second part a third part and/or a fourth part which have a release kinetic corresponding to a zero or a first order release or a mixture of zero and first order release. Other orders of release may be 1.5, 2, 3 or 4.

All the above-mentioned combinations of different types of compositions or formulation techniques apply, whenever relevant, mutatis mutandi to the fast release part or composition of the kit of the invention. The same applies to the combination of the controlled release part or composition and the fast release part or composition of a kit of the invention Pharmaceutically Acceptable Excipients Apart from the active drug substance in the composition, a pharmaceutical composition according to the invention may further comprise pharmaceutically acceptable excipients.

In the present context, the term "pharmaceutically acceptable excipient" is intended to denote any material, which is inert in the sense that it substantially does not have any therapeutic and/or prophylactic effect per se. A pharmaceutically acceptable excipient may be added to the active drug substance with the purpose of making it possible to obtain a pharmaceutical composition, which has acceptable technical properties Fillers/diluents/binders may be incorporated such as sucrose, sorbitol, mannitol, lactose (e.g., spray-dried lactose, α-lactose, β-lactose, Tabletose®, various grades of Pharmatose®, Microtose or Fast-Floc®), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), hydroxypropylcellulose, L-hydroxypropylcellulose (low-substituted) (e.g. L-HPC-CH31, L-HPC-LH11, LH 22, LH 21, LH 20, LH 32, LH 31, LH30), dextrins, maltodextrins (e.g. Lodex® 5 and Lodex® 10), starches or modified starches (including potato starch, maize starch and rice starch), sodium chloride, sodium phosphate, calcium phosphate (e.g. basic calcium phosphate, calcium hydrogen phosphate), calcium sulfate, calcium carbonate, gelatine, polyvinylpyrrolidone (30, 90, Kollidon VA 64), and sodium carboxymethylcellulose.

Disintegrants may be used such as cellulose derivatives, including microcrystalline cellulose, low-substituted hydroxypropyl cellulose (e.g. LH 11, H 22, LH 21, LH 20, LH 32, LH 31, LH30); starches, including potato starch; croscarmellose sodium (i.e. cross-linked carboxymethylcellulose sodium salt; e.g. Ac-Di-Sol®): alginic acid or alginates; insoluble polyvinylpyrrolidone (e.g. Polyvidon® CL, Polyvidon® CL-M, Kollidon® CL, Polyplasdone® XL, Polyplasdone® XL-10); sodium carboxymethyl starch (e.g. Primogel®) and Explotab®).

Glidants and lubricants may be incorporated such as stearic acid, metallic stearates, talc, waxes and glycerides with high melting temperatures, colloidal silica, sodium stearyl fumarate, polyethylenglycols and alkyl sulphates.

Surfactants may be employed such as non-ionic (e.g., polysorbate 20, polysorbate 21, polysorbate 40, polysorbate 60, polysorbate 61, polysorbate 65, polysorbate 80, polysorbate 81, polysorbate 85, polysorbate 120, sorbitane monoisostearate, sorbitanmonolaurate, sorbitan monopalmitate, sorbitan monostearate, sorbitan monooleate, sorbitan sesquioleate, sorbitan trioleate, glyceryl monooleate and polyvinylalkohol), anionic (e.g., docusate sodium and sodium lauryl sulphate) and cationic (e.g., benzalkonium chloride, benzethonium chloride and cetrimide) or mixtures thereof. Examples of amphoteric surfactants are 1,2-diacyl-L-phosphatidylcholine, N-lauryl-N,N-dimethylglycine, alkylaminopropionic acid, alkyliminodipropionic acid, and dimethyl-(3-palmitamidopropyl)-aminoacetate.

Other appropriate pharmaceutically acceptable excipients may include colorants, flavouring agents, pH adjusting agents, solubilizing agents, wetting agents and buffering agents Modified Release Coating A unit comprised in a composition according to the invention may be coated with a modified release coating.

The modified release coating is a substantially water-insoluble but water-diffusible coating.

The modified release coating may be applied on the multiple units or on the single units from a solution and/or suspension preferably in an aqueous solvent, but an organic coating composition may also be applied. The modified release coating may also be applied as a compression coating comprising a dry mixture of polymer(s) and the e.g. the active drug substance.

Examples of matrix-forming agents are hydroxypropylmethylcellulose such as, e.g., 1828, 2208, 2906 or 2910 according to USP, hydroxypropylcellulose, micronised ethylcellulose, low-substituted hydroxypropylcellulose (LH 20, 21, 31).

Examples of film-forming agents which are suitable for use in accordance with the present invention are agents selected from the group consisting of cellulose derivatives such as, e.g., ethylcellulose, cellulose acetate, cellulose propionate, cellulose butyrate, cellulose valerate, cellulose acetate propionate; acrylic polymers such as, e.g., polymethyl methacrylate; vinyl polymers such as, e.g., polyvinyl acetate, polyvinyl formal, polyvinyl butyryl, vinyl chloride-vinyl acetate copolymer, ethylene-vinyl acetate copolymer, vinyl chloride-propylene-vinyl acetate copolymer; silicon polymers such as, e.g., ladder polymer of sesquiphenyl siloxane, and colloidal silica; polycarbonate: polystyrene; polyester; cournarone-indene polymer; polybutadiene; and other high molecular synthetic polymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic coating is an acrylic resin lacquer used in the form of an aqueous dispersion, such as that which is commercially available from Rohm Pharma under the tradename Eudragit®. In further preferred embodiments, the acrylic coating comprises a mixture of two acrylic resin lacquers commercially available from Rohm Pharma under the tradenames Eudragit® RL 30 D and Eudragit® RS 30 D, re-spectively. Eudragit® RL 30 D and Eudragit® RS 30 D are copolymers of acrylic and methacrylic esters with a low content of quaternary ammonium groups, the molar ratio of ammonium groups to the remaining neutral (meth)acrylic esters being 1:20 in Eudragit® RL 30 D and 1:40 in Eudragit® RS 30 D. Eudragit® RL/RS mixtures are insoluble in water and in digestive fluids. However, coatings formed from the same are swellable and permeable in aqueous solutions and digestive fluids, The Eudragit® RL/RS dispersions may be mixed together in any desired ratio in order to ultimately obtain a modified release formulation having a desirable dissolution profile. The most desirable modified release formulations may be obtained from a retardant coating based on Eudragit® NE 30D, which is a neutral resin having a molecular weight of 800,000.

Examples of enteric polymers are cellulose acetate phthalate, cellulose acetate trimellitate, hydroxy propyl methyl cellulose acetate phthalate, hydroxy propyl methyl cellulose acetate succinate, carboxy methyl ethyl cellulose, polyvinyl acetate phthalate, copolymer of vinyl acetate and crotonic acid and poly(methacrylic acid, ethacrylate), and Eudragit® S 12.5, Eudragit® 100, Eudragit® FS 30D (all from Röhm) Sureteric® (from Colorcom), Aquateric® (from FMC) or HPMCP (from Shin-Etsu).

The amount of coating applied is adapted so as to obtain a predetermined dissolution characteristic of the composition However, the amount of coating applied should also be adapted so that there will be no rupturing problems.

The coating may be admixed with various excipients such as plasticizers, anti-adhesives such as, e.g., colloidal silicium dioxide, inert fillers, lipophilic agents such as, e.g. stearic acid, capric acid or hydrogenated castor oil, colon targeting excipients such as, e.g. amylose, ethylcellulose, Eudragit S 12.5 etc., and pigments in a manner known per se.

Tackiness of the water-dispersible film-forming substances may be overcome by simply incorporating an anti-adhesive in the coating. The anti-adhesive is preferably a finely divided, substantially insoluble, pharmaceutically acceptable non-weting powder having anti-adhesive properties in the coating. Examples of anti-adhesives are metallic stearates such as magnesium stearate or calcium stearate, microcrystalline cellulose, or mineral substances such as calcite, substantially water-insoluble calcium phosphates or substantially water-insoluble calcium sulphates, colloidal silica, titanium dioxide, barium sulphates, hydrogenated aluminium silicates, hydrous aluminium potassium silicates and talc. The preferred anti-adhesive is talc. The anti-adhesive or mixture of anti-adhesives is preferably incorporated in the coating in an amount of about 0.1–70% by weight, in particular about 1–60% by weight, and preferably about 50% by weight of the film layer. By selecting a small particle size of the talc, a larger surface area is obtained; the consequent higher anti-adhesive effect makes it possible to incorporate smaller amounts of specific anti-adhesives.

The units may further comprise an outer film layer.

In one aspect, the outer second layer comprises a water-based film-forming agent which prevents adhesion between the units at elevated temperatures and imparts flowability to the units, the water-based film-forming agent being anti-adhesive at temperatures above about 40° C., especially temperatures above abut 50° C., such as a temperature between about 60° C. and about 120° C., and being selected from diffusion coating materials such as ethylcellulose or enteric coating materials such as anionic poly(meth)acrylic acid esters, hydroxypropylmethylcellulosephthalate, celluloseacetatephthalate, polyvinyl-acetatephthalate, polyvinylacetatephthalate-crotonic acid copolymerisates, or mixtures hereof, or water-soluble coating materials such as water-soluble cellulose derivatives, e.g. hydroxypropylcellulose, carboxymethylcellulose, methylcellulose, propylcellulose, hydroxyethylcellulose, carboxyethylcellulose, carboxymethylhydroxyethylcellulose, hydroxymethylcellulose, carboxymethylethylcellulose, methylhydroxypropylcellulose or hydroxypropylmethylcellulose.

Examples of plasticizers for use in accordance with the present invention include triacetin, acetylated monoglyceride, rape oil, olive oil, sesame oil, acetyl trbutyl citrate, acetyl triethyl citrate, glycerin, sorbitol, diethyloxalate, diethylmalate, diethylmaleate, diethylfumarate, diethylsuccinate, diethylmalonate, dioctylphthalate, dibutylsebacetate, triethylcitrate, tributylcitrate, glyceroltributyrate, polyethyleneglycol, propyleneglycol, 1,2-propyleneglycol, dibutylsebacate, diethylsebacate and mixtures thereof. The plasticizer is normally incorporated in an amount of less than 20% by weight, calculated on the dry matter content of the coating composition.

The fast onset composition of a kit according to the invention may be any composition well known in the art to provide a relative fast release.

With respect to nasal vehicles, polyethyleneglycols is especially preferred such as more n-ethylene glycols represented by the following formula $$H(OCH_2CH_2)_pOH$$

wherein p is an integer in the range of 1 to 14. Examples of n-ethylene glycols are monoethylene glycol (1EG), di ethylene glycol (2EG), triethylene glycol (3EG), tetraethylene glycol (4EG), penta ethylene glycol (5EG), hexaethylene glycol (6EG), heptaethylene glycol (7EG), octaethylene glycol (8EG), nonaethylene glycol (9EG), decaethylene glycol (10EG), undecaethylene glycol (11EG), dodecaethylene glycol (12EG), tridecaethylene glycol (13EG), and tetradecaethylene glycol (14EG). The ethylene glycols may be used in the form of the single compounds or as a mixture of two or more n-ethylene glycols, e.g. commercial products such as polyethylene glycol 200 (PEG 200), polyethylene glycol 300 (PEG 300) or polyethylene glycol 400 (PEG 400). The polyethyleneglycols may be used in combination with glycofurols (α-[(tetrahydro-2-furany)methyl]-ω-hydroxy-poly(oxy-1,2-ethanediyl)). The latter may also be used separately.

The volume of a nasal dosage is preferably within 500 μl such as within 300 μl such as in a range of 10–250 μl.

The invention is further illustrated in the drawing, wherein

Figure 1:
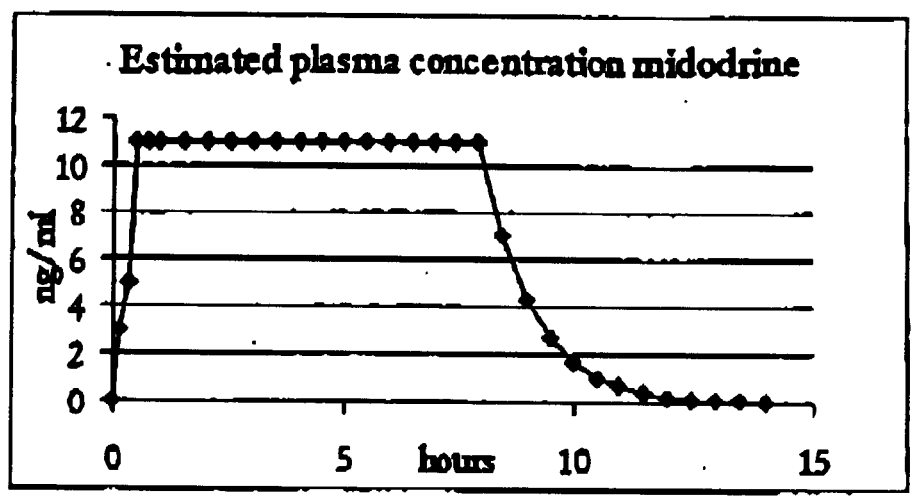
FIG. 1 shows the estimated plasma concentration of midodrine.
Figure 2:
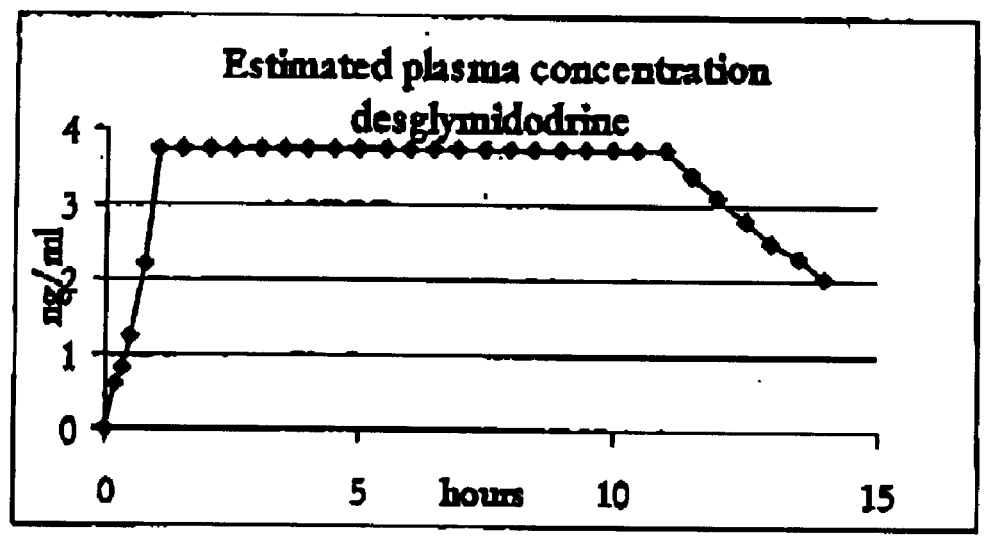
FIG. 2 shows the estimated plasma concentration of desglymidodrine.
Figure 3:
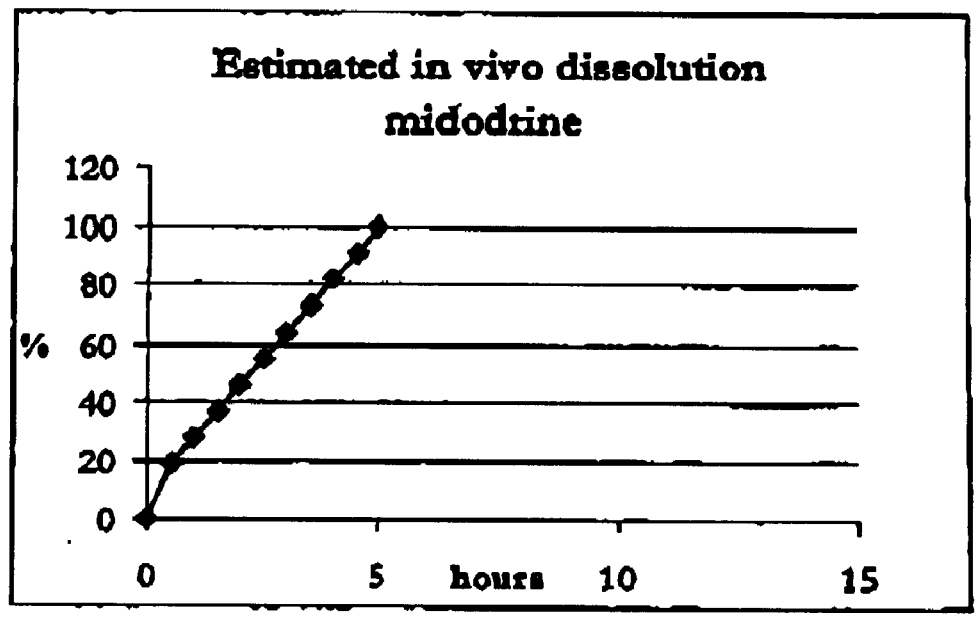
FIG. 3 shows the estimated in vivo dissolution of midodrine.
Figure 4:
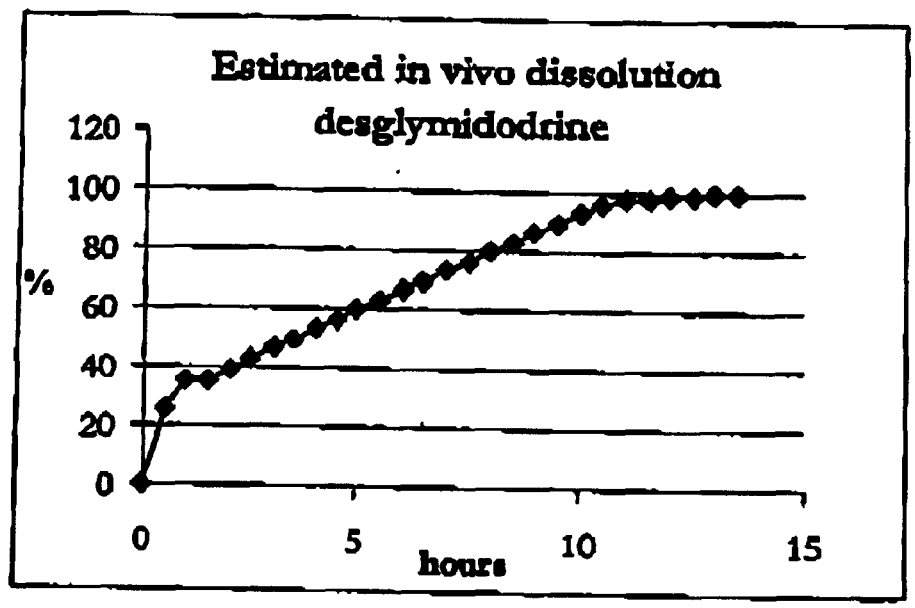
FIG. 4 shows the estimated in vivo dissolution of desglymidodrine.
Figure 5:
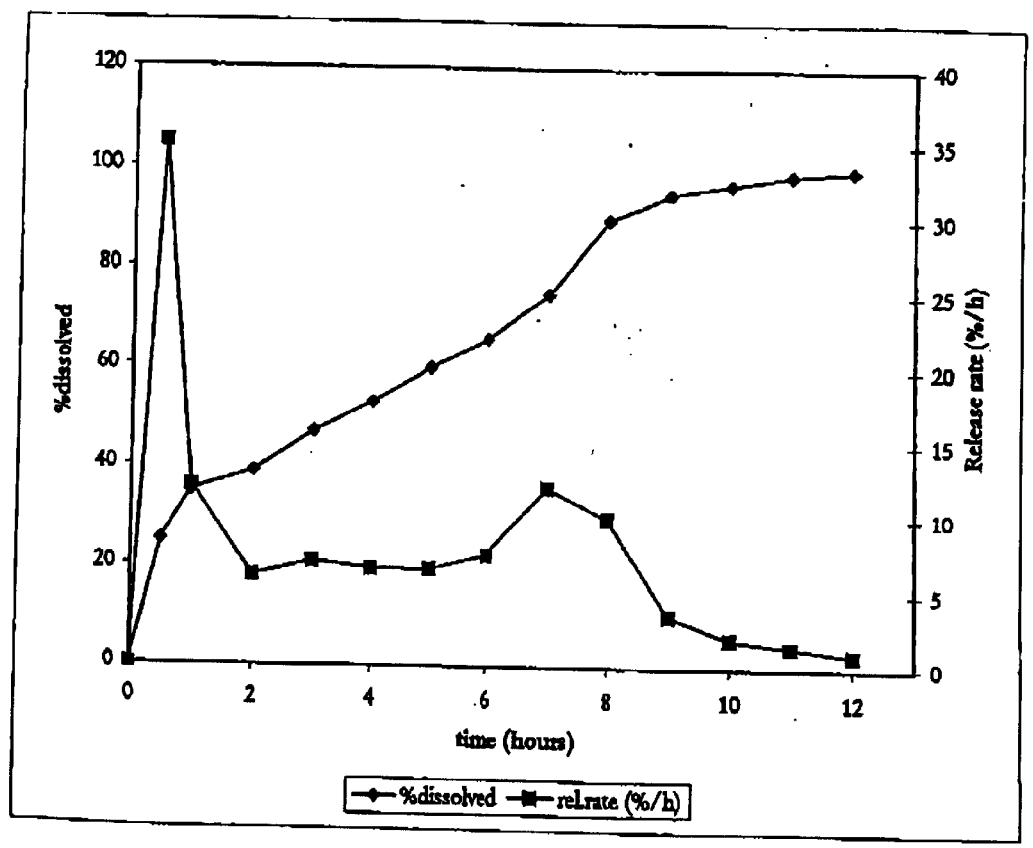
Figure 6:
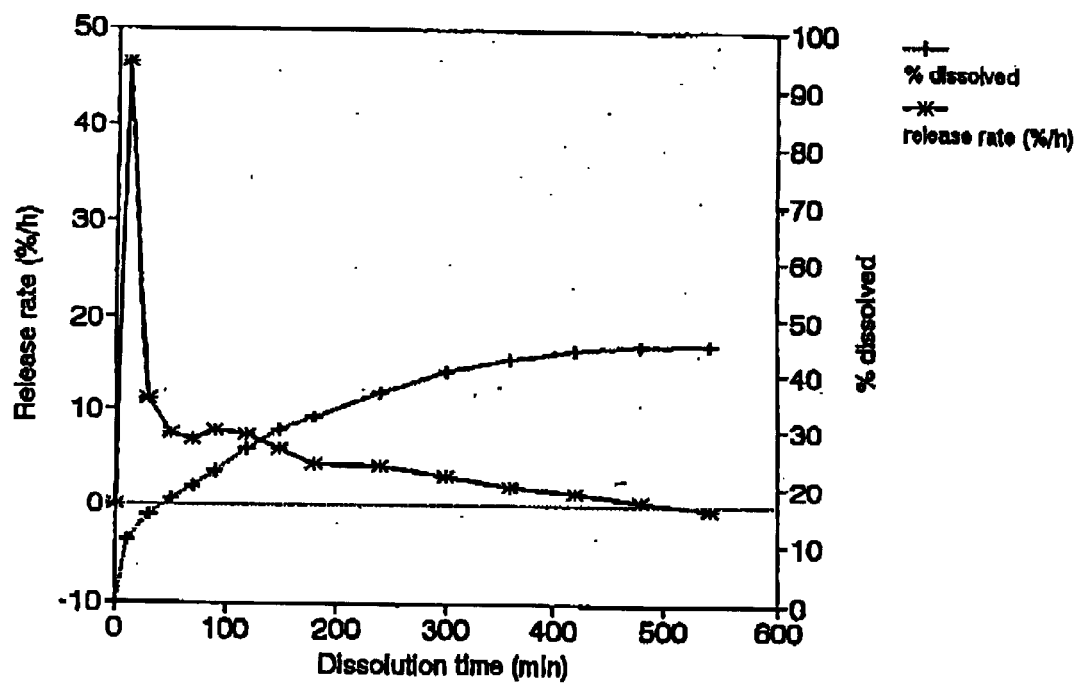
Figure 7:
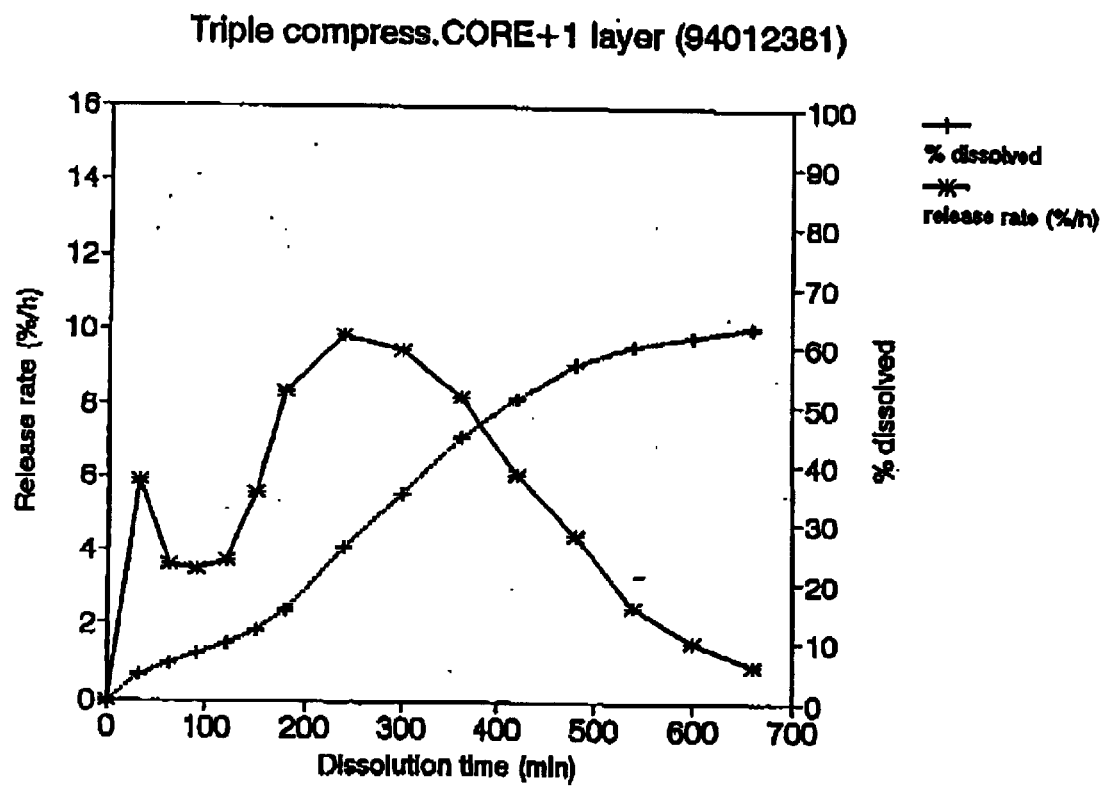
Figure 8:
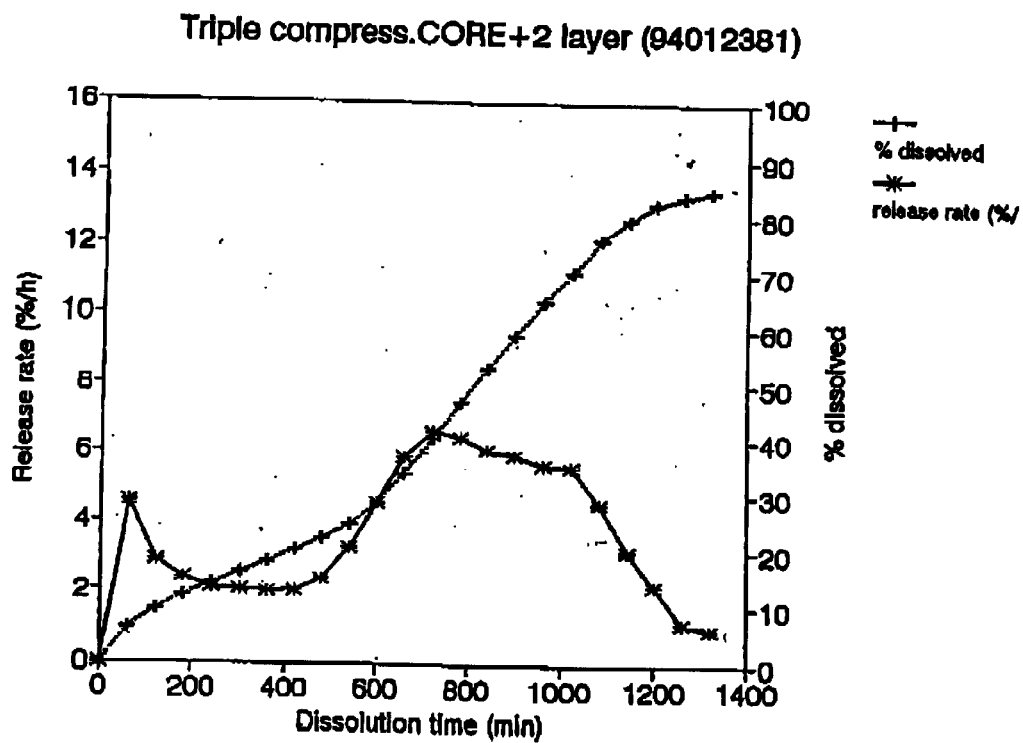
Figure 9:
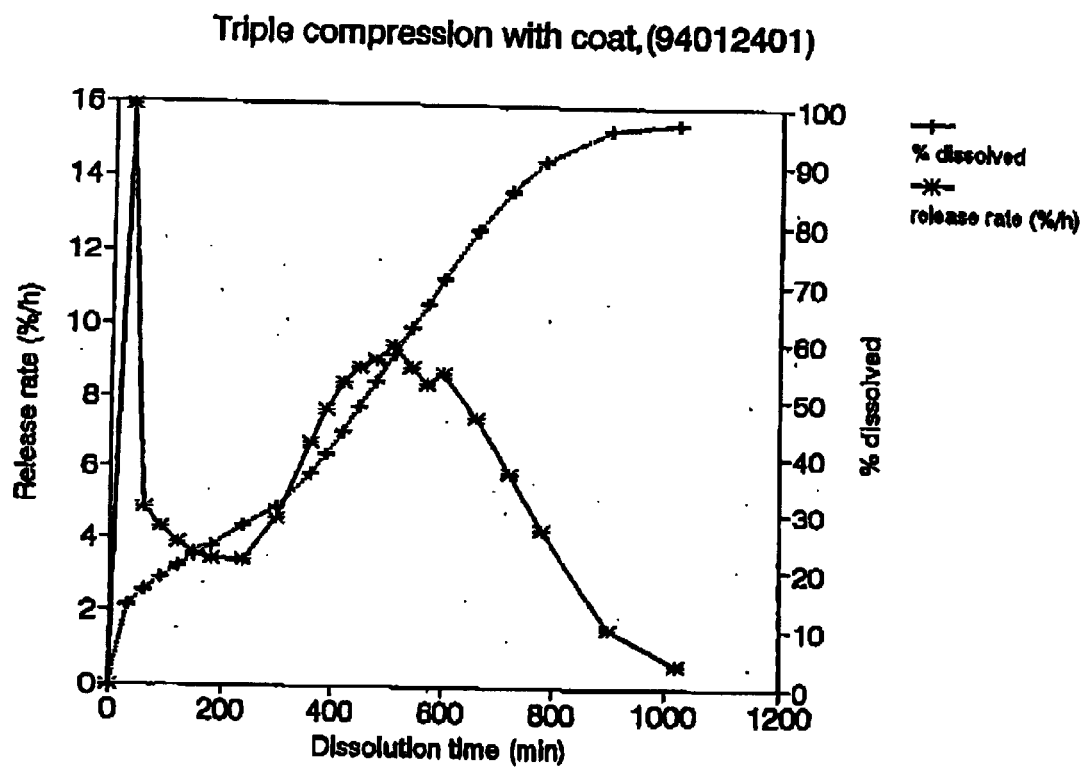
Figure 10:
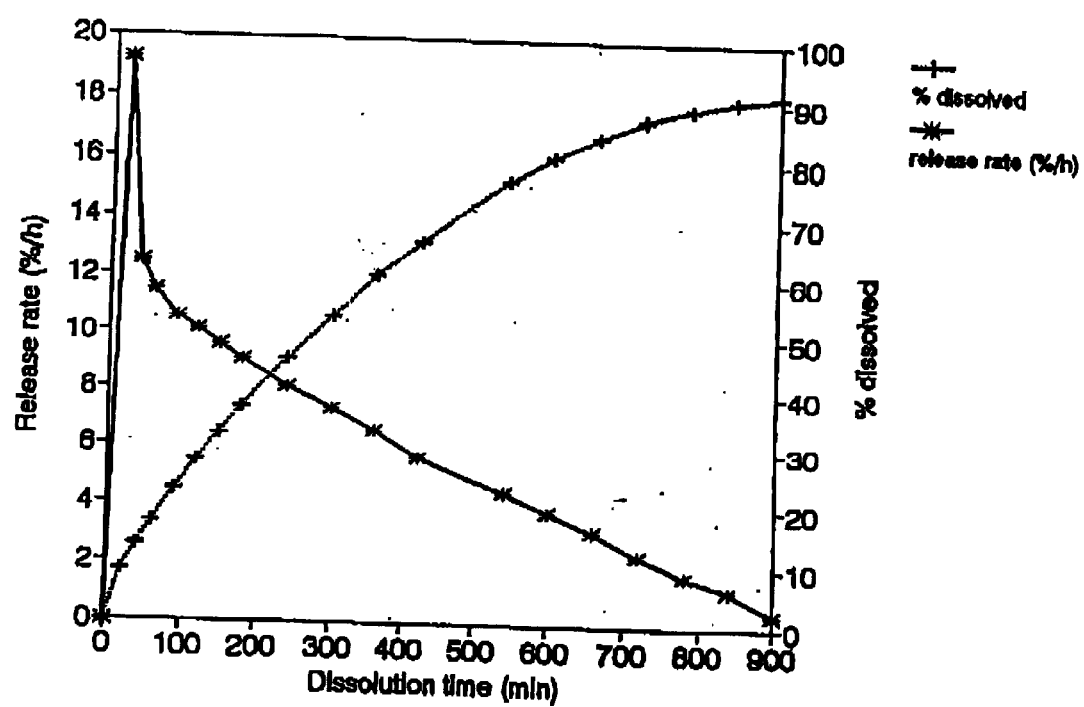
Figure 11:
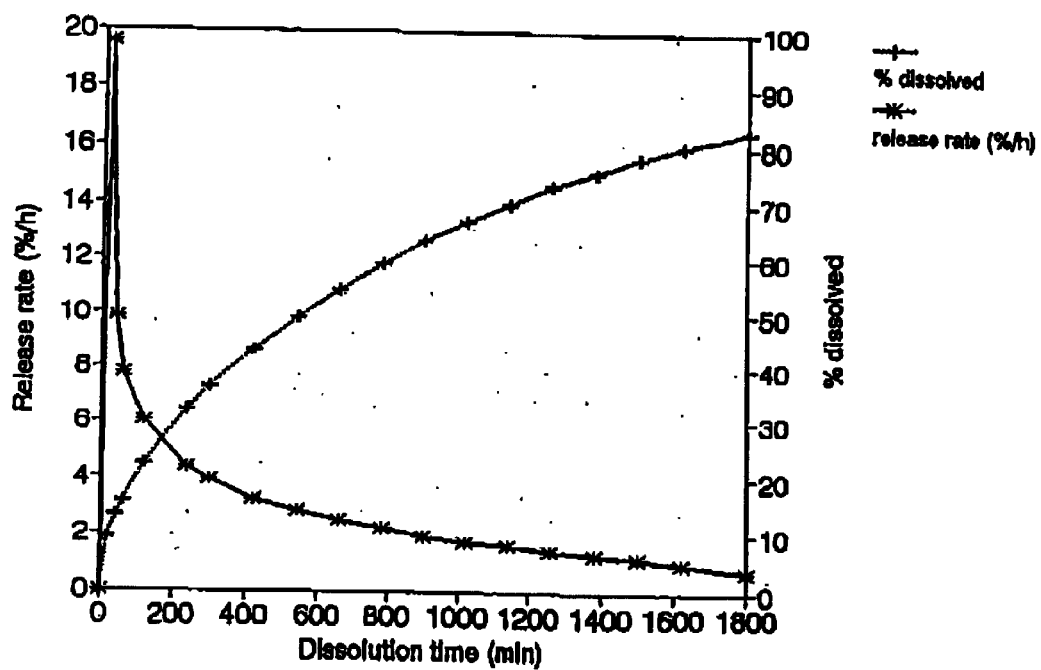
Figure 12:
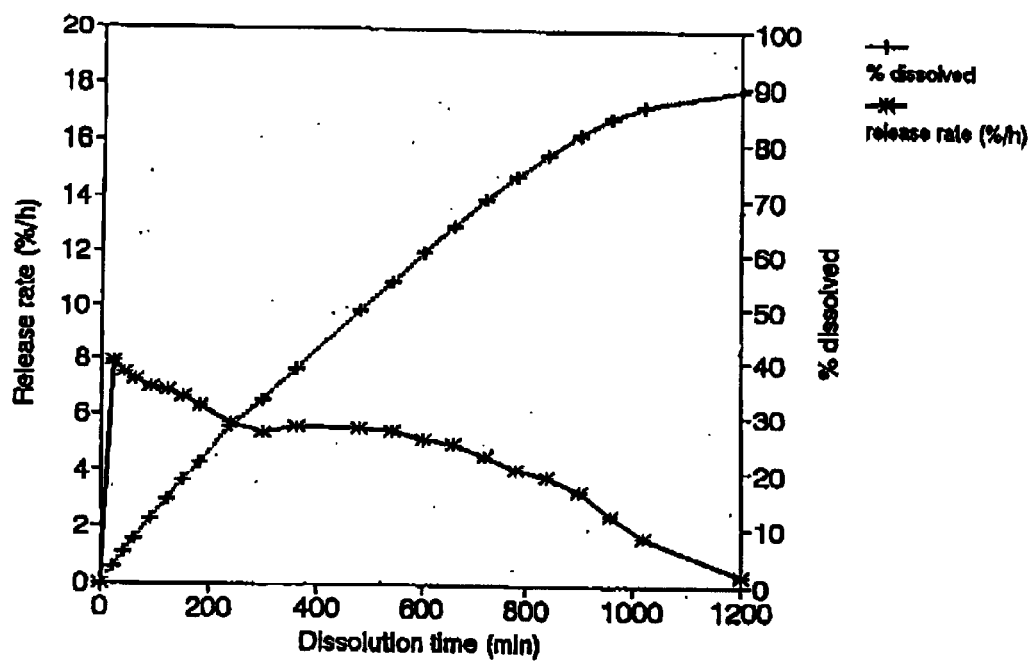
Figure 13:
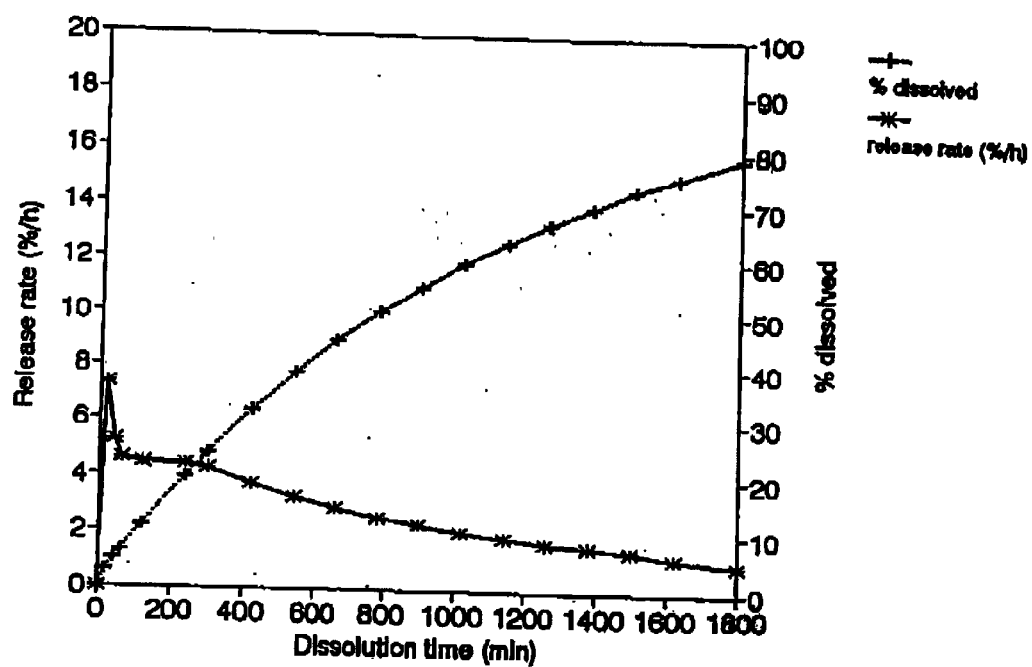
Figure 14:
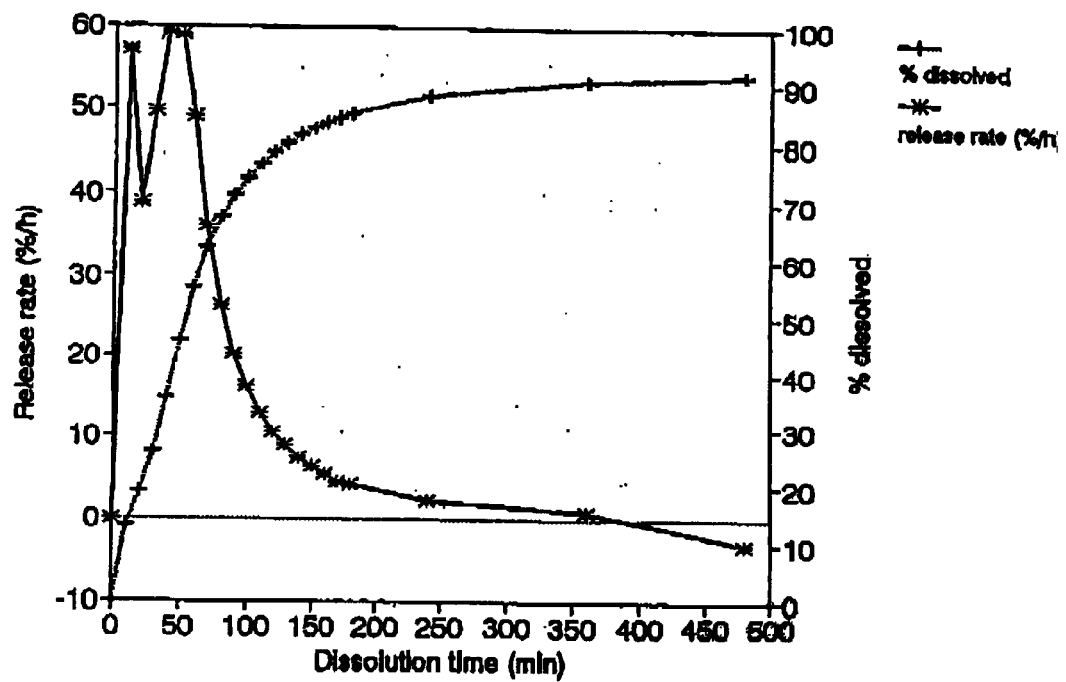
Figure 15:
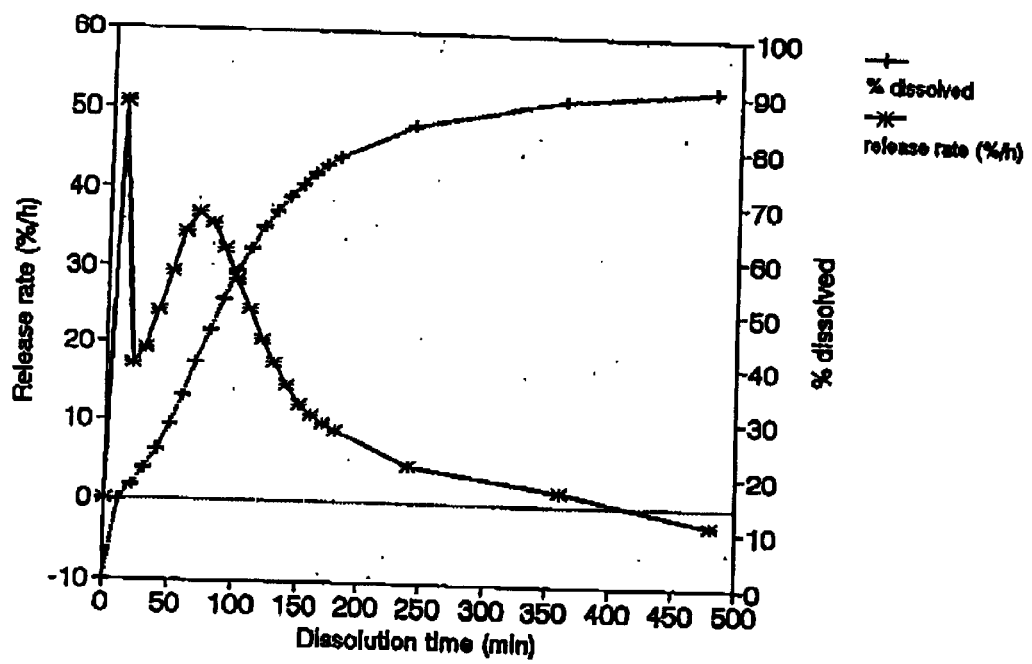
Figure 16:
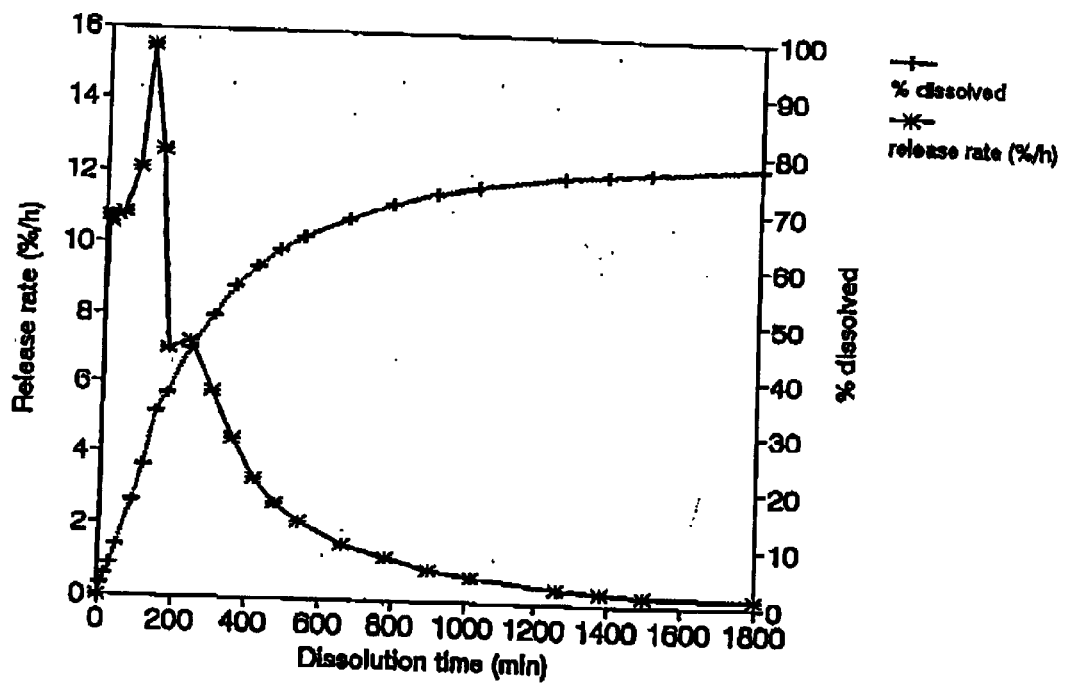
Figure 17:
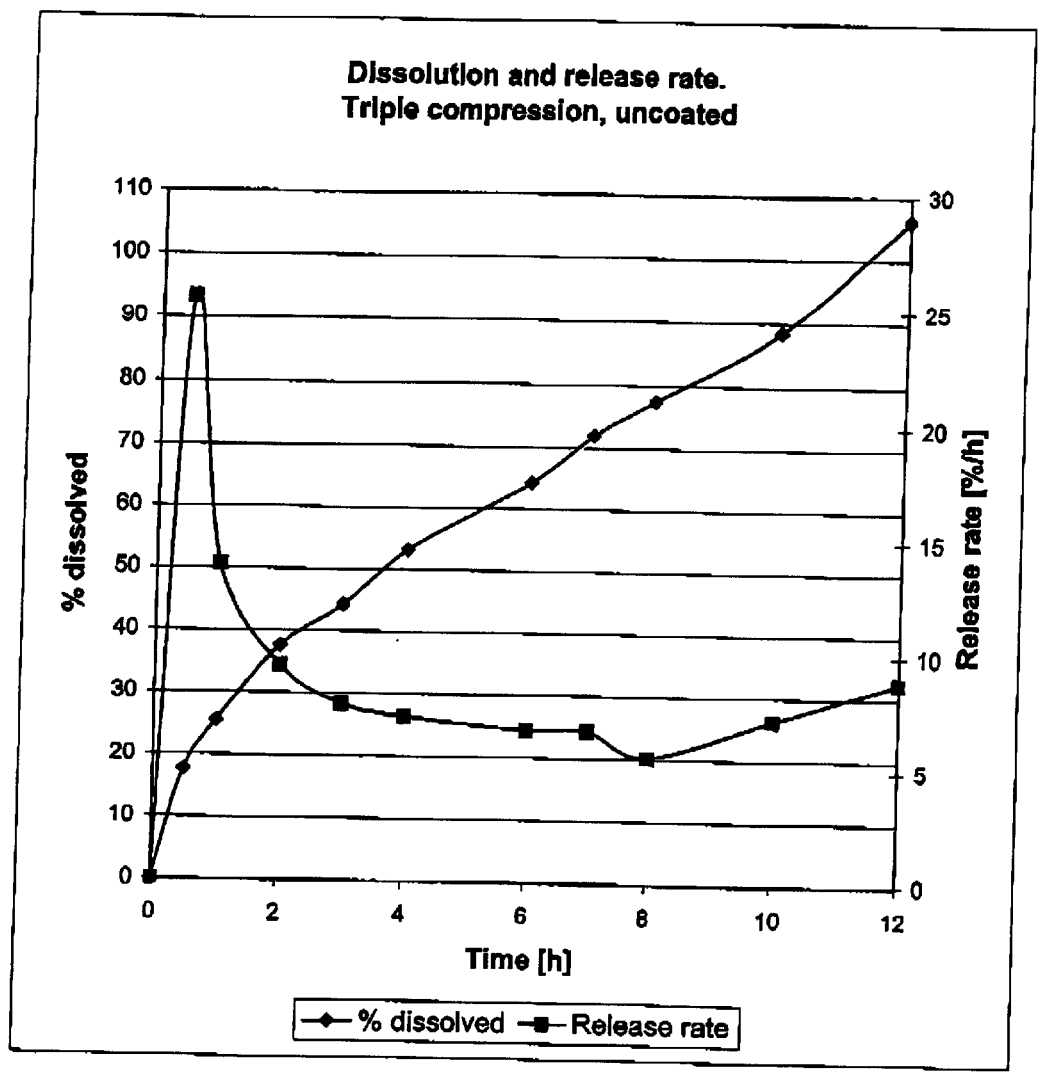
Figure 18:
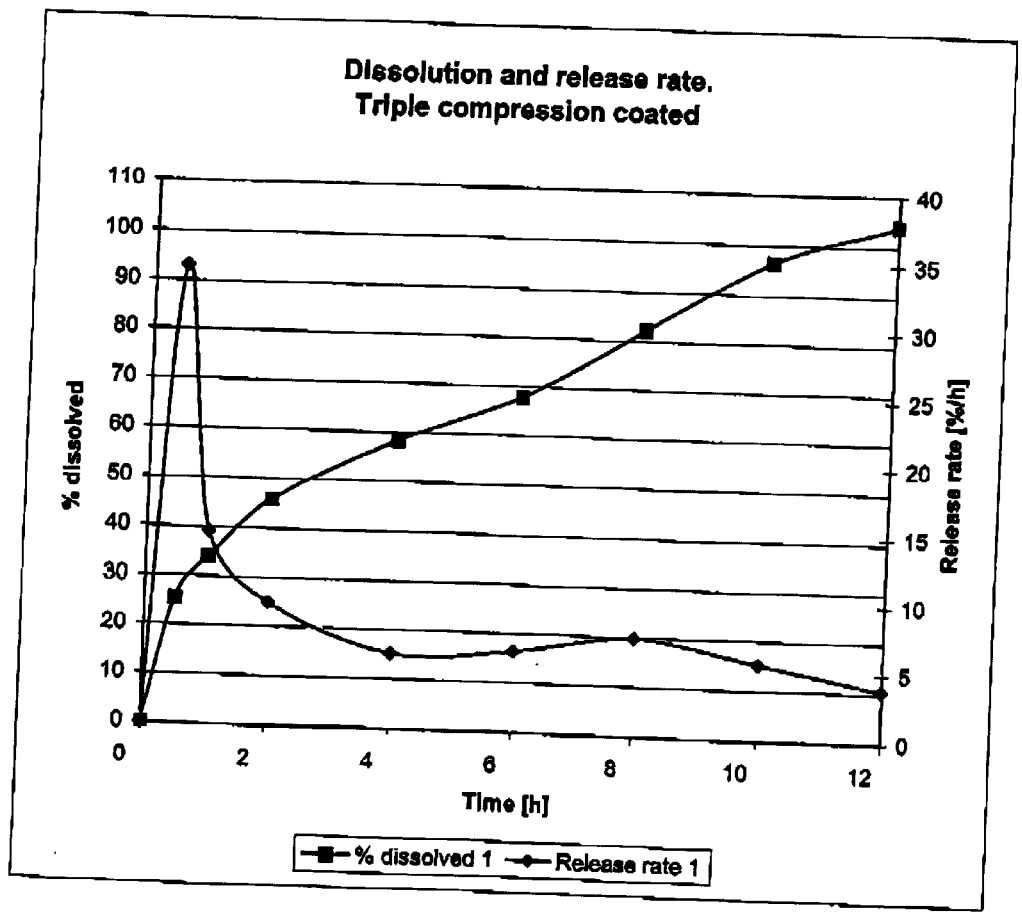
Figure 19:
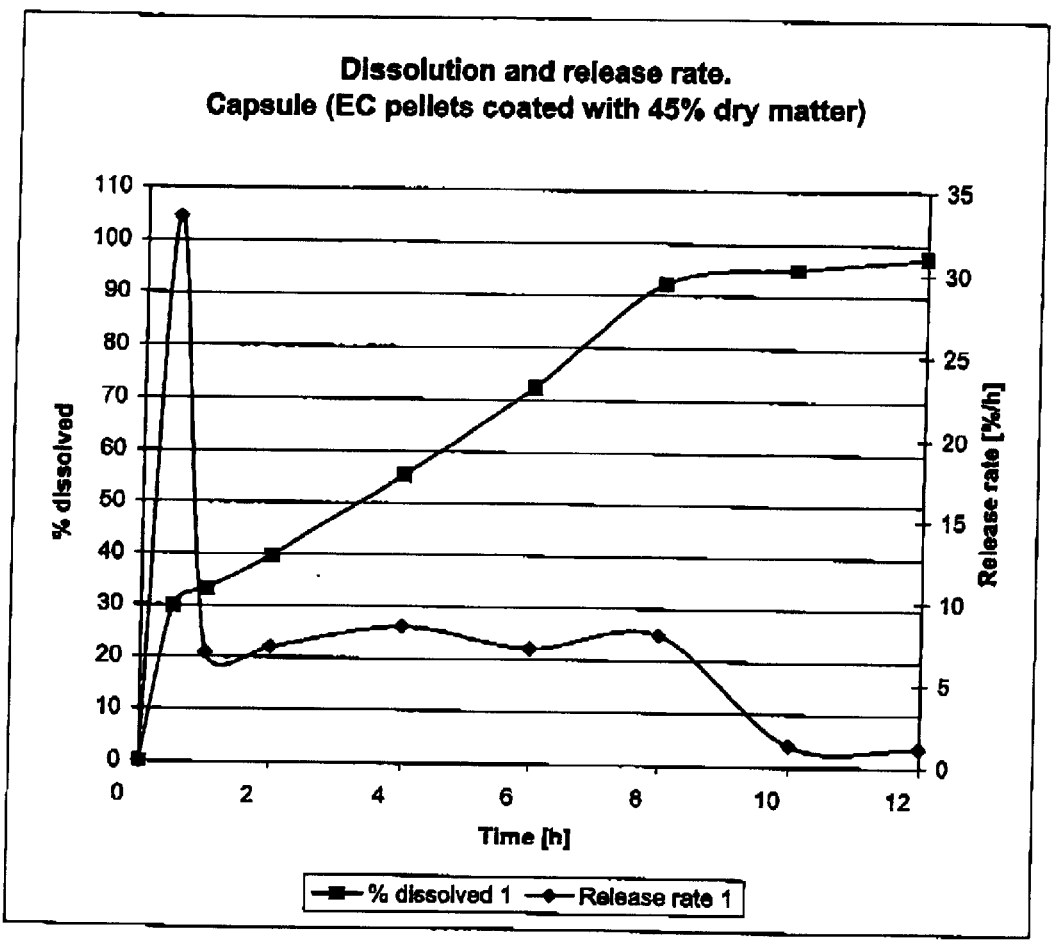
Figure 20:
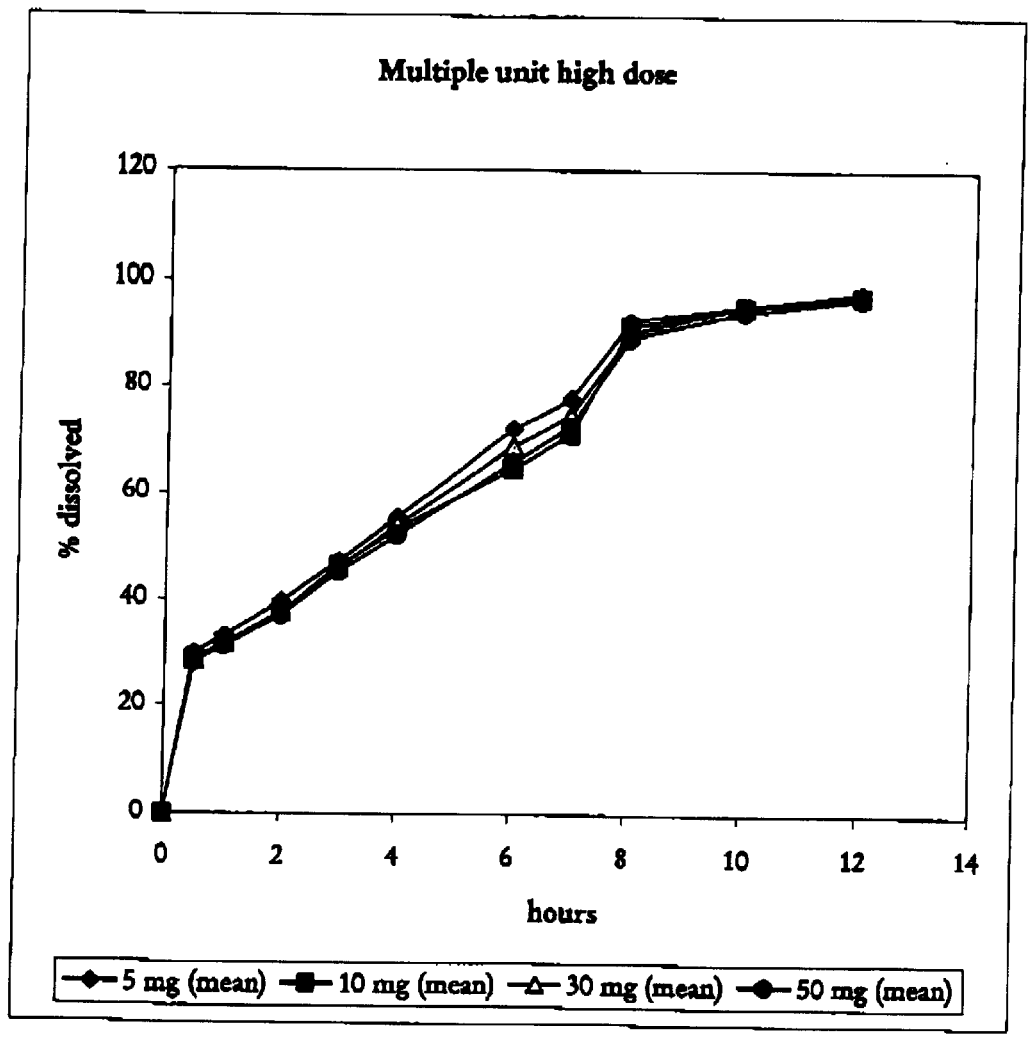
Figure 21:
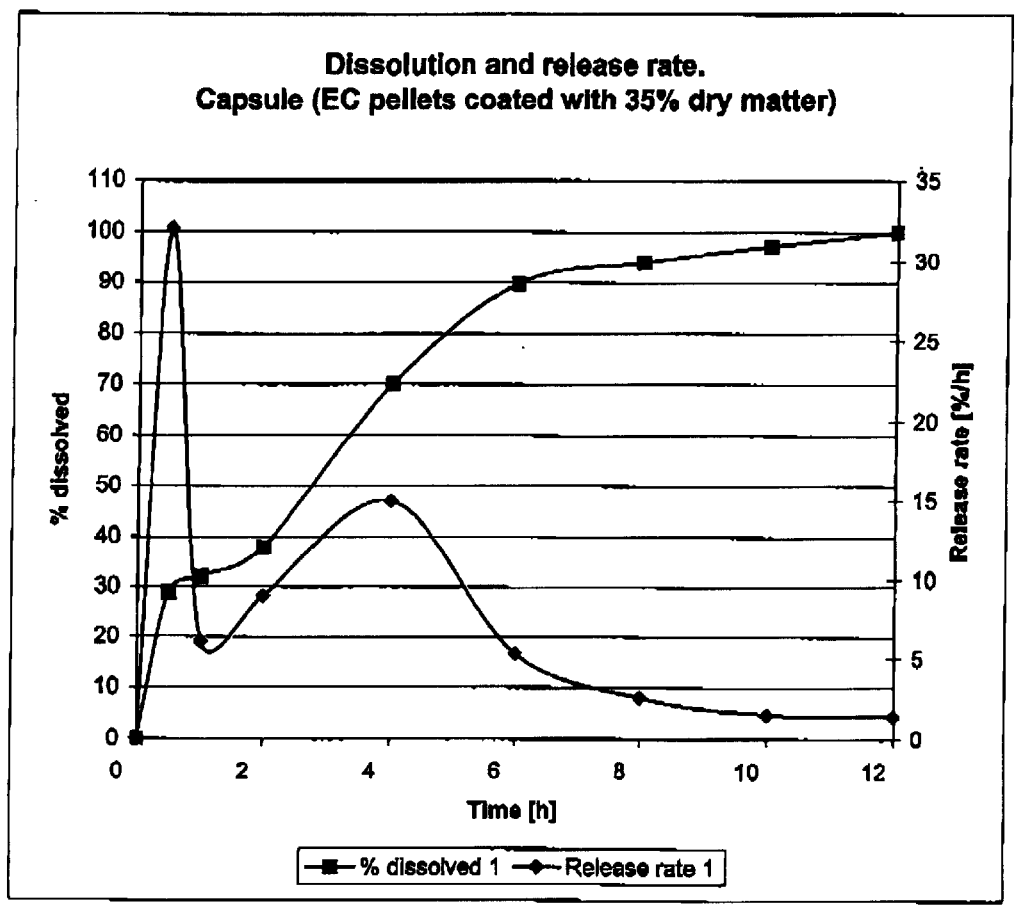
Figure 22:
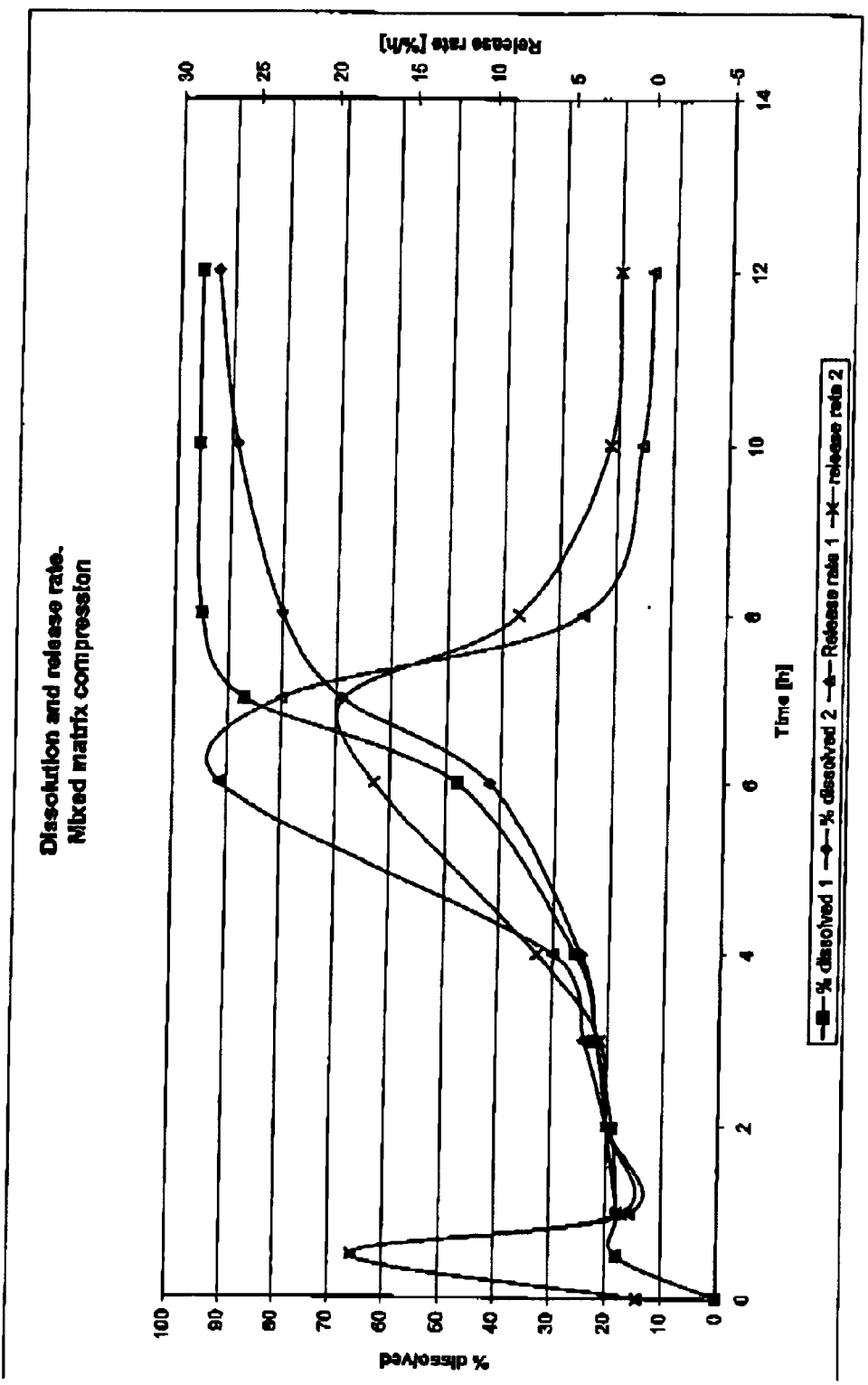
Figure 23:
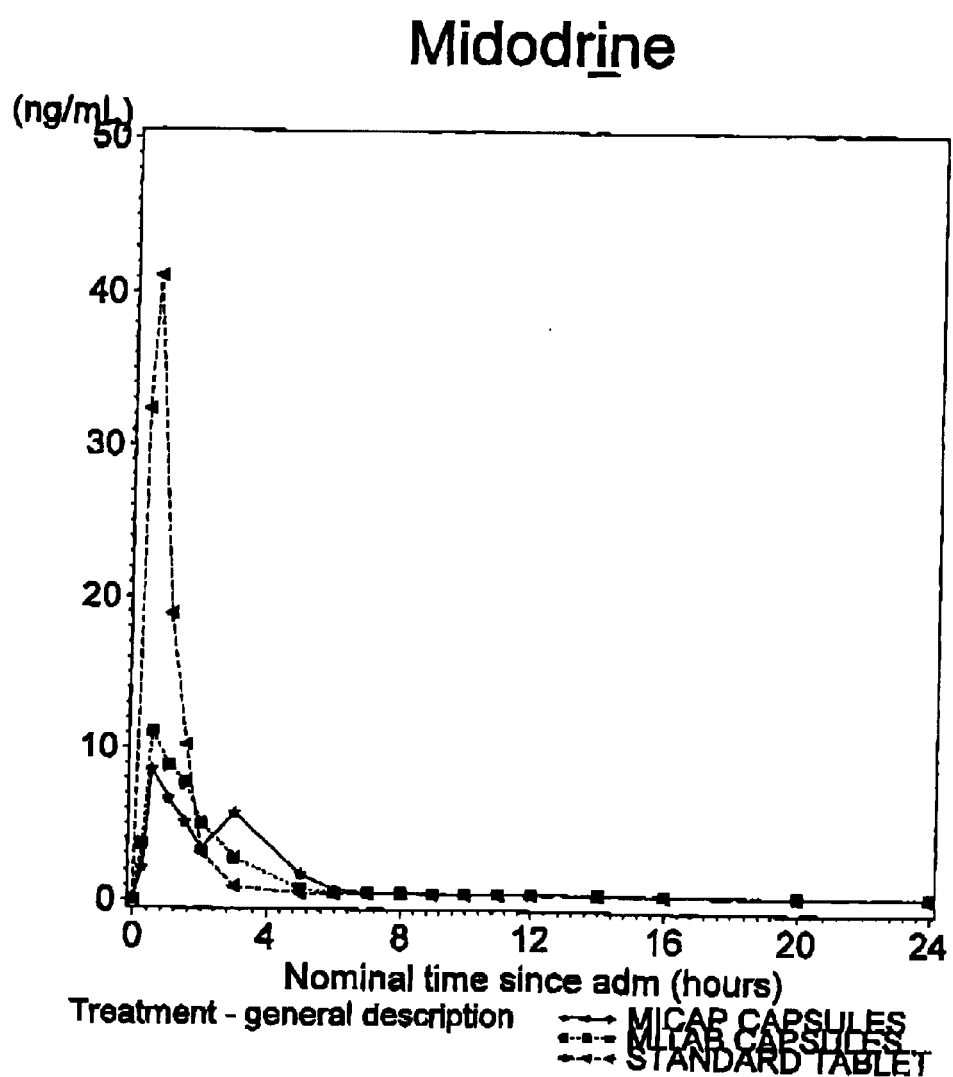
Figure 24:
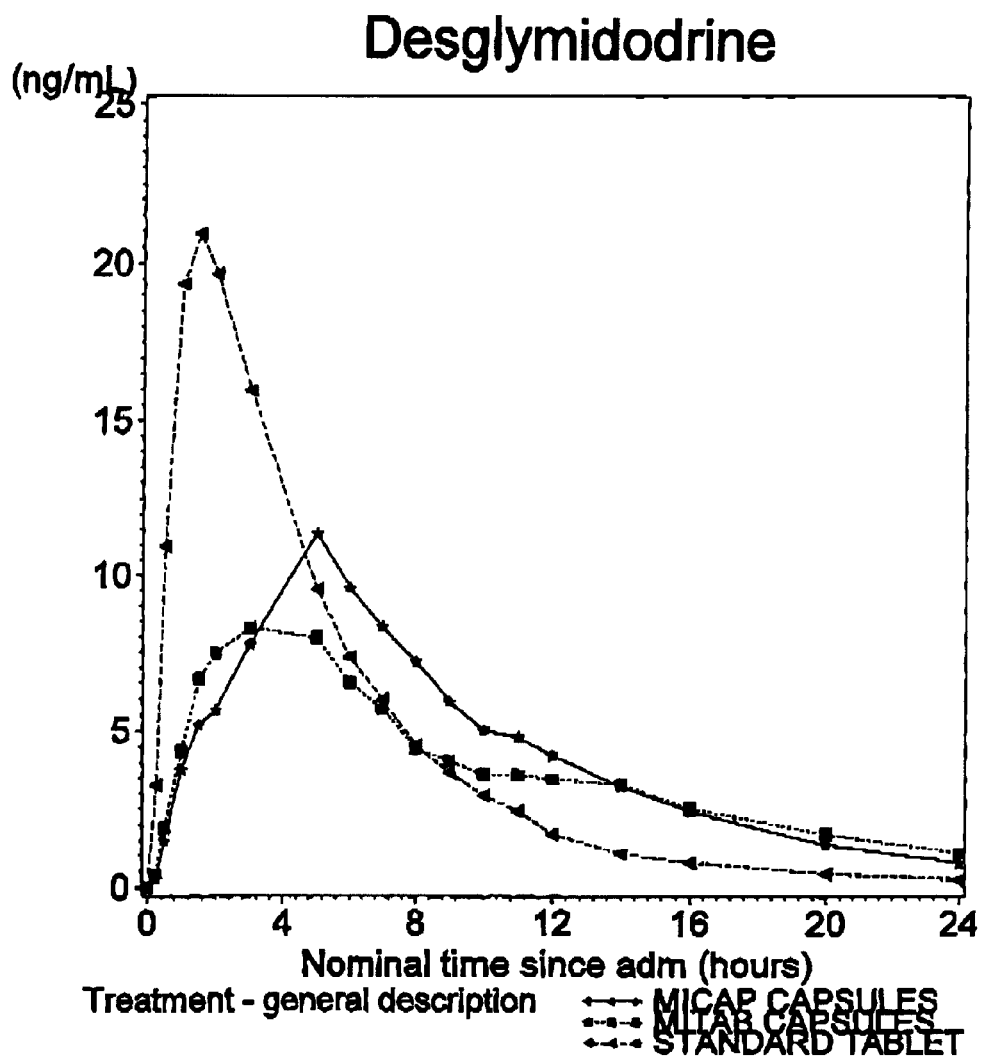

FIG. 5 shows the estimated in vitro target for dissolution of midodrine and the estimated release rate, FIGS. 6–9 illustrate the results of Example 1, FIGS. 10–13 illustrate the results of Example 3, FIGS. 14–16 illustrate the results of Example 4, FIGS. 17–18 illustrate the results of Example 2, FIGS. 19 and 20 the results of Example 12, FIG. 21 illustrates the results of Example 13, FIG. 22 illustrates the result of Example 14, and FIGS. 23–24 illustrate the results of Example 15.

The following examples are intended to illustrate specific embodiments of the present invention but are not intended in any way to limit the invention. Some of the examples are included in order to illustrate that the release rate and dissolution characteristics of a composition can be changed by varying a number of formulation parameters.

Methods

| DISSOLUTION METHOD I FOR MITAB (midodrine hydrochloride triple compression tablets). | |
|---|---|
| Apparatus | Ph. Eur/USP dissolution apparatus + Perkin Elmer fully automatic dissolution system + Disslab PC-programme |
| Glass fibre filter | 0.7 μm |
| Dissolution medium | 600 ml 0.1N HCl |
| Rotation speed | 100 rpm |
| Stirrer | Basket |
| Sampling times | As appear from tables |
| Detection wavelength | 290 nm |
| Measuring equipment | UV-spectrophotometer, 10 mm quartz cuvette |
| Temperature of dissolution medium | 37° C. ± 0.5° C. |

Reagents 0.1N HCl is prepared by dilution of concentrated HCl (37%) with purified water.

Standards

Two solutions are prepared with a concentration of 10 μl/ml midodrine hydrochloride in 0.1 N HCl. 0.1 N HCl is used as blind. The absorbances of the solutions are measured on the spectrophotometer. $E_{1\%/cm}$ is calculated. $E_{1\%/cm}$ =A×1000, where 1000 is due to the fact, that the solution is only 0.001%. The mean value of the to measurements is inserted in the software programme in accordance with the manual for the automated dissolution system.

Performance 600 ml 0.1N HCl is filled in each of the six vessels in the dissolution equipment. The media is heated to a temperature of 37° C.±0.5° C. One weighed tablet is placed in each of the six baskets. The stirring is started as soon as the baskets are lowered into the vessels. The sample is filtered through a 0.7 µm filter. The absorbances of the filtered samples are measured directly at 290 nm.

DISSOLUTION METHOD II FOR MITAB
(midodrine hydrochloride triple compression tablets). HPLC-detection.
The dissolution parameters are described in Method I.
The measurement is performed by HPLC.

| Column | Spherisorb ODS-1; 5 µm; 25 cm; ID 4.6 µm |
|---|---|
| Injection volume | 20 µl |
| Flowrate | 1.0 ml/min |
| Mobile phase | Phosphate buffer pH 3; methanol 77:23 (v/v) |
| Detection | 290 nm |
| Runtime | 30 min |

Reagents for dissolution are described in Method I.

Buffer solution pH 3 is prepared by dissolving 23.6 g potassium dihydrogen phosphate in 900 ml purified water. o-Phosphoric acid 85% is used to adjust pH. The flask is filled to 1 l.

Standards

Two stock solutions with a concentration of midodrine hydrochloride 120 µg/ml in 0.01 N HCl are prepared. The solutions are stored in refrigerator.

Prepare from each stock solution two standard solutions with a concentration of midodrine hydrochloride approximately 1.5 µg/ml and 15 µg/ml respectively, diluted with 0.01 N HCl. Desglymidodrine hydrochloride is quantified against the standard curve of midodrine hydrochloride. The relative response factor is 1.25 for Desglymidodrine hydrochloride to midodrine hydrochloride.

Performance

The dissolution is performed as described in Method I. The sample is withdrawn with a pipette and transferred to a syringe. The sample is filtered through a 0.7 µm filter. The first ml is returned to the vessel in order to reduce deviation from the desired volume. A sample of approximately 1.5–2 ml is transferred to the vial, the rest is returned to the vessel. The absorbances of the filtered samples are measured as described.

Calculations

A standard curve is calculated by linear regression, using the standard solutions. The peak area of the sample is the sum of the peak area of Midodrine Hydrochloride and the peak area of Desglymidodrine hydrochloride, where the latter is divided by the relative response factor 1.25.

The results are calculated as % released at any time and presented as a mean value of the six samples together with min and max.

$$\% \text{ dissolved} \frac{A \, vol \, 100}{bx}$$

Where

A sum of peak area of midodrine hydrochloride and Desglymidodrine hydrochloride
(corr.)
Vol 600 ml for tablets (MITAB)
100%
b slope of the calibration curve (A/mg/ml)
x declared amount (mg)

DISSOLUTION METHOD III FOR MICAP
(midodrine hydrochloride multiple unit capsules).

| Apparatus | Ph. Eur/USP dissolution apparatus + Perkin Elmer fully automatic dissolution system + Disslab PC-programme |
|---|---|
| Glass fibre filter | 0.7 µm |
| Dissolution medium at the beginning | 600 ml 0.1N HCl |
| Dissolution media at change to pH 6.0 | Addition of 130 ml 0.23 M Na$_3$PO$_4$ solution |
| Dissolution media at change to pH 7.5 | Addition of further 70 ml 0.23 M Na$_3$PO$_4$ solution |
| Time for change to pH 6.0 | 2 hours (120 min) |
| Time for change to pH 7.5 | 7.5 hours (450 min) |
| Rotation speed | 100 rpm |
| Stirrer | Basket |
| Sampling times | As appear from tables |
| Detection wavelength | 290 nm |
| Measuring equipment | UV-spectrophotometer, 10 mm quartz cuvette |
| Temperature of dissolution medium | 37° C. ± 0.5° C. |
| Reference (vessel no 7) | An empty capsule dissolved in 600 ml 0.1N HCl |

Vessel no 7 is added Na$_3$PO$_4$ solution in parallel with the six sample vessels Reagents 0.1 N HCl is prepared by dilution of concentrated HCl (37%) with purified water. 0.23 M Na$_3$PO$_4$ solution: Dissolve an amount of Na$_3$PO$_4$.12H$_2$O in a bit of 1M HCl-R and add water to a concentration of 0.23 M. (Strong alkaline).

Buffer solution pH 6.0:600 ml 0.1 N HCl is added 130 ml 0.23 M Na$_3$PO solution. Buffer solution pH 7.5: Buffer solution pH 6.0 is added further 70 ml 0.23 M Na$_3$PO solution.

Standards

Two solutions are prepared with a concentration of 10 µg/ml midodrine hydrochloride in 0.1 N HCl. 0.1 N HCl is used as blind. The absorbances of the solutions are measured on the spectrophotometer.

$E_{1\%/cm}$ is calculated. It has previously been determined, that the $E_{1\%/cm}$ is the same for the three media, so it is only necessary to perform the test in 0.1N HCl.

$E_{1\%/cm}$=A×1000, where 1000 is due to the fact, that the solution is only 0.001% The mean value of the to measurements is inserted in the software programme in accordance with the manual for the automated dissolution system.

Performance 600 ml 0.1N HCl is filled in each of the seven vessels in the dissolution equipment. The media is heated to a temperature of 37° C.±0.5° C. One weighed capsule is placed in each of the six baskets. In the seventh basket an empty capsule is placed. This is measured as a blank reference. The stirring is started as soon as the baskets are lowered into the vessels. The measured amounts of buffer solution, needed for the changes of pH in the vessels, are preheated to 37° C., before addition to the vessels. When the buffer is to be added, the baskets are elevated from the vessels, the buffer is added, the solution in the vessel is stirred to homogenise the solution and the baskets are lowered into the vessels again. The sample is filtered through a 0.7 µm filter. The absorbances of the filtered samples are measured directly at 290 nm.

| DISSOLUTION METHOD IV FOR MICAP |
|---|
| (midodrine hydrochloride multiple unit capsules). HPLC-detection. The dissolution parameters are described in Method III. The measurement is performed by HPLC. |

| | |
|---|---|
| Column | Spherisorb ODS-1; 5 µm; 25 cm; ID 4.6 µm |
| Injection volume | 20 µl |
| Flowrate | 1.0 ml/min |
| Mobile phase | Phosphate buffer pH 3; methanol 77:23 (v/v) |
| Detection | 290 nm |
| Runtime | 30 min |

Reagents for dissolution are described in Method III.

Buffer solution pH 3 is prepared by dissolving 23.6 g potassium dihydrogen phosphate in 900 ml purified water. o-Phosphoric acid 85% is used to adjust pH. The flask is filled to 1 l.

Standards

Two stock solutions with a concentration of midodrine hydrochloride 120 µg/ml in 0.01N HCl are prepared. The solutions should be stored in refrigerator.

Prepare from each stock solution two standard solutions with a concentration of midodrine hydrochloride approximately 1.5 µg/ml and 15 µg/ml respectively, diluted with 0.01N HCl. Desglymidodrine hydrochloride is quantified against the standard curve of midodrine hydrochloride. The relative response factor is 1.25 for desglymidodrine hydrochloride to midodrine hydrochloride.

Performance

The dissolution is performed as described in Method III. The sample is withdrawn with a pipette, transferred to a syringe. The sample is filtered through a 0.7 µm filter. The first ml is returned to the vessel in order to reduce deviation from the desired volume. A sample of approximately 1.5–2 ml is transferred to the vial, the rest is returned to the vessel. The absorbances of the filtered samples are measured as described.

Calculations

A standard curve is calculated by linear regression, using the standard solutions. The peak area of the sample is the sum of the peak area of midodrine hydrochloride and the peak area of desglymidodrine hydrochloride, where the latter is divided by the relative response factor 1.25.

The results are calculated as % released at any time and presented as a mean value of the six samples together with min and max.

$$\% \text{ dissolved} = \frac{A \, vol \, 100}{bx}$$

Where

A sum of peak area of midodrine hydrochloride and desglymidodrine hydrochloride (corr.)

Vol 600 ml for up to 2 hours 730 ml for up to 7.5 hours and 800 ml for up to 12 hours for capsules (MICAP)

100% b slope of the calibration curve (A/mg/ml)

x declared amount (mg)

Dissolution Method V. Dissolution Method Used for Midodrine Melt Tablets

Dissolution apparatus 2 according to USP and Ph. Eur.

Paddle method

Rotations: 50 rpm

Temperature: 37° C.

Dissolution medium, isotonic buffer pH 6.8 or purified water

Volumen: 600 ml

Sample time: 5 min

RP-HPLC: Phosphate buffer pH 3: methanol 77:23 (v/v)

Detection at 290 nm.

Dissolution Method VI for Midodrine Sublingual Tablets

Dissolution apparatus 2 according to USP and Ph. Eur.

Paddle method

Rotations: 50 rpm

Temperature, 37° C.

Dissolution medium: isotonic buffer pH 6.8 or purified water

Volume: 600 ml

Sampling time: 5 min

RP-HPLC: Phosphate buffer pH 3: methanol 77:23 (v/v)

Detection at 290 nm.

EXAMPLES

Example 1

| Composition made by employment of triple compression A tablet was prepared from the following ingredients: | |
|---|---|
| Core: | |
| Midodrine hydrochloride | 5.0 mg |
| Klucel MF | 2.0 mg |
| Methocel E 50 | 93.0 mg |
| 1st compression layer: | |
| Midodrine hydrochloride | 1.5 mg |
| Klucel MF | 6.6 mg |
| Methocel E 15 | 156.9 mg |
| 2nd compression layer: | |
| Midodrine hydrochloride | 2.8 mg |
| Methocel E 50 | 247.2 mg |

Using the core composition a core weighing 100 mg was compressed using a punch 6 mm in diameter. The core was compression coated using 165 mg of the 1st compression layer composition and a punch of 9 mm in diameter. The thus compression coated core was compression coated again using 250 mg of the 2nd compression layer composition and a punch of 11 mm in diameter.

A composition comprising midodrine hydrochloride 1.2 mg, Methocel E5 9.7 mg and Talc 8.5 mg was applied to the tablet by spray coating.

The following results were obtained with respect to dissolution and release rate (the dissolution method employed throughout the examples and claims is in accordance with the method described in USP and Ph.Eur. method 2 (paddle) employing 0.1 N hydrochloric acid as dissolution medium, 500 ml of dissolution medium, 100 rpm, 37° C. and the amount of midodrine (and/or desglymidodrine) released was measured by UV at at wavelength of 213.4.

| | % w/w dissolved based on the total weight of the composition tested | | | |
|---|---|---|---|---|
| time (hours) | core | core + 1 layer | core + 2 layers | core + 2 layers and coated |
| 0.5 | 14.86 | 4.02 | | 13.30 |
| 1 | | 5.90 | 5.89 | 15.89 |
| 2 | 26.26 | 9.38 | 9.06 | 20.15 |
| 3 | 32.10 | 14.94 | 11.68 | 23.75 |
| 4 | 36.24 | 25.59 | 13.83 | 27.12 |
| 6 | 42.48 | 44.47 | 17.91 | 36.23 |
| 8 | 45.02 | 56.66 | 21.93 | 52.70 |
| 10 | | 63.07 | 33.67 | 70.52 |
| 12 | | | 40.17 | 85.40 |
| 15 | | | 56.02 | 95.67 |
| 18 | | | 76.08 | 96.81 |
| 20 | | | 82.46 | |

The dissolution profiles of the compositions tested are illustrated in FIGS. 6–9 together with the release rate (% w/w dissolved/hour).

Example 2

Composition made by employment of triple compression
A tablet was prepared from the following ingredients:

Core:

| | |
|---|---|
| Midodrine hydrochloride | 1.66 mg |
| Hydroxypropylmethyl cellulose E 50 | 48.34 mg |
| Croscarmellose sodium | 10.00 mg |
| | 60.00 mg |

$1^{st}$ compression layer

| | |
|---|---|
| Midodrine hydrochloride | 0.62 mg |
| Hydroxypropylmethyl cellulose E 15 | 126.38 |
| Hydroxypropylmethyl cellulose K 100 LV | 8 |
| | 135.00 mg |

$2^{nd}$ compression layer

| | |
|---|---|
| Midodrine hydrochloride | 1.99 mg |
| Hydroxypropylmethyl cellulose E 50 | 143.01 mg |
| | 145.00 mg |

Using the core composition a core weighing 60 mg was compressed using a punch 6 mm in diameter. The core was compression coated using 135 mg of the $1^{st}$ compression layer composition and a punch of 9 mm in diameter. The thus compression coated core was compression coated again using 145 mg of the $2^{nd}$ compression layer composition and a punch of 11 mm in diameter.

A composition comprising midodrine hydrochloride 0.73 mg, hydroxypropylmethyl cellulose E 5 3.58 mg, Talc 2.51 mg and propylene glycol 0.71 mg was applied to the tablet by spray coating.

Finally a top coat comprising hydroxypropylmethyl cellulose E 5 1.79 mg, Talc 1.25 mg and propylene glycol 0.36 mg was applied to the tablet by spray coating.

The following results were obtained with respect to dissolution and release rate employing Dissolution Method I. The results are also shown in FIGS. 17 and 18.

| | % w/w dissolved based on the total weight of the composition tested | | | |
|---|---|---|---|---|
| | Core + $1^{st}$ + $2^{nd}$ compression layer (n = 2) | | Core + $1^{st}$ + $2^{nd}$ compression layer + coating (n = 6)* | |
| Time [hours] | % dissolved | Release rate [%/h] | % dissolved | Release rate [%/h] |
| 0.0 | 0.0 | 0.0 | 0.0 | 0.0 |
| 0.5 | 17.7 | 25.44 | 25.5 | 33.80 |
| 1.0 | 25.4 | 13.83 | 33.8 | 14.25 |
| 2.0 | 37.6 | 9.40 | 45.7 | 9.10 |
| 3.0 | 44.2 | 7.74 | — | — |
| 4.0 | 53.1 | 7.19 | 58.3 | 5.53 |
| 6.0 | 64.2 | 6.64 | 67.8 | 5.95 |
| 7.0 | 71.9 | 6.64 | — | — |
| 8.0 | 77.4 | 5.53 | 82.1 | 7.20 |
| 10.0 | 88.5 | 7.19 | 96.6 | 5.53 |
| 12.0 | 106.2 | 8.85 | 104.2 | 3.80 |

*Data from the release of the product is shown

Example 3

Composition made as a coated matrix
The following compositions were prepared:

Composition 1:

Core:

| | |
|---|---|
| Midodrine hydrochloride | 10.0 mg |
| Klucel LF | 340.0 mg |

Insoluble inner coat

| | |
|---|---|
| Methocel E 5 | 0.2 mg |
| Magnesium stearate | 0.1 mg |
| Talc Ponderax | 0.4 mg |
| Anti foam | 4.8 µg |
| Eudragit NE 30 D | 4.5 mg |

Soluble outer coat

| | |
|---|---|
| Methocel E 5 | 1.8 mg |
| Talc Ponderax | 1.8 mg |

Composition 2:

Core:

| | |
|---|---|
| Midodrine hydrochloride | 10.0 mg |
| Klucel MF | 340.0 mg |

Insoluble Inner coat

| | |
|---|---|
| Methocel E 5 | 0.2 mg |
| Magnesium stearate | 0.1 mg |
| Talc Ponderax | 0.4 mg |
| Anti foam | 4.8 Hg |
| Eudragit NE 30 D | 4.5 mg |

Soluble outer coat

| | |
|---|---|
| Methocel E 5 | 1.8 mg |
| Talc ponderax | 1.8 mg |

Cores of both composition 1 and composition 2 were compressed using a punch 10 mm in diameter. Core weighing 360 mg.

Both types of cores were coated with an insoluble inner coat and a soluble outercout. The release profile can be shifted up or down by changing the amount of weight increase of cores when applying the inner coat.

If suitable, the release profile can be changed by coating with other acrylic resins such as Eudragit RL 30 D, Eudragit RS 30 D or combinations thereof, or using other types of film forming agents such as ethylcellulose or silicone polymers. Furthermore, the release profile can be changed by using other types of matrix former such as acrylic resins, other types of cellulose ethers such as L-HPC (low-substituted hydroxypropylcellulose), HPC (hydroxypropylcellulose), HPMC (hydroxypropylmethylcellulose), HEC (hydroxyethylcellulose), MC (methylcellulose), HEMC (hydroxyethylmethylcellulose), EC (ethylcellulose) or other viscosity grades of HPC (hydroxypropylcellulose).

The following results were obtained with respect to dissolution and release rate (performed in accordance with the general method described herein):

|  | % w/w dissolved based on the total weight of the composition tested | | | |
|---|---|---|---|---|
| time (hours) | comp. 1 | comp. 1 coated | comp. 2 | comp. 2 coated |
| 1 | 16.72 | 7.67 | 15.77 | 6.41 |
| 2 | 27.25 | 14.60 | 22.36 | 10.85 |
| 3 | 36.86 | 21.24 | | |
| 4 | 45.66 | 27.59 | 32.14 | 19.62 |
| 6 | 60.37 | 38.18 | 36.26* | 24.03* |
| 8 | | 49.10 | 49.13* | 38.74* |
| 10 | 80.74 | 59.82 | | |
| 12 | 87.09 | 69.74 | 54.44* | 44.83* |
| 15 | 91.37 | 81.48 | 63.06 | 54.89 |
| 18 | | | 66.70* | 59.27* |

*Time is 5, 9, 11 and 17 hours

The results are also shown in FIGS. 10–13.

Example 4

| Multilayer coating compositions The following compositions were prepared: | |
|---|---|
| Composition 1: | |
| Core (Non pareil) | 200 mg |
| 1. coat | |
| Midodrine | 4.0 mg |
| Methocel E 5 M | 0.3 mg |
| Magnesium Stearate | 60.0 μg |
| Talc ponderax | 0.5 mg |
| Anti foam | 4.0 μg |
| Eudragit NE 30 D | 5.2 mg |
| 2. coat | |
| Midodrine | 3.0 mg |
| Methocel E 5 M | 0.3 mg |
| Magnesium Stearate | 60.0 μg |
| Talc ponderax | 0.5 mg |
| Anti foam | 4.0 μg |
| Eudragit NE 30 D | 6.1 mg |
| 3. coat | |
| Midodrine | 2.0 mg |
| Methocel E 5 M | 0.3 mg |
| Magnesium Stearate | 80.0 μg |
| Talc ponderax | 0.6 mg |
| Anti foam | 6.0 μg |
| Eudragit NE 30 D | 7.1 mg |
| 4. coat | |
| Midodrine | 1.0 mg |
| Methocel E 5 M | 0.4 mg |
| Magnesium Stearate | 80.0 μg |
| Talc ponderax | 0.7 mg |

| -continued | |
|---|---|
| Multilayer coating compositions The following compositions were prepared: | |
| Anti foam | 6.0 μg |
| Eudragit NE 30 D | 78 mg |
| Outer coat | |
| Methocel E 5 | 1.0 mg |
| Talc ponderax | 1.0 mg |

Non-pareil beads were coated in four steps with four different films in a fluid bed coater.

1. film comprising 1. coat
2. film comprising 2. coat
3. film comprising 3. coat
4. film comprising 4. coat.

A final layer of coating comprising the outer coat was applied and the films were cured at 70° C.

| Composition 2: | |
|---|---|
| Core (Non pareil) | 200 mg |

Non-pareil beads were coated in seven steps with four different films alternating with a blank film in a fluid bed coater.

The four different film formulations are similar to the four different film formulations in composition 1, the alternating coats are as follows:

| Alternating coat | |
|---|---|
| Methocel E 5 M | 0.2 mg |
| Magnesium stearate | 40.0 μg |
| Talc ponderax | 0.3 mg |
| Anti foam | 2.0 μg |
| Eudragit NE 30 D | 3.5 mg |

1. film comprising 1. coat
2. film comprising Alternating coat
3. film comprising 2. coat
4. film comprising Alternating coat
5. film comprising 3. coat
6. film comprising Alternating coat
7. film comprising 4. coat A final layer of coating comprising outer coat in composition 1 was applied and the films were cured at 70° C.

| Composition 3: | |
|---|---|
| Core (Non pareil) | 200 mg |
| 1. coat | |
| Midodrine | 4.0 mg |
| Paraffin, solid | 0.3 mg |
| Acetyltributyl citrate | 0.1 mg |
| Ethylcellulose | 1.9 mg |
| Aerosil 200 | 28.0 μg |

-continued

Composition 3:

2. coat

| | |
|---|---|
| Midodrine | 3.0 mg |
| Paraffin, solid | 0.3 mg |
| Acetyltributyl citrate | 0.1 mg |
| Ethylcellulose | 2.2 mg |
| Aerosil 200 | 32.0 μg |

3. coat

| | |
|---|---|
| Midodrine | 2.0 mg |
| Paraffin, solid | 0.4 mg |
| Acetyltributyl citrate | 0.1 mg |
| Ethylcellulose | 2.5 mg |
| Aerosil 200 | 40.0 μg |

4. coat

| | |
|---|---|
| Midodrine | 1.0 mg |
| Paraffin, solid | 0.4 mg |
| Acetyltributyl citrate | 0.2 mg |
| Ethylcellulose | 2.8 mg |
| Aerosil 200 | 40.0 μg |

Outer coats

| | |
|---|---|
| Paraffin, solid | 0.5 mg |
| Acetyltributyl citrate | 0.2 mg |
| Ethylcellulose | 3.3 mg |
| Aerosil 200 | 50.0 μg |

Non-pareil beads were coated in four steps with four different films in a fluid bed coater 1. film comprising 1. coat
2. film comprising 2. coat
3. film comprising 3. coat
4. film comprising 4. coat.

A final layer of coating comprising outer coats was applied.

The following results were obtained with respect to dissolution and release rate (performed in accordance with the general method described herein). The results are also shown in FIGS. 14–16.

| | % w/w dissolved based on the total weight of the composition tested | | |
|---|---|---|---|
| time (hours) | composition 1 | composition 2 | composition 3 |
| 0.5 | 26.02 | 19.84 | 5.41 |
| 1 | 55.24 | 33.08 | |
| 2 | 78.38 | 64.39 | 22.92 |
| 3 | 85.01 | 77.64 | 35.52 |
| 4 | 87.91 | 83.41 | 43.61 |
| 6 | 90.43 | 88.39 | 55.16 |
| 8 | 91.61 | 90.63 | 61.75 |
| 15 | | | 72.09 |

If suitable, the release profile can be changed by coating with other acrylic resins such as Eudragit RL 30 D, Eudragit RS 30 D or combinations thereof, or using other types of film forming agents such as ethylcellulose or silicone polymers, or incorporating lipophilic compounds such as, e.g., stearic acid, capric acid or hydrogenated castor oil in the film.

Example 5
Preparation of a Controlled Release Composition Using Commercially Available Filmforming Agents The present example illustrates the preparation of a coated pellet composition. The aim was to prepare pellets having a release kinetic different from zero order release.

Pellets were prepared from the following ingredients:

| | | |
|---|---|---|
| I | Midodrine hydrochloride | 600.0 g |
| II | Microcrystalline cellulose (Type PH 101) | 752.0 g |
| III | Lactose monohydrate | 2608.0 g |
| IV | Sodium carboxymethylcellulose | 40.0 g |
| V | Purified water | 1120.0 g |

I+II+III+IV are admixed in a Fielder intensive at an appropriate time and mixing intensity.

V is applied to the mixture (I–IV) while mixing. When V is applied the mixing is continued at an appropiate time with an appropiate mixing intensity The wetted mass is extruded through a screen with apertures between 0.4–1.0 mm.

The extrudate is spheronised until the surface of the resulting pellets is smooth.

An inner and an outer coating were applied:

Inner Coat

The weight of the pellets is increased with 8.5% w/w.

| | | |
|---|---|---|
| I | Hydroxypropylmethylcellulose | 13.5 g |
| II | Magnesium stearate | 2.9 g |
| II | Talc | 25.2 g |
| IV | Eudragit NE 30 D | 895.1 g |
| V | Purified water | 1135.4 g |

The pellets are coated in a fluid bed with appropriate process parameters.

Immediately after the inner coat has been applied an outer coat is applied.

Outer Coat

The weight of the pellets is increased with 1% w/w.

| | | |
|---|---|---|
| I | Hydroxypropylmethylcellulose | 20.0 g |
| II | Talc | 20.0 g |
| III | Purified water | 460.0 g |

The pellets are coated in a fluid bed with appropriate process parameters.

The weight of 1 unit dose containing 30 mg midodrine hydrochloride is 219 mg.

The release profile can be shifted up or down by changing the amount of weight increase of pellets when applying the inner coat.

The release profile can be changed by mixing fractions of pellets with different amounts of inner coating applied or the release profile can be changed by coating with other acrylic resins such as Eudragit RL 30 D, Eudragit RS 30 D or combinations thereof, or using other types of film forming agents such as ethylcellulose or silicone polymers, Furthermore, the release profile can be changed by applying a fraction of non-coated pellets or by applying an enteric coating to a fraction of pellets.

Example 6
Preparation of a Controlled Release Formulation Using a Film Containing Paraffin The present example illustrates the preparation of a coated pellet composition. The aim was to prepare pellets having a release kinetic different from zero order release.

Coated pellets were prepared from the following ingredients:

The composition and manufacturing process of pellets are similar to Example 5.

A coating was applied. Paraffin-containing film; the weight of the pellets is increased with 6% w/w.

| I | Paraffin, solid | 29.89 g |
|---|---|---|
| II | Acetyltributyl citrate | 10.53 g |
| III | Ethyl cellulose | 196.61 g |
| IV | Silicium dioxide (Aerosil 200) | 2.95 g |
| V | Isopropyl alcohol | 3970.03 g |

The pellets are coated in a fluid bed with appropriate process parameters.

The weight of 1 unit dose containing 30 mg midodrine hydrochloride is 212 mg.

Example 7
Preparation of a Controlled Release Composition Having a Zero Order Release The present example illustrates the preparation of a coated beads composition. The aim was to prepare beads having a zero order release kinetic.

Coated beads were prepared from the following ingredients:

Non dissolvable non-pareil beads of equal size are coated with a suspension of midodrine hydrochloride. A diffusion barrier is coated on top of the midodrine hydrochloride layer, and thereby controlling the release of midodrine hydrochloride.

4000 g non-pareil beads having a uniform particle size in a range between 0.4 mm and 1.0 mm are transferred to a fluid bed coater.

The beads are coated with coating suspension 1 (containing midodrine hydrochloride):

| I | Hydroxypropylmethylcellulose | 8.8 g |
|---|---|---|
| II | Magnesium stearate | 1.9 g |
| III | Talc | 16.5 g |
| IV | Eudragit NE 30 D | 585.1 g |
| V | Purified water | 742.1 g |
| VI | Midodrine hydrochloride | 200.0 g |

The weight of the beads is increased with 10% w/w.

The beads are coated employing appropriate process parameters.

Immediately after coating suspension 1 has been applied a second coating suspension is applied.

The beads are coated with coating suspension 2:

| I | Hydroxypropylmethylcellulose | 11.7 g |
|---|---|---|
| II | Magnesium stearate | 2.5 g |
| III | Talc | 21.7 g |
| IV | Eudragit NE 30 D | 772.3 g |
| V | Purified water | 979.6 g |

The weight of the coated beads is increased with 6% w/w.

The pellets are coated employing appropriate process parameters.

Immediately after coating suspension 2 has been applied a third coating suspension is applied.

The beads are coated with coating solution 3:

| I | Hydroxypropylmethylcellulose | 23.3 g |
|---|---|---|
| II | Talc | 23.3 g |
| III | Purified water | 536.8 g |

The weight of the coated beads is increased with 1% w/w.

The beads are coated in a fluid bed employing appropriate process parameters.

The weight of 1 unit dose containing 20 mg midodrine hydrochloride is 471 mg.

By changing the weight gain of the beads when applying the second coating suspension, the release profile can be shifted up or down.

The release profile can be changed by mixing fractions of beads having different amounts of second coating suspension applied or the release profile can be changed by coating with other acrylic resins such as Eudragit RL 30 D, Eudragit RS 30 D or combinations thereof, or using other types of film forming agents such as ethylcellulose or silicone polymers.

The above-mentioned filmforming agents can also be combined with pore forming agents such as cellulose ethers, polyoles, PEG's.

Furthermore, the release profile can be changed by applying an enteric coating to a fraction of the coated beads.

Example 8
Preparation of a Zero Order Controlled Release Composition

The present example illustrates the preparation of a coated minitablet composition. The aim was to prepare coated minitablets of equal size in order to obtain a zero order release kinetic.

| Formulation of minitablets: | | |
|---|---|---|
| I | Midodrine hydrochloride | 800.0 g |
| II | Dicalcium phosphate | 2960.0 g |
| III | Talc | 100.0 g |
| IV | Magnesium stearate | 40.0 g |
| V | Polyvinylpyrrolidone 90 | 100.0 g |
| VI | Purified water | 800.0 g |

V is dissolved in VI.

I+II are transferred to a Fielder intensive mixer and admixed at an appropiate time and mixing intensity.

The mixture is wetted with the solution V+VI.

Granulation is performed at an appropriate time and mixing intensity.

The drying of the wet granulate is carried out in an Aeromatic fluid bed.

The dried granulate is passed through a suitable sieve. IV+V are sieved through a 0.3 mm sieve and admixed to the sieved particulate mixture in a cube mixer for 10 min.

The thus obtained particulate mixture is compressed into tablets weighing 15 mg.

A dose of 30 mg midodrine corresponds to 10 minitablets.

Coating of the Minitablets

The minitablets are coated with inner and outer coatings corresponding to the description in Example 7.

By changing the weight gain of the minitablets when applying the inner coat, the release profile can be shifted up or down The release profile can be changed by mixing fractions of minitablets having different amounts of inner coating applied or the release profile can be changed by coating with other acrylic resin such as Eudragit RL 30 D, Eudragit RS 30 D or combinations thereof, or using other types of film forming agents such as ethylcellulose or silicone polymers.

The above mentioned filmforming agents can also be combined with pore forming agents such as, e.g., cellulose ethers, polyoles, PEG's, etc.

Furthermore, the release profile can be changed by applying an enteric coating to a fraction of the coated minitablets.

Example 9
Preparation of a Controlled Release Composition Having a Release Kinetic Different from that of Zero Order

| Matrix minitablets: | | |
|---|---|---|
| I | Midodrine hydrochloride | 800.0 g |
| II | Ethyl cellulose (10 μm) | 2960.0 g |
| III | Talc | 200.0 g |
| IV | Magnesium stearate | 40.0 g |
| V | Purified water | 800.0 g |

I+II are admixed in a Fielder intensive mixer at an appropriate time and mixing intensity.

The mixture is wetted with V while mixing at an appropriate mixing intensity.

The wetted mixture is granulated at an appropriate time and mixing intensity.

The drying of the wet granulate is carried out in an Aeromatic fluid bed.

The dried granulate is passed through a suitable sieve. III+IV are sieved through a 0.3 mm sieve and admixed to the sieved particulate mixture in a cube mixer for 10 min.

The thus obtained particulate mixture is compressed into tablets weighing 15 mg.

A dose of 30 mg of midodrine hydrochloride is contained in 10 minitablets.

If suitable the release profile can be changed by using other cellulose ethers such as HPC, L-HPC, HPMC or combinations of thereof.

The principle of a matrix composition may also be used for a single unit tablet containing the total amount of midodrine hydrochloride in one unit.

In order to further increase the retardation of the dissolution of midodrine hydrochloride the minitablets may be coated according to Example 7. The amount of coating applied may be varied to shift the dissolution profile up or down.

Example 10
Preparation of a Controlled Release Composition Having Release Kinetic Different Form Zero Order

| Matrix minitablets: | | |
|---|---|---|
| I | Midodrine hydrochloride | 800.0 g |
| II | Ethyl cellulose (10 μm) | 2960.0 g |
| III | Talc | 200.0 g |
| IV | Magnesium stearate | 40.0 g |
| V | Isopropyl alcohol | 800.0 g |

I+II are admixed in a Fielder intensive mixer at an appropriate time and mixing intensity.

The mixture is wetted with V while mixing at an appropriate mixing intensity.

The wetted mixture is granulated for an appropriate time and mixing intensity.

The drying of the wet granulate is carried out in an Aeromatic fluid bed.

The dried granulate is passed through a suitable sieve. III+IV are sieved through a 0.3 mm sieve and admixed to the sieved particulate mixture in a cube mixer for 10 min.

The thus obtained particulate mixture is compressed into tablets weighing 15 mg.

A dose of 30 mg of midodrine hydrochloride is contained in 10 minitablets.

In order to further increase the retardation of the dissolution of midodrine hydrochloride the minitablets may be coated according to Example 7. The amount of coating applied may be varied to shift the dissolution profile up or down.

Example 11

| Composition made by employment of double compression A tablet was prepared from the following ingredients: | |
|---|---|
| $1^{st}$ compression layer | |
| Midodrine hydrochloride | 2.40 g |
| Starch 1500 | 89.46 g |
| Lactose monohydrate | 180.00 g |
| Eudragite RS 30 D | 75.0 g |
| Acetyl tributylcitrate | 5.64 g |
| $2^{nd}$ compression layer | |
| Midodrine hydrochloride | 0.5 g |
| Hydroxypropylmethylcellulose E 50 | 49.5 g |

The granulate for $1^{st}$ compression layer was prepared in the following way; Midodrine hydrochloride and Starch 1500 was mixed by hand. This mixture and lactose monohydrate was mixed in a Moulinex food processor for 30 sec.

The granulating fluid comprising Eudragit RS 30 D and acetyl tributylcitrate was mixed by stirring for 5 min.

The granulating fluid was applied to the powder mixture while mixing in the Moulinex food processor. The time for applying the granulating fluid was 45 sec.

Wet massing time for the moist powder mixture was 30 sec.

The moist granulate was tray dried and the dried granulate was passed through a 1000 μm screen.

The granulate for $2^{nd}$ compression layer was prepared in the following way: Midodrine hydrochloride and hydroxypropylmethyl cellulose E 50 was mixed by hand and finally passed through a 500 μm screen.

A double compression tablet was prepared in the following way: A shallow concave round punch 11 mm in diameter was used to compress the tablet. 250 mg of the granulate for $1^{st}$ compression layer was weighed into the die and compressed gently to a loose compact. 200 mg of the granulate for $2^{nd}$ compression layer was weighed on top the loose compact. The loose compact and the granulate for $2^{nd}$ compression layer was compressed with a force of approx. 17 kN to form a coherent tablet.

After compression a release controlling film, a film containing midodrine hydrochloride and a blank film were applied to the tablets.

Example 12
Composition Made in the Form of Capsules Containing Multiple Units (MICAP)—EC Pellets Coated with 45% w/w Dry Matter The midodrine controlled release product is prepared by manufacturing one type of pellet, which afterwards is coated with different types of film coatings. The capsule ends up with 3 different types of pellets (one non-coated pellet, one CR-coated pellet and one EC-pellet).

Pellets Preparation

The pellet is prepared by the use of an extrusion/spheronization technique. The ingredients are listed in Scheme 12–1.

Scheme 12-1:

| Ingredients | Amount (g) pr. Batchsize |
| --- | --- |
| Microcrystalline cellulose | 2135.0 |
| Lactose monohydrate | 1207.5 |
| Carmellose Sodium | 70.0 |
| Midodrine Hydrochloride | 87.5 |
| Purified water | 2000.0 |

The ingredients are mixed and wetted in a Fielder high shear mixer in which the water is applied by a nozzle.

The wetted mass was extruded in a Nica E 140 extruder with a screen size of 600 $\mu$m (those pellets which is being used for non coated pellets and for CR-coating) or 800 $\mu$m (those pellets used for EC-coating). The extrudate was spheronized in a laboratory unit for 5 min. The pellets were dried in a laboratory scala fluid bed for approx. 75 min at 50° C.

The dried pellets used for non coated pellets and for CR-coating were screened through a screen of 700 $\mu$m and the dried pellets used for EC-coating were fractionated with a lower screen of 500 $\mu$m and a upper screen of 1000 $\mu$m.

Step 1 Pellets (Non Coated Pellets)

One batch of these pellets is not coated because it is used as an immediate release unit. The pellets are a part of the content in the capsule.

Step 2 pellets (CR-coated Pellets)

One batch of these pellets is coated with an inner coat and an outer coat in a fluid bed (GPCG3) with a 0.8 mm spray nozzle and a spray pressure of 2.5 bar. The composition for the coating is shown in Scheme 12–2.

Scheme 12-2:

| Ingredients | Amount (g) pr. batchsize |
| --- | --- |
| Inner coat (batchsize 2000 g) | |
| Hypromellose (viscosity 5 cps) | 13.1 |
| Purified water | 1094.0 |
| Magnesium stearate | 2.7 |
| Talc | 26.2 |
| Polyacrylate dispersion 30% (Eudragit NE30D) | 864.0 |
| Outer coat (batchsize 1000 g) | |
| Hypromellose (viscosity 5 cps) | 40.0 |
| Purified water | 920.0 |
| Talc | 40.0 |

In the coating process the following amount of inner and outer coat were applied. The amount of dry matter applied calculated in percentage of the core weight also appears from below.

| | |
| --- | --- |
| Inner coat: | 1788.1 g per 3000.0 g pellets (dry matter: 9% of the core weight) |
| Outer coat: | 375.0 g per 3000.0 g pellets (dry matter: 1% of the core weight) |

Throughout the coating process the bed temperature was maintained substantially in the interval from 20–25° C. by adjustment of the liquid flow rate or the inlet temperature. The inlet air temperature was kept at approximately 32° C. After the aplication of the coatings the coated pellets were cured at a bed temperature of approximately 70° C. for 30 min. Then the pellets were screened through a screen 1.0 mm. Oversized material was discarded.

Step 3 Pellets (EC Pellets)

One batch of these pellets is coated with an EC-coat in a fluid bed (Würster technique) with a 0.8 mm spray nozzle and a spray pressure of 2.5 bar. The composition for the coating is shown in Scheme 12–3.

Scheme 12-3:

| Ingredients | Amount (g) pr. batchsize |
| --- | --- |
| Isopropyl alcohol | 3852.0 |
| Talc | 100.0 |
| Acetyltributyl citrate | 99.2 |
| Methacrylic acid - methyl methacrylate copolymer (1:2) (Eudragit S12.5) | 3948.8 |

In the coating process the following amount of the coat were applied. The amount of dry matter applied calculated in percentage of the core weight also appears from below.

15,517.2 g per 3000.0 g pellets (dry matter: 45% of the core weight)

Throughout the coating process the bed temperature was maintained substantially in the interval from 30–38° C. by adjustment of the liquid flow rate or the inlet temperature. The inlet air temperature was kept at approximately 49° C. After the application of the coating the pellets were screened through a screen 1.3 mm. Oversized material was discarded.

Capsule Filling

The 3 different pellets (steps 1, 2 and 3) were filled into capsules by hand. The amount of pellets per capsule is shown in Scheme 12–4.

Scheme 12-4:

| Unit | Amount (mg) per capsule |
| --- | --- |
| Capsule | approx. 76.3 |
| Pellets step 1 | approx. 50.4 corresp. to 1.25 mg midodrine hydrochloride |
| Pellets step 2 | approx. 110.6 corresp. to 2.5 mg midodrine hydrochloride |
| Pellets step 3 | approx. 72.7 corresp. to 1.25 mg midodrine hydrochloride |
| Total weight of capsule | approx. 310 corresp. to 5.0 mg midodrine hydrochloride |

Dissolution Data

The following results were obtained with respect to dissolution and release rate employing Dissolution Method III The mixture of the 3 types of pellets had the dissolution data shown in Scheme 12–5:

Scheme 12-5

Capsule (n = 12)

| Time (hours) | % dissolved | Release rate (%/h) |
|---|---|---|
| 0.0 | 0.0 | 0.00 |
| 0.5 | 29.9 | 33.26 |
| 1 | 33.3 | 6.63 |
| 2 | 39.8 | 7.00 |
| 3 | 47.3 | 7.84 |
| 4 | 55.5 | 8.31 |
| 6 | 72.3 | 7.02 |
| 7 | 77.9 | 10.00 |
| 8 | 92.3 | 7.92 |
| 10 | 95.2 | 1.30 |
| 12 | 97.5 | 1.15 |

The results are also shown in FIG. 19.

In FIG. 20 is given the dissolution data for 4 different compositions having different content of midodrine. As is evident from the profiles, the dissolution is independent on the midodrine dose.

Example 13
Composition in the Form of Capsules Containing Multiple Units (MICAP)—EC pellets Coated with 35% w/w Dry Matter The following example illustrates that the amount of dry matter in the EC coating is very important in order to achieve a composition, which has the dissolution characteristics according to the requirements described herein. Thus, an EC coat containing 35% w/w dry matter is apparently not as suitable as an EC coat with 45% w/w dry mater (Example 12).

The midodrine controlled release product is prepared as in Example 12. The only difference is the amount of dry matter applied on the entero coated pellets.

Pellets Preparation
  As described in Example 12
Step 1 pellets (Non Coated Pellets)
  As described in Example 12
Step 2 Pellets (CR-coated Pellets)
  As described in Example 12
Step 3 Pellets (EC Pellets)

The composition for the coating and the coating procedure are the same as those being used in Example 12 (except the amount of dry matter applied on the pellets).

In the coating process the following amount of the coat were applied. The amount of dry matter applied calculated in percentage of the core weight also appears from below.

12,069.0 g per 3000.0 g pellets (dry matter: 35% of the core weight)

Capsule Filling
The amount of pellets per test is shown in Scheme 13–1

Scheme 13-1:

| Unit | Amount (mg) per capsule |
|---|---|
| Pellets step 1 | approx. 50.4 corresponding to 1.25 mg midodrine hydrochloride |
| Pellets step 2 | approx. 110.6 corresponding to 2.5 mg midodrine hydrochloride |
| Pellets step 3 | approx. 67.6 corresponding to 1.25 mg midodrine hydrochloride |

Dissolution Data

The following results were obtained with respect to dissolution and release rate employing Dissolution Method III.

The mixture of the 3 types of pellets had the dissolution data shown in Scheme 13–2:

Scheme 13-2

Capsule (n = 6)

| Time (hours) | % dissolved | Release rate (%/h) |
|---|---|---|
| 0.0 | 0.0 | 0.00 |
| 0.5 | 28.9 | 32.00 |
| 1 | 32.0 | 6.09 |
| 2 | 37.9 | 8.98 |
| 3 | 50.0 | 16.06 |
| 4 | 70.0 | 14.94 |
| 6 | 89.7 | 5.30 |
| 7 | 90.4 | 2.14 |
| 8 | 94.0 | 2.56 |
| 10 | 97.2 | 1.50 |
| 12 | 100.0 | 1.40 |

The results are also shown in FIG. 21.

Example 14

Composition Made by Employment of Mixing a Matrix Granulate and a Slow Release Granulate.

The composition of the granulates are equal to granulates in Example 11.

250 mg of the granulate called $1^{st}$ compression layer (slow release granulate) was mixed with 200 mg of the granulate called $2^{nd}$ compression layer (matrix granulate).

A shallow concave round punch 11 mm in diameter was used to compress the tablet. The granulate mixture was placed in the die and the granulate was compressed with a compression force of approx. 17 kN to form a coherent tablet.

After compression a release controlling film, a film containing midodrine hydrochloride and a blank film were applied to the tablets.

The film compositions and the applied amounts are equal the compositions and amounts applied in Example 11.

The following results were obtained with respect to dissolution and release rate employing Dissolution method I.

| | % w/w dissolved based on the total weight of the composition tested | | | |
|---|---|---|---|---|
| | Tablet 1 (n = 1) | | Tablet 2 (n = 1) | |
| Time [hours] | % dissolved | Release rate [%] | % dissolved | Release rate [%] |
| 0.0 | 0 | 0.0 | 0 | 0.0 |
| 0.5 | 18 | 18.0 | 18 | 18.0 |
| 1.0 | 18 | 0.5 | 18 | 1.0 |
| 2.0 | 19 | 2.0 | 20 | 2.0 |
| 3.0 | 22 | 3.5 | 22 | 2.5 |
| 4.0 | 26 | 5.5 | 25 | 6.5 |
| 6.0 | 48 | 27.0 | 42 | 17.0 |
| 7.0 | 87 | 23.5 | 69 | 19.0 |
| 8.0 | 95 | 4.0 | 80 | 8.0 |
| 10.0 | 96 | 0.5 | 89 | 2.5 |
| 12.0 | 96 | 0.0 | 93 | 2.0 |

The results are also shown in FIG. 22.

Example 15

Pilot Bioavailability Study of Two Prototypes of Midodrine Controlled Release Formulations Compared to Standard Formulation (Tablet) in Healthy Volunteers Introduction Systolic blood pressure is transiently and minimally decreased in normal individuals when rising to upright position. Normal physiologic feedback mechanisms work through neurally mediated pathways to maintain the standing blood pressure and thus support adequate cerebral perfusion. These compensatory mechanisms that regulate blood pressure when standing are deficient in patients with orthostatic hypotension, a condition that may lead to inadequate cerebral perfusion with accompanying symptoms of syncope, dizziness/light-headedness and blurred vision, among others.

Midodrine is a prodrug labeled for treatment of orthostatic hypotension. After absorption it is readily metabolized to desglymidodrine that acts as an agonist at the peripheral α-1 receptors in the smooth muscles of arteries and veins, but has no direct central nervous or cardiac effects. Its main effect is to increase the vascular tone thus increasing the total peripheral resistance and rising blood pressure. The pressor effect of midodrine is manifest within 20 to 90 minutes after oral administration of a single dose. This pressor effect usually persists for 3 to 6 hours. Doses used in clinical practise (10 mg t.i.d.) significantly increase standing blood pressure, thus alleviating symptoms of orthostatic hypotension.

Controlled Release Formulation

The rationale of the development of a controlled release formulation is to reduce the number of dosings during the day and to avoid major changes in plasma concentration of desglymidodrine. This will increase compliance and reduces changes in severity of symptoms of orthostatic hypotension and thus possibly increase quality of life.

Two prototypes have been developed according to the present invention. One prototype "Micap" is a multiple unit formulation (see Example 12), each unit releasing its amount of midodrine dependent on the acidity of the environment. As the acidity is different in different parts of the gut the result is a continuous release during the passage. The other prototype "Mitab" is composed of three layers releasing midodrine differently creating a time-dependent release (see Example 2). The strength of the controlled release formulations has been chosen to 5 mg to allow for individual titration of the total daily dose. The study is a pilot trial of the bioavailability of the two prototypes compared to a standard tablet.

Objective

To determine the bioavailability of two novel prototypes of controlled release formulations of midodrine hydrochloride compared to standard tablets.

Trial Design

Open-labeled randomized 3 way cross-over trial. All subjects were administered 10 mg midodrine hydrochloride either as a standard tablet or as one of two novel controlled release formulations at three occasions distributed 3 days apart.

Trial Population

Eight healty volunteers, both genders, 18–55 years of age, normal weight, informed consent, not pregnant or lactating, not trying to become pregnant, no liver, renal or gastrointestinal disease that may influence pharmacokinetics or the health of the volunteers, no history of alcohol and drug abuse, non-smokers.

Assessments $AUC_t$ (area under the plasma concentration curve to time t), $C_{max}$(peak (or shoulder or plateau) plasma concentration), $t_{max}$(time to peak (or shoulder or plateau) plasma concentration), MRT (mean residence time), $t_{>75\% \, Cmax}$ ($W_{75}$—duration of plasma concentration above 75% of $C_{max}$), HVD ($W_{50}$—half value duration) and time to a possible second peak (or shoulder or plateau) were calculated for midodrine and its biologically active metabolite, desglymidodrine. $AUC_{infinity}$ (area under the plasma concentration curve extrapolated to infinity) and $t_{1/2}$ (plasma concentration half life) are calculated, whenever relevant.

Whenever, the concentration went under the detection limit, the values were set to ½×detection limit, i.e. for midodrine ½×1 ng/ml and for desglymidodrine ½×0.5 ng/ml. Because of such a contribution to the AUC, $AUC_{24}$ was often larger than $AUC_{infinity}$.

Trial Products

Midodrine tablets 5 mg, Gutron from Nycomed, Denmark, midodrine controlled release formulation (pH dependent release) prepared as described in Example 12, 5 mg, and midodrine controlled release formulation (time dependent release) prepared as described in Example 2, 5 mg.

Food and Liquid

The subjects were fasting from 8 hours before dosing until 3 hours post dosing. Water was allowed until 1 hour before dosing. No alcoholic beverages or beverages containing caffeine (coffee, tea or cola) are allowed from 8 hours before dosing until last blood sample has been drawn (24 hours).

Study drug was administered to the subjects with 150 ml of water. Additional 150 ml of water was administered to the subjects 1 and 2 hours after dosing.

Meals were standardized throughout all 3 study visits and served according to the following schedule:

4 hours after dosing: lunch 7 hours after dosing: snack 10 hours after dosing: dinner 14 hours after dosing: snack Study Drug Two tablets or capsules of study drug (midodrine tablets, Mitab or Micap) (total dose 10 mg) were administered between 7.30 and 8.30 am. Administration of study drug is followed by at least three days washout Blood Samples Seven ml of venous blood were withdrawn immediately before dosing, and at 15 and 30 minutes, 1, 1.5, 2, 3, 5, 6, 7, 8, 9, 10, 11, 12, 14, 16, 20 and 24 hours after dosing, The blood samples were placed on ice immediately after drawing and centrifuged and frozen within 20 minutes. Analysis for midodrine and desglymidodrine was performed by HPLC with fluorescence detection. The analyses were performed by Quintiles AB, Uppsala, Sweden.

Results

The mean plasma concentration curves for midodrine and desglymidodrine, respectively, are shown in FIGS. 23 and 24. The measured and calculated parameters for each composition (n=7 for Micap and Mitab, n=8 for standard tablets) are given in the following.

AUC and MRT have been calculated using the trapezoidal rule and the AUMC method (Yamaoka K., Nakagawa T., Uno T.: Statistical moments in pharmacokinetics, J. Pharmacokin. Biopharm. 1978:6:547–68).

For extrapolation to infinity (the tail) the following formulas have been used:

$C_p/K_e$ (for AUC) and $nC_p/(k_e^z)$ (for AUMC)

Where $C_p$=the last measured plasma concentration $k_a$=the elimination rate constant N=the time for last data point with measurable concentrations.

|  | Micap | Mitab | Standard tablets |
|---|---|---|---|
| Midodrine ng/ml, mean values (standard deviation): | | | |
| $AUC_{24}$ | 32.8 (6.7) | 32.7 (12.1) | 51.7 (13.5) |
| $C_{max}$ | 10.0 (2.6) | 12.8 (6.5) | 41.4 (12.6) |
| $t_{max}$ | 0.7 (0.4) | 0.9 (0.5) | 0.5 (0.2) |
| MRT | 3.0 (0.4) | 2.3 (0.3) | 1.0 (0.2) |
| HVD | 2.6 (1.1) | 1.5 (0.8) | 0.9 (0.3) |
| $t_{>75\% \, Cmax}$ | 1.0 (1.0) | 0.8 (0.6) | 0.5 (0.1) |
| $AUC_{infinity}$ | 24.1 (6.7) | 21.8 (13.1) | 41.3 (14.0) |
| Desglymidodrine ng/ml, mean values (standard deviation): | | | |
| $AUC_{24}$ | 106.0 (29.1) | 92.7 (36.4) | 114.4 (31.9) |
| $C_{max}$ | 11.4 (3.2) | 8.7 (5.0) | 21.7 (5.1) |
| $t_{max}$ | 5.0 (0.0) | 2.9 (1.1) | 1.4 (0.4) |
| MRT | 9.5 (1.0) | 11.8 (4.1) | 4.7 (0.5) |
| HVD | 7.7 (0.4) | 9.9 (4.1) | 4.1 (0.4) |
| $t_{>75\% \, Cmax}$ | 3.4 (0.3) | 4.4 (0.5) | 2.1 (0.4) |
| $AUC_{infinity}$ | 111.5 (33.9) | 104.1 (36.9) | 112.9 (32.5) |
| Sum of midodrine and desglymidodrine nmol/l, mean values (standard deviation): | | | |
| $AUC_{24}$ | 566.1 (145.6) | 509.1 (195.2) | 667.3 (176.4) |
| $C_{max}$ | 60.5 (14.5) | 66.0 (29.7) | 195.1 (51.9) |
| $t_{max}$ | 3.0 (1.7) | 1.3 (0.9) | 0.6 (0.2) |
| MRT | 9.7 (1.0) | 12.4 (4.5) | 4.6 (0.6) |
| HVD | 7.7 (0.8) | 5.0 (2.5) | 1.9 (0.8) |
| $t_{>75\% \, Cmax}$ | 4.4 (1.2) | 1.8 (1.3) | 0.9 (0.4) |
| $AUC_{infinity}$ | 608.7 (172.8) | 588.2 (190.1) | 661.1 (183.3) |
| Midodrine nmol/l, mean values (standard deviation) | | | |
| $AUC_{24}$ | 112.7 (23.2) | 112.5 (41.6) | 178.0 (46.4) |
| $C_{max}$ | 34.3 (9.1) | 43.9 (22.4) | 142.3 (43.5) |
| $t_{max}$ | 0.7 (0.4) | 0.9 (0.5) | 0.5 (0.2) |
| MRT | 3.0 (0.4) | 2.3 (0.3) | 1.0 (0.2) |
| HVD | 2.6 (1.1) | 1.5 (0.8) | 0.9 (0.3) |
| $t_{>75\% \, Cmax}$ | 1.0 (1.0) | 0.8 (0.6) | 0.5 (0.1) |
| $AUC_{infinity}$ | 83.0 (23.1) | 74.9 (45.0) | 142.1 (48.2) |
| Desglymidodrine nmol/l, mean values (standard deviation): | | | |
| $AUC_{24}$ | 453.4 (124.7) | 396.6 (156.0) | 489.4 (136.5) |
| $C_{max}$ | 48.6 (13.5) | 37.4 (21.5) | 92.9 (22.0) |
| $t_{max}$ | 5.0 (0.0) | 2.9 (1.1) | 1.4 (0.4) |
| MRT | 9.5 (1.0) | 11.8 (4.1) | 4.7 (0.5) |
| HVD | 7.7 (0.4) | 9.9 (4.1) | 4.1 (0.4) |
| $t_{>75\% \, Cmax}$ | 3.4 (0.3) | 4.4 (0.5) | 2.1 (0.4) |
| $AUC_{infinity}$ | 477.2 (144.9) | 445.4 (157.7) | 483.3 (138.9) |

Furthermore, the time interval in which the concentration of midodrine, desglymidodrine or the sum of midodrine and desglymidodrine is at a constant value±40% has been determined. The time interval is found by looking at all possible time intervals (using the time points from the blood sampling) of all possible lengths. For each time interval the mean is calculated and it is checked whether all plasma concentration points in that time interval is lying within±40% of the mean value. The time interval in question is the longest time interval for which all concentration points in the interval lie within the mean of the time interval±40%. In order to get a relevant interval the constant value minus 40% has to be higher than the detection limit. The interval is calculated for each patient and the mean value of the length of time interval is given.

For example, for patient 1 the MICAP capsules gave a mean plasma concentration of desglymidodrine at 8.5 ng/ml in the time interval from 2 hours to 9 hours (i.e. a 7 hours interval). In this period the maximum plasma concentration of desglymidodrine was measured as 11.8 ng/ml and the minimum plasma concentration as 5.5 ng/ml. Since 8.5 ng/ml+40% is 11.9 ng/ml and 8.5 ng/ml−40% is 5.1 ng/ml all measured plasma concentration points in that particular interval lie within the mean value±40%. Since this was the longest time interval where all concentration points lie within the mean ±40% the resulting time interval for the MICAP capsules for patient 1 was 7 hours.

The following results were obtained:

| Time interval (hours) where the concentration of midodrine lies at a constant value ± 40%: | |
|---|---|
| Micap (n = 7) | 1.7 |
| Mitab (n = 7) | 1.4 |
| Standard tablets (n = 8) | 0.63 |
| Time interval (hours) where the concentration of desglymidodrine lies at a constant value ± 40%: | |
| Micap (n = 7) | 6.3 |
| Mitab (n = 7) | 11.5 |
| Standard tablets (n = 8) | 3.7 |
| Time interval (hours) where the sum of the concentration of midodrine and desglymidodrine lies at a constant value ± 40%: | |
| Micap (n = 7) | 7.5 |
| Mitab (n = 7) | 11.9 |
| Standard tablets (n = 8) | 3.5 |

The aim of the pilot study was to test the bioavailability of the two novel compositions and a standard Gutron tablet and to estimate whether the compositions are bioequivalent. Furthermore, the controlled release properties of the novel compositions as compared to the standard composition (Gutron tablet) can be depicted from the data generated.

The values of $C_{max}$ and $AUC_{0-24}/AUC_{infinity}$ of the standard tablet are greater than the same values of each of the two prototypes considering the plasma values of midodrine, desglymidodrine and the sum of the two. It is expected that $C_{max}$ is lower in controlled release compositions than in plain release compositions as this reflects a lesser degree of fluctuation of plasma values. This is one of the purposes of a controlled release composition. It is further supported by the prolongation of the time interval in which the plasma values of midodrine, desglymidodrine and the sum of the concentrations of the two lie at a constant value.

The sum of the plasma concentrations of midodrine and the active metabolite desglymidodrine reflects the total amount of drug absorbed into the blood stream. The values of $T_{max}$, $W_{50}$ and $T_{>75 \%cmax}$ ($W_{75\%}$) and MRT for this sum concentration are more than 2 times greater of the novel controlled release compositions than the values of the standard tablet. The prolongation of the above mentioned values means that the active drug substance resides in the plasma for a longer time period reducing the numbers of daily dosing needed. Thus, another purpose of a controlled release composition is fulfilled.

Conclusion

Based on the AUC values, the bioavailabilities of the novel controlled release compositions are lesser than the bioavailability of the standard tablet indicating that the content of active drug substance in the controlled release compositions should be increased to establish bioequivalence.

The novel compositions possess controlled release properties as compared to the standard tablet for reasons discussed above.

Example 16

Powder Preparation e.g for Use in a Needle-free Device

| Composition | | |
|---|---|---|
| I | Midodrine HCl | 1000.0 g |

The particle size distributions for the ingredients should be appropiate for deposition of the composition through the skin e.g. 0.5 $\mu$m to 10 $\mu$m.

The powder is filled into a drug casette, each containing 5 mg Midodrine HCl.

Suspending agents such as glucose, lactose, celluloses, starches (maize-, rice-, potato-), calcium phosphate or mixtures of these may be used.

Example 17

Liquid Composition for Use in a Needle-free Device

| Composition | | |
|---|---|---|
| I | Midodrine HCl | 50.0 g |
| II | Sodium edetate | 0.5 g |
|  | Disodium hydrogen phosphate dihydrate | 2.0 g |
|  | Sodium dihydrogen phosphate dihydrate | 2.0 g |
| III | Water for injection | 900.0 g |
| IV | Water for injection | ad 1000.0 g |

I is dissolved in III upon continuous stirring. The remaining solid ingredients are added to the solution one by one during continuous stirring. Following complete dissolution of the solids. purified water is added to a total weight of 1000.0 g.

The formulation is filtrated (0,22 $\mu$m) and is filled into glass devices with a piston (e.g. teflon) and a stopper (e.g. rubber (natural or synthetic substances))

Tonicity agents may be dextrose, glycerol, sorbitol, mannitol, potassium nitrate and sodium sulphate decahydrate or mixtures thereof.

pH may be adjusted to the appropiate value by use of additional buffer salts such as citric acid, sodium citrate, and potassium dihydrogen phosphate or mixtures of these.

Example 18

Liquid Compositions for Pulmonal Delivery

A. Pressurised metered-dose preparation for inhalation

| Composition | | |
|---|---|---|
| I | Midodrine HCl | 50.0 g |
| II | Norflurane | ad 1000.0 ml |

I is dissolved or suspended in liquid II at low temperature during continuous agitation. For suspensions, the particle size distribution should be appropiate for deposition of the composition in the lung, e.g. 0.5 $\mu$m to 10 $\mu$m.

The product is filled into suitable pressurised multi-dose containers delivering 100 $\mu$l pr. dose.

Other propellants such as dichlorodifluoromethane, dichlorotetrafluoroethane and trichlorofluoromethane or mixtures of these may be used.

Glidants such as oleic acid and derivatives and isopropyl myristate or mixtures of these may be used to reduce friction during administration.

B. Liquid for Nebulisation

| Composition | | |
|---|---|---|
| I | Midodrine HCl | 2.5 g |
| II | Sodium edetate | 0.5 g |
|  | Disodium hydrogen phosphate dihydrate | 2.0 g |
|  | Sodium dihydrogen phosphate dihydrate | 2.0 g |
| III | Purified water | 900.0 g |
| IV | Purified water | ad 1000.0 g |

I is dissolved in III upon continuous stirring The remaining solid ingredients (II) are added to the solution one by one during continuous stirring. Following complete dissolution of the solids, purified water is added to a total weight of 1000.0 g. The composition is filled into 2 ml ampoules or other suitable unit-dose containers.

Excipients may be added to increase the solubility of midodrine, such as polyethylene glycol, alcohol, glycofurol, phospholipids, poloxamer, polyoxyethylene castor oil derivatives, polysorbates, propylene glycol and cyclodextrins or combinations of these. Tonicity agents may be e.g dextrose, glycerol, sorbitol, mannitol, sodium chloride, potassium nitrate and sodium sulphate decahydrate or mixtures thereof.

pH may be adjusted to the appropiate value by use of additional buffer salts such as citric acid, sodium citrate, and potassium dihydrogen phosphate or mixtures of these. Sufficient microbiological preservation may be achieved by addition of benzalconium chloride or parabenes. Suitable flavors can be added to the composition and the taste can be further adjusted by use of sweeteners such as saccharin, acesulfame, aspartame, cyclamate salts or mixtures of these.

Example 19
Powder Composition for Pulmonal Delivery

| | Composition | |
|---|---|---|
| I | Midodrine HCl | 500.0 g |
| II | Glucose | 500.0 g |

The particle size distributions for the ingredients should be appropiate for deposition of the composition in the lung, e.g. 0.5 μm to 10 μm. I and II are carefully mixed and sieved. The powder is filled into capsules or other suitable unit-dose containers, each containing 10 mg of the composition.

Other suspending agents such as lactose, celluloses, starches (maize-, rice-, potato-) calcium phosphate or mixtures of these may be used.

Example 20

Nasal Compositions

General Description of a Nasal Composition

A nasal composition of midodrine is buffered, and tonicity adjusted and it can be delivered from a device, which may or may not require the presence of antimicrobial agents in the composition. The amount of midodrine reaching the systemic circulation may be increased by addition of absorption enhancer(s) to the composition.

The Variability of a Nasal Composition

The total amount of absorption enhancers included in the composition will, typically, vary between 0.01% and 10%. However, some absorption enhancers may also serve as vehicles and thereby totally replace the content of water in the composition. One can include one, two or several absorption enhancing agents in the composition. The final nasal composition may be a homogenous liquid, a suspension, an emulsion, a gel or a powder. The dose administered intranasally may be adjusted by choice of the volume of the formulation, ranging from 10 μl to 250 μl per nostril or of the mass of the composition, ranging from 5 mg to 50 mg.

Specific Examples of Nasal Compositions

Example 20.1

Nasal Composition without Absorption Enhancer

| Composition | | | Function of ingr. |
|---|---|---|---|
| I | Midodrine hydrochloride | 50.0 g | Active ingr. |
| II | Sodium edetate | 0.6 g | Stabiliser |
| | Disodium hydrogen phosphate dihydrate | 2.0 g | Buffer component |
| | Sodium dihydrogen phosphate dihydrate | 2.0 g | Buffer component |
| III | Purified water | 900.0 g | Solvent |
| IV | Purified water | ad to 1000.0 g | Solvent |

I is dissolved in III upon continues stirring. The remaining solid ingredients (II) are added to the solution one by one during continuos stirring. Following complete dissolution of the solids, purified water is added to a total weight of 1000.0 g.

The composition is filled into appropriate nasal spray devices delivering 100 μl pr.dose.

pH may be adjusted to the appropriate value by use of additional buffer salts such as citric acid, sodium citrate and potassium dihydrogen phosphate or mixtures of these. Sufficient microbiological preservation may be achieved by addition of benzalconium chloride, sorbic acid or parabenes such as methylparaben, ethylparaben, propylparaben and butylparaben or mixtures of these.

Example 20.2

Nasal Composition with Absorption Enhancer

| Composition | | | Function of ingr. |
|---|---|---|---|
| I | Midodrine hydrochloride | 50.0 g | Active ingr. |
| II | Sodium glycocholate | 5.0 g | Abs. enhancer |
| III | Sodium edetate | 0.5 g | Stabiliser |
| | Disodium hydrogen phosphate dihydrate | 2.0 g | Buffer component |
| | Sodium dihydrogen phosphate dihydrate | 2.0 g | Buffer component |
| IV | Purified water | 900.0 g | Solvent |
| V | Purified water | to 1000.0 g | Solvent |

II is dissolved in IV, and I is added upon continuous stirring. The remaining solid ingredients (III) are added to the solution one by one during continuos stirring. Following complete dissolution of the solids, purified water is added to a total weight of 1000.0 g.

The composition is filled into appropriate nasal spray devices delivering 100 μl pr.dose.

One, two or several of the absorption enhancers sodium cholate, sodium deoxycholate, sodium taurocholate, sodium taurodeoxycholate, sodium glycodeoxycholate, α-cyclodextrin, β-cyclodextrin, γ-cyclodextrin, methyl cyclodextrin, hydroxypropyl-β-cyclodextrin, dimethyl-β-cyclodextrin, sodium taurodihydrofusidate, phosphatidylcholines, chitin, chitosan, hyaluronic acid, polyetylene glycols, starch microspheres and dextran microspheres may be included in the composition.

pH may be adjusted to the appropriate value by use of additional buffer salts such as citric acid, sodium citrate and potassium dihydrogen phosphate or mixtures of these, Sufficient microbiological preservation may be achieved by addition of benzalconium chloride, sorbic acid or parabenes such as methylparaben, ethylparaben, propylparaben and butylparaben or mixtures of these.

General Description of a Composition Containing Liposomes

Liposomes, or lipid vesicles, are spherical self-closed structures composed of concentric bilayers that entrap part of the solvent or active drug substance in the central core or in the bilayer depending on the hydrophilicity of the active drug substance. Liposomes are predominantly made of natural amphiphilic lipids, e.g. phospolipids. Liposomes are likely to enhance the penetration of the active ingredient into the mucosa such as, e.g. the nasal, buccal, oral, rectal or vaginal mucosa.

Description of the Variability of a Liposomal Composition

The liposomes can be based on liposome forming lipids and liposome stabilising or destabilising lipids. The total amount of lipids in the composition can vary between 20–80% w/w. The ratio between liposome forming lipids and stabilising/destabilising lipids can be between 1:1 to 40:1 (on a molar basis) or the composition can contain liposome forming lipids alone. One can include one, two or several liposome forming lipids in the composition.

Example 20.3
Nasal Composition with Liposomes

| Composition | | | Function of ingr. |
|---|---|---|---|
| I | Midodrine hydrochloride | 50.0 g | Active ingr. |
| | Disodium hydrogen phosphate dihydrate | 2.0 g | Buffer component |
| | Sodium dihydrogen phosphate dihydrate | 2.0 g | Buffer component |
| II | Purified water | 900.0 g | Solvent |
| III | Purified water | to 1000.0 g | Solvent |
| IV | DSPC | 300.0 g | Liposome forming |
| | CH | 84.0 g | Liposome stabiliser/destabiliser |

I is dissolved in II upon continuos stirring. Following complete dissolution of the solids, purified water is added to a total weight of 1000.0 g.

The dry mix of DSPC:CH (7 mol DSPC:2 mol CH) (IV) is dispersed in water, and dehydrated. The liquid composition containing midodrine hydrochloride is poured into the dehydrated DSPC:CH during vigorous stirring to rehydrate the mixture of DSPC:CH.

pH may be adjusted to the appropriate value by use of additional buffer salts such as citric acid, sodium citrate and potassium dihydrogen phosphate or mixtures of these. Sodium edetate may be added to the compositionas stabiliser. Sufficient microbiological preservation may be achieved by addition of sorbic acid or parabenes such as methylparaben, ethylparaben, propylparaben and butylparaben. Propylene glycol (10%) can be added to potentiate the antimicrobial activty of the parabens in the presence of some amphiphilics.

The composition is filled into appropriate nasal spray devices delivering the desired dose. The volume of the dose can be between 10–250 $\mu$l, preferably 100 $\mu$l. The dose can also be administrered by application of two puffs, one in each nostril.

Other vesicle forming lipids can also be used instead of DSPC in the lipid bilayer. These amphiphilic lipids may be cationic, anionic or neutral, such as DPPC, DLPC, DOPC, DSEPC, dialkyl ($C_8$–$C_{20}$) sulfosuccinate or fatty alcohol ethoxylate (with alkyl chain length of $C_8$–$C_{20}$ and 4 to 6 ethoxy groups). The molecular amount of lipids compared to active compound can be optimised with different liposome building lipids.

CH can be replaced by cholesterol derivatives or any other stabiliser/destabiliser such as alkyl ($C_8$–$C_{20}$) phosphate, alkyl ($C_8$–$C_{20}$) sulfate, alkyl ($C_8$–$C_{20}$) ethersulfate, alkyl ($C_8$–$C_{20}$) ether carboxylate. Further stabilisers/destabilisers can be employed such as stearoyl lysophosphatidyl choline, lysophosphatidylcholine, palmitoyl lysophosphatidyl choline and didecanoyl phosphatidyl choline.

Example 21
Buccal Compositions
General Description of a Buccal Composition A buccal formulation of midodrine is buffered and tonicity adjusted and can be delivered from a device, which may or may not require the presence of antimicrobial agents in the formulation. The amount of midodrine reaching the systemic circulation may be increased by addition of absorption enhancer(s) to the composition.

The Variability of the Buccal Composition

The total amount of absorption enhancers included in the formulation will, typically, vary between 0.01% and 10%. However, some absorption enhancers may also serve as vehicles and thereby totally replace the content of water in the formulation. One can include one, two or several absorption enhancing agents in the formulation. The final buccal formulation may be a homogenous liquid, a suspension, an emulsion, a gel or a powder. The dose administered buccally may be adjusted by choice of the volume of the formulation, ranging from 10 $\mu$l to 500 $\mu$l or the mass of the formulation, ranging from 5 mg to 100 mg.

Example 21.1
Buccal Formulation with Liposomes

| Composition | | | Function of ingr. |
|---|---|---|---|
| I | Midodrine hydrochloride | 50.0 g | Active ingr. |
| | Disodium hydrogen phosphate dihydrate | 2.0 g | Buffer component |
| | Sodium dihydrogen phosphate dihydrate | 2.0 g | Buffer component |
| II | Purified water | 900.0 g | Solvent |
| III | Purified water | to 1000.0 g | Solvent |
| IV | DSPC | 300.0 g | Liposome forming |
| | CH | 84.0 g | Liposome stabiliser/destabiliser |

I is dissolved in II upon continuos stirring. Following complete dissolution of the solids, purified water is added to a total weight of 1000.0 g.

The dry mix of DSPC:CH (7 mol DSPC:2 mol CH) (IV) is dispersed in water, and dehydrated. The liquid composition containing midodrine hydrochloride is poured into the dehydrated DSPC:CH during vigorous stirring to rehydrate the mixture of DSPC:CH.

pH may be adjusted to the appropriate value by use of additional buffer salts such as citric acid, sodium citrate and potassium dihydrogen phosphate or mixtures of these. Sodium edetate may be added to the composition as stabiliser. Sufficient microbiological preservation may be achieved by addition of sorbic acid or parabenes such as methylparaben, ethylparaben, propylparaben and butylparaben. Propylene glycol (10%) can be added to potentiate the antimicrobial activty of the parabens in the presence of some amphiphilics.

The composition is filled into appropriate nasal spray devices delivering the desired dose. The volume of the dose can be between 10–500 $\mu$l or the dose can be administrered by application of multiple puffs.

Other vesicle forming lipids can also be used instead of DSPC in the lipid bilayer. These amphiphilic lipids may be cationic, anionic or neutral, such as DPPC, DLPC, DOPC, DSEPC, dialkyl ($C_8$–$C_{20}$) sulfosuccinate or fatty alcohol ethoxylate (with alkyl chain length of $C_8$–$C_{20}$ and 4 to 6 ethoxy groups). The molecular amount of lipids compared to active compound can be optimised with different liposome building lipids.

CH can be replaced by cholesterol derivatives or another stabiliser/destabiliser such as alkyl ($C_8$–$C_{20}$) phosphate, alkyl ($C_8$–$C_{20}$) sulfate, alkyl ($C_8$–$C_{20}$) ethersulfate, alkyl ($C_8$–$C_{20}$) ether carboxylate.

| LIST OF ABBREVIATIONS | |
|---|---|
| CH | cholesterol |
| DSPC | distearoyl glycero phosphatidyl choline |

-continued

LIST OF ABBREVIATIONS

| | |
|---|---|
| DSEPC | distearoyl glysero ethyl phosphatidyl choline |
| DPPC | dipalmitoyl phosphatidyl choline |
| DLPC | dilauroyl phosphatidyl choline |
| DOPC | dioleoyl phosphatidyl choline |
| PC | phosphatidyl choline |

Example 21.2
Buccal Composition Without Absorption Enhancer

| Composition | | | Function of ingr. |
|---|---|---|---|
| I | Midodrine hydrochloride | 50.0 g | Active ingr. |
| II | Sodium edetate | 0.5 g | Stabiliser |
| | Disodium hydrogen phosphate dihydrate | 2.0 g | Buffer component |
| | Sodium dihydrogen phosphate dihydrate | 2.0 g | Buffer component |
| III | Purified water | 900.0 g | Solvent |
| IV | Purified water | to 1000.0 g | Solvent |

I is dissolved in III upon continuos stirring. The remaining solid ingredients (II) are added to the solution one by one during continuos stirring. Following complete dissolution of the solids, purified water is added to a total weight of 1000.0 g.

The composition is filled into appropriate buccal spray devices delivering 100 μl pr.dose, pH may be adjusted to the appropriate value by use of additional buffer salts such as citric acid, sodium citrate and potassium dihydrogen phosphate or mixtures of these. Sufficient microbiological preservation may be achieved by addition of benzalconium chloride, sorbic acid or parabenes such as methylparaben, ethylparaben, propylparaben and butylparaben or mixtures of these.

Example 21.3
Buccal Composition With Absorption Enhancer

| Composition | | | Function of ingr. |
|---|---|---|---|
| I | Midodrine hydrochloride | 50.0 g | Active ingr. |
| II | Sodium glycocholate | 5.0 g | Abs. enhancer |
| III | Sodium edetate | 0.5 g | Stabiliser |
| | Disodium hydrogen phosphate dihydrate | 2.0 g | Buffer component |
| | Sodium dihydrogen phosphate dihydrate | 2.0 g | Buffer component |
| IV | Purified water | 900.0 g | Solvent |
| V | Purified water | to 1000.0 g | Solvent |

II is dissolved in IV, and I is added upon continuous stirring. The remaining solid ingredients (III) are added to the solution one by one during continues stirring. Following complete dissolution of the solids, purified water is added to a total weight of 1000.0 g.

The composition is filled into appropriate buccal spray devices delivering 100 μl pr.dose.

One, two or several of the absorption enhancers sodium cholate, sodium deoxycholate, sodium taurocholate, sodium taurodeoxycholate, sodium glycodeoxycholate, α-cyclodextrin, β-cyclodextrin, γ-cyclodextrin, methyl cyclodextrin, hydroxypropyl-β-cyclodextrin, dimethyl-β-cyclodextrin, sodium taurodihydrofusidate, phosphatidylcholines, chitin, chitosan, hyaluronic acid, polystyrene glycols, starch microspheres and dextran microspheres may be included in the composition.

pH may be adjusted to the appropriate value by use of additional buffer salts such as citric acid, sodium citrate and potassium dihydrogen phosphate or mixtures of these. Sufficient microbiological preservation may be achieved by addition of benzalconium chloride, sorbic acid or parabenes such as methylparaben, ethylparaben, propylparaben and butylparaben or mixtures of these.

Example 22
Midodrine Sublingual Tablets
General Description

Sublingual tablets are designed to give a fast disintegration in the mouth by the amount of salvia normally available in that region. The disintegration time is therefore very short or short and there may be additives, which promote salvia secreting in the composition.

A fast disintegration together with a high solubility of the drug substance give the possibility of a fast absorption through the mucous membrane of the mouth, especially under the tongue where the blood vessels run close to the surface.

Sublingual absorbed drugs avoid more or less the first pass liver metabolism.

Description of Variability in Sublingual Compositions

Sublingual tablets may be prepared by mould technique, by direct compression or by conventional wet granulation or dry granulation (e.g. roller compaction) of the ingredients. As mentioned, taste improving substances may be added to promote salvia secretion. This may include artificial sweeteners (cyclamate, saccharinsodium, aspartame, etc.), natural sweeteners (saccharose, sorbitol, xylitol, etc.), week organic acids (citric, acetic- ascorbic acid, ect.) natural or artificial flavours (strawberry, black currant, ananas, apple, orange, lemon, etc.) in the below mentioned compositions.

Example 22.1

| | | | | Function |
|---|---|---|---|---|
| I | Midodrine hydrochloride | 2.5 g | 5.0 g | Active ingr. |
| II | Purified water | | | Solvent |
| | Ethanol 96% equal parts | q.s. | q.s. | Moist. agent |
| III | Lactose | 52.5 g | 50 g | Filler |
| | Mannitol | 45 g | 45 g | Filler |

The amounts of lactose and mannitol may be varied from 25 to about 100 g. Dose 100 mg (50–200 mg) corresponds to 2.5 or 5.0 mg midodrine hydrochloride of the two compositions, respectively.

Disintegration time is extremely short (2–5 sec).

II is prepared, and I is dissolved in II. The solution is incorporated in III to a homogenious mixture is achived. More II may be added.

The moistured mass is spread on a suitable plate equiped with wholes into which the mass is pressed and which have a depth that gives the wanted dose of drug substance. The wet mass is pressed out of the wholes and allowed to dry before further handling. (Sublingual tablet preparation by mould-technique).

II may be replaced by mixtures of different volatile organic solvents and may have a water content of 0–90%. III may be replaced by different mixtures of solubile pharmaceutically acceptable excipients as sorbitol, mannitol, xylitol, maltodextrin, lycasin, lactitol etc.

Example 22.2

|     |                            |        |        | Function         |
| --- | -------------------------- | ------ | ------ | ---------------- |
| I   | Midodrine hydrochloride    | 2.5 g  | 5.0 g  | active ingr.     |
| II  | Tablettose                 | 55.0 g | 55.0 g | filler           |
| III | Cellulose, microcryst. Type 102 | 10.0 g | 10.0 g | filler/binder    |
| IV  | Agar sieve 180             | 5.0 g  | 5.0 g  | disintegrant     |
| V   | Magnesium stearate         | 0.5 g  | 0.5 g  | glidant/lubricant |
|     | Talc                       | 4.5 g  | 4.5 g  | glidant/lubricant |

I is mixed with II and further with III, IV and V and compressed into tablets.

The amount of the filler, tablettose, may vary from 25 to 75 g, the filler/binder (cellulose) may vary from 5 to 25 g, the disintegrant from 1 to 15 g, magnesium stearate from 0.1 to 2.5 g and talc from 1.0 to 10 g.

Mass weight of 73 mg corresponds to a dose of 2.5 mg or mass weight of 75.5 mg corresponds to a dose of 5.0 mg midodrine hydrochloride in the two compositions, respectively.

Disintegration time is short (30 sec–4 min).

Tablettose may be replaced by other qualifies of lactose with good flowability. Agar may be replaced by other disintergrants as croscarmellose sodium/calcium or the like, crosspovidone, starch glycolate, alginates or other disintegrants. Magnesium stearate may be replaced by other glidants as different types of silica colloidal hydrous or anhydrous, Ca-stearate, stearic acid, sodium stearylfumarate, cotton-seed oil, hydrogenated vegetable oils or other suitable lipid substances as e.g. Myvatex.

Example 22.3

|     |                         |       |       | Function     |
| --- | ----------------------- | ----- | ----- | ------------ |
| I   | Midodrine hydrochloride | 2.5 g | 5.0 g | active ingr. |
| II  | Maize starch            | 9.5 g | 7.0 g | filler       |
|     | Lactose                 | 66 g  | 66 g  | filler       |
| III | Povidone 30             | 2.5 g | 2.5 g | binder       |
| IV  | Purified water          | q.s.  | q.s.  | solvent      |
| V   | Mannitol                | 36 g  | 36 g  | filler/taste |
| VI  | Magnesium stearate      | 1.5 g | 1.5 g | lubricant    |

I is mixed with II and granulated with III dissolved in IV. More IV may be added. After drying, V and VI are added and tablets are compressed.

The amount of maize starch may vary from 5 to 15 g, lactose from 30 to 100 g, mannitol from 10 to 80 g, and magnesium stearate from 0.5 to 5 g.

Disintegration time is about 5 min.

Maize starch may be replaced by other suitable starches as rice- or potato starch. Lactose may be replaced by maltodextrine, dextrin etc. Povidone 30 may be replaced by povidone VA 64 or 90 or gelatine or pregelatinized starch or different types of cellulose (methylcellulose, hydroxypropyl cellulose etc.). Mannitol may be replaced by sorbitol, xylitol, maltitol, maltodextrin, lactitol, etc. Magnesium stearate may be replaced by other glidants as different types of colloidal silica hydrous or anhydrous, Ca-stearate, stearic acid, sodium stearylfumarate, cotton-seed oil, hydrogenated vegetable oils or other suitable lipid substances as e.g. Myvatex.

Example 23
Midodrine Melt Tablets
General Description of Melt Tablets

Melt-tablets are also referred to as fast/rapidly-disintegrating tablets, dispersing tablets and dissolving tablets. In this example, the term "melt-tablet" is applied.

Melt-tablets are a tablet dosage form for oral administration, one that disintegrates instantaneously and releasing the drug, which dissolves or disperse rapidly in saliva and afterwards swallowed without the need for water. The drug is absorbed in the normal way.

Less frequently melt-tablets are designed to be absorbed through the buccal mucosa. In that case the bioavailability of the drug from the melt-tablet may be even greater than observed for standard dosage forms. Further more side-effects may be reduced if they are caused by first-pass metabolites.

A Description of the Variability of the Melt-Tablets

Techniques currently applied for formulate melt-tablets are namely freeze-drying (lyophilisation), spray drying, tablet molding and direct compression. In this example only melt-tablets prepared by lyophilisation are described.

To ensure melt-tablets fast-disintegrating and dissolving attribute water must quickly progress into the tablet matrix to cause rapid disintegration and instantaneous dissolution of the tablet. Maximising the porous structure of the tablet matrix and incorporating appropriate disintegrating agent and/or highly water-soluble excipients in the tablet formulation are the basic approaches applied in the current melt-tablet technologies.

In the formulation the total amount of disintegrating agents and/or highly water-soluble excipients can vary between 5–80% (w/v) and the total amount of binding agents can vary between 0.05–5% (w/v). Water is used to ensure the porous structure. Sufficient microbiological preservatives (benzoic acid, methylparaben etc.) may be added to prevent microbiological growth of the aqueous solution during production. When the product has been dried, the preservative has no further function.

Taste improving agents may be added to promote salvia secretion. This may include artificial sweeteners (aspartame, cyclamate, saccharin etc.), natural sweeteners (sucrose, sorbitol, xylitol etc.) week organic acids (citric-, ascorbic acid etc.), natural or artificial flavours (strawberry, black currant, pineapple, apple, orange, lemon etc.). Colouring agents may also be added to give the melt-tablets elegance and identity.

Permeation enhancers (sodium lauryl sulphate etc.) may be added to optimise the transmucosal absorption and pH-adjusting excipients (hydrochloride, sodium hydroxide etc.) may be used to optimise the chemical stability of the drug. Collapse protecting agents (glycine etc.) to prevent the shrinkage of the tablet during lyophilisation process or during long-term storage.

Melt-Tablet Prepared by Lyophilisation

| Composition |                         |       | Function of ingredient |
| ----------- | ----------------------- | ----- | ---------------------- |
| I           | Midodrine hydrochloride | 5.0 g | Active                 |
| II          | Maltodextrin            | 200 g | Water-soluble          |
| III         | Xanthan gum             | 20 g  | Binding agent          |
| IV          | Purified water          | 775 g | Solvent                |

II and III are dissolved in IV upon continues stirring and I is added to the solution during stirring. Purified water is added to a total weight of 1000.0 gram.

The solution is filled in PVC blister with a diameter of 15 mm and a depth of 6 mm, so the resulting dose of midodrine hydrochloride is 5 mg pr. tablet.

The blisters are placed on the shelves of the freeze-dryer. Samples are frozen to −45° C. at a rate of 0.5° C./min and kept at this temperature for 1.5 hour. Primarily, drying is performed by keeping the blisters for 8 hour at a pressure of 1 mbar, a shelf temperature of −10° C., and a condensor temperature of −60° C.

Reducing the pressure to 0.1 mbar, carrying out secondary drying and increasing the shelf temperature to 25° C. Secondary drying time is 6 hour. Lyophilisation is terminated by venting the drying chamber with air.

II may be replaced by lactose, mannitol, dextrose, xylitol, fructose, sucrose, maltose, sorbitol etc. or mixtures of these. As disintegrating agent croscarmellose, crospovidone etc. may be added. Other excipients may also be used instead of III. These excipients may be gelatine, tragacanth gum, agar, acacia, alginate, dextran, povidone, hydroxyethylcellulose etc. or mixtures of these.

Example 24
Midodrine Rectal Compositions
General Description

Rectal solution is a way of drug administration free of the condition of the patient. Further a quite quick onset of effect is seen for some compositions. A major part of the absorbed dose do not undergo first pass metabolism, which in some cases may be of some advantage.

Description of Variability in Composition

The amount of rectal solution to give one dose is kept on the small amount of 1–4 ml such as, e.g., 2.0 ml. This is to avoid any emptying reflex from the rectum mucosa. The solution will be dispensed in a suitable container as a single-dose syringer or sealed plastic tube. Both equipped with a suitable tip.

A solution with high content of pharmaceutical acceptable organic solvent to promote absorption have been chosen as one example, a simple aquous isotonic solution as one, a simple slightly viscous aquous isotonic as one example and finally a aquous pH-adjusted aquous isotonic solution has been chosen as the last example.

Example 24.1

| | | | Function |
|---|---|---|---|
| Midodrine hydrochloride | 1.25 g | 2.50 g | active ingr. |
| Glycerol 85% | 500 g | 500 g | solvent/abs. enhancer |
| Purified water up to | 1000 ml | 1000 ml | solvent |

One dose of 2.0 ml=2.5 mg midodrine hydrochloride or 2.0 ml=5.0 mg midodrine hydrochloride. Glycerol may be exchanged with glycofurol, polythylene glycols 200 to 600, propylene glycol or similar non-irritant suitable solvent. The amount of glycerol may vary from about 200 to 800 g.

Example 24.2

| | | | Function |
|---|---|---|---|
| Midodrine hydrochloride | 1.25 g | 2.50 g | active ingr. |
| Sodium chloride | 9.0 g | 9.0 g | isotonic agent |
| Propylis paraoxibenzoas | 0.2 g | 0.2 g | preservative |
| Methylis paraoxibenzoas | 0.8 g | 0.8 g | preservative |
| Purified water up to | 1000 ml | 1000 ml | solvent |

The mixture of paraoxibenzoates may be exchanged with other suitable preservatives.

Dose 2.0 ml=2.5 mg midodrine hydrochloride or 2.0 ml=5.0 mg midodrine hydrochloride

Example 24.3

| | | | Function |
|---|---|---|---|
| Midodrine hydrochloride | 1.25 g | 2.50 g | active ingr. |
| Propylis paraoxibenzoas | 0.2 g | 0.2 g | preservative |
| Methylis paraoxibenzoas | 0.8 g | 0.8 g | preservative |
| Sodium carboxymethylcellulose | 6.0 g | 6.0 g | viscosity incr. agent |
| Purified water up to | 1000 ml | 1000 ml | solvent |

Dose 2.0 ml=2.0 mg midodrine hydrochloride or 2.0 ml=5.0 mg midodrine hydrochloride. The amount of viscosity increasing agent may vary from about 2 to about 8 g.

Example 24.4

| | | | Function |
|---|---|---|---|
| Midodrine hydrochloride | 1.25 g | 2.50 g | active ingr. |
| Sodium acetate | 1.0 g | 1.0 g | buffer agent |
| Sodium chloride | 8.5 g | 8.5 g | isotonic agent |
| Propylis paraoxibenzoate | 0.2 g | 0.2 g | preservative |
| Methylis paraoxibenzoate | 0.8 g | 0.8 g | preservative |
| Purified water up to | 1000 ml | 1000 ml | solvent |

The mixture of parabenzoates may be exchanged by other suitable preservative. Sodium acetate may be exchanged by other suitable pH regulating substance or a buffer mixture with pH in the interval of 7.0–8.0. The amount of buffer agent may vary from about 0.5 to about 3.0 g.

Dose 2.0 ml=2.5 mg midodrine hydrochloride or 2.0 ml=5.0 mg

What is claimed is:

1. A pharmaceutical kit comprising
   a) a controlled release pharmaceutical composition for oral use comprising midodrine (ST 1085) or a pharmaceutically acceptable salt thereof and/or its active metabolite desglymidodrine (ST 1059) or a pharmaceutically acceptable salt thereof,
   wherein the in vitro release rate of midodrine and/or desglymidodrine has the following properties:
      i) a relatively fast first initial release followed by
      ii) a steady release or a slower release than in step i) above, which is followed by
      iii) a second rise in release rate that takes place 5–10 hours after start of an in vitro dissolution test and, finally,
      iv) a decline in release rate so that a relatively fast peak plasma concentration of midodrine and/desglymidodrine is obtained within about 15 minutes–6 hours after administration of the composition, and a therapeutically effective plasma concentration of midodrine and/or desglymidodrine is maintained for at least about 9 hours, and
   b) a relatively fast onset pharmaceutical composition comprising midodrine (ST 1085) or a pharmaceutically acceptable salt thereof and/or its active metabolite desglymidodrine (ST 1059) or a pharmaceutically acceptable salt thereof, the composition being adapted to provide midodrine and/or desglymidodrine in such a manner that a relatively fast therapeutically effective concentration of desglymidodrine is obtained within about 15 minutes to about 6 hours.

2. The kit according to claim 1, wherein steady release starts about 1–3 hours after start of the in vitro dissolution test.

3. The kit according to claim 1, wherein steady release from the controlled release composition is maintained for at least 2 hours.

4. A pharmaceutical kit comprising
a) a controlled release pharmaceutical composition for oral use comprising midodrine (ST 1085) or a pharmaceutically acceptable salt thereof and/or its active metabolite desglymidodrine (ST 1059) or a pharmaceutically acceptable salt thereof, wherein the release rate of midodrine and/or desglymidodrine in an in vitro dissolution test has the following properties:
   i) a relatively fast first initial release within about 15 minutes to 6 hours followed by
   ii) a steady release or a slower release than in step i) above, which is followed by
   iii) a second rise in release rate that takes place 5–10 hours after start of an in vitro test and,
   iv) a decline in release rate and wherein the release pattern of midodrine and/or desglymidodrine from the composition in the in vitro dissolution test-is as follows (±30% w/w of the values stated below):
      about 25% w/w is released about 30 minutes after start of the test,
      about 35% w/w is released about 1 hour after start of the test,
      about 39% w/w is released about 2 hours after start of the test,
      about 47% w/w is released about 3 hours after start of the test,
      about 53–56% is released about 4 hours after start of the test,
      about 66–72% w/w is released about 6 hours after start of the test,
      about 80–85% w/w is released about 8 hours after start of the test,
      about 93% w/w is released about 10 hours after start of the test,
      about 100% w/w is released about 12 hours after start of the test, and
b) a relatively fast onset pharmaceutical composition comprising midodrine (ST 1085) or a pharmaceutically acceptable salt thereof and/or its active metabolite desglymidodrine (ST 1059) or a pharmaceutically acceptable salt thereof, the composition being adapted to provide midodrine and/or desglymidodrine in such a manner that a relatively fast therapeutically effective concentration of desglymidodrine is obtained within about 15 minutes to 6 hours after administration of the composition.

5. A pharmaceutical kit comprising
a) a controlled release pharmaceutical composition for oral use comprising midodrine (ST 1085) or a pharmaceutically acceptable salt thereof and/or its active metabolite desglymidodrine (ST 1059) or a pharmaceutically acceptable salt thereof, wherein the in vitro release rate of midodrine and/or desglymidodrine has the following course of events
   i) a relatively fast first initial release within about 15 minutes to about 6 hours followed by
   ii) a steady release or a slower release than in step i) above, which is followed by
   iii) a second rise in release rate that takes place 5–10 hours after start of an in vitro dissolution test and,
   iv) a decline in release rate and wherein the release pattern of midodrine and/or desglymidodrine from the composition when tested in vitro is as follows (±30% w/w of the values stated below):
      about 28% w/w is released about 30 minutes after start of the test,
      about 35% w/w is released about 1 hour after start of the test,
      about 41% w/w is released about 2 hours after start of the test,
      about 45% w/w is released about 3 hours after start of the test,
      about 55% w/w is released about 4 hours after start of the test,
      about 70 w/w is released about 6 hours after start of the test,
      about 78% w/w is released about 7 hours after start of the test,
      about 90% w/w is released about 8 hours after start of the test,
      about 95% w/w is released about 10 hours after start of the test,
      about 100% w/w is released about 12 hours after start of the test, and
b) a relatively fast onset pharmaceutical composition comprising midodrine (ST 1085) or a pharmaceutically acceptable salt thereof and/or its active metabolite desglymidodrine (ST 1059) or a pharmaceutically acceptable salt thereof, the composition being adapted to provide midodrine and/or desglymidodrine in such a manner that a relatively fast therapeutically effective concentration of desglymidodrine is obtained after administration of the composition.

6. The kit according to claim 4 or 5, wherein the controlled release composition upon administration results in a relatively fast peak plasma concentration of desglymidodrine, and a therapeutically effective plasma concentration of desglymidodrine is maintained for at least about 9 hours.

7. The kit according to claim 6, wherein the steady release period ii) from the controlled release composition, starts about 1–3 hours after start of the dissolution test.

8. The kit according to claim 6, wherein the steady release period ii) from the controlled release composition is maintained for at least about 2 hours.

9. A pharmaceutical kit comprising:
a) a controlled release pharmaceutical composition for oral use comprising midodrine (ST 1085) or a pharmaceutically acceptable salt thereof and/or its active metabolite desglymidodrine (ST 1059) or a pharmaceutically acceptable salt thereof, the composition being adapted to release midodrine and/or desglymidodrine in such a manner that a relatively fast peak plasma concentration of desglymidodrine is obtained within about 15 minutes to about 6 hours and a therapeutically effective plasma concentration of desglymidodrine is maintained for at least about 9 hours, and
b) a relatively fast onset pharmaceutical composition comprising midodrine (ST 1085) or a pharmaceutically acceptable salt thereof and/or its active metabolite desglymidodrine (ST 1059) or a pharmaceutically acceptable salt thereof, the composition having a disintegration time of at the most 2 minutes so as to provide midodrine and/or desglymidodrine in such a manner that a relatively fast therapeutically effective concentration of desglymidodrine is obtained within about 15 minutes to about 6 hours after administration of the composition.

10. The kit according to any one of the claims 1 to 5, wherein the relatively fast onset composition has a disintegration time of at the most 2 minutes.

11. The kit according to claim 1, wherein the plasma concentration of desglymidodrine from the controlled release composition is maintained at a therapeutically active level for about 4.5–16 hours.

12. The kit according to claim 11, wherein the relatively constant level n is ±60%, and wherein n is the plasma concentration in ng/ml and monitored in healthy persons.

13. The kit according to any one of claims 1–5 and 9 containing midodrine or a pharmaceutically acceptable salt thereof.

14. The kit according to claim 13, wherein a peak plasma concentration of midodrine from the controlled release composition is obtained 15–90 minutes after oral administration.

15. The kit according to claim 13, wherein the plasma concentration of midodrine from the controlled release composition after oral administration is maintained at a relatively constant level for about 0.7–4 hours.

16. The kit according to claim 15, wherein the relatively constant level m is ±60%, and wherein m is the plasma concentration in ng/ml and monitored in healthy persons.

17. The kit according to claim 13, wherein the release pattern of midodrine from the controlled release composition when tested in an in vitro dissolution test employing a basket according to USP and Ph. Eur, 100 rpm, 600 ml 1 N hydrochloric acid as dissolution medium and a temperature of 37° C., is:

1–15% w/w is released from the composition within the first 30 min after start of the test,
10–35% w/w is released about 30 minutes after start of the test,
15–40% w/w is released about 1 hour after start of the test,
20–50% w/w is released about 2 hours after start of the test,
20–55% w/w is released about 3 hours after start of the test,
25–75% w/w is released about 4 hours after start of the test,
30–74% w/w is released about 6 hours after start of the test,
40–85% w/w is released about 8 hours after start of the test,
65–100% w/w is released about 10 hours after start of the test, and
90–110% w/w is released about 12 hours after start of the test.

18. The kit according to claim 13, wherein the release pattern of midodrine from the controlled release composition when tested in an in vitro dissolution test employing a basket according to USP and Ph. Eur, 100 rpm, a first dissolution medium with a pH of about 1.0 for the first 2 hours of the testing followed by a second dissolution medium with a pH of about 6.0 for the next 5.5 hours, a third dissolution medium with a pH of about 7.5 until the end of the testing, and a temperature of 37 0C is:

1–15% w/w is released from the composition within the first 30 minutes after start of the test,
10–35% w/w is released about 30 minutes after start of the test,
15–40% w/w is released about 1 hour after start of the test
20–50% w/w is released about 2 hours after start of the test,
20–55% w/w is released about 3 hours after start of the test,
25–75% w/w is released about 4 hours after start of the test,
30–74% w/w is released about 6 hours after start of the test,
40–95% w/w is released about 8 hours after start of the test,
65–100% w/w is released about 10 hours after start of the test, and
75–110% w/w is released about 12 hours after start of the test.

19. The kit according to claim 13, wherein the release pattern of midodrine from the controlled release composition when tested using an in vitro dissolution test is:

1–15% w/w is released from the composition within the first 30 minutes after start of the test,
10–35% w/w is released about 30 min after start of the test,
15–40% w/w is released about 1 hour after start of the test,
20–50% w/w is released about 2 hours after start of the test,
20–55% w/w is released about 3 hours after start of the test,
25–75% w/w is released about 4 hours after start of the test,
30–74% w/w is released about 6 hours after start of the test,
35–85% w/w is released about 7 hours after start of the test,
45–95% w/w is released about 8 hours after start of the test,
65–100% w/w is released about 10 hours after start of the test, and
90–110% w/w is released about 12 hours after start of the test.

20. The kit according to claim 13, wherein the release pattern of midodrine from the controlled release composition when tested using an in vitro dissolution test is:

1–15% w/w is released from the composition within the first 30 min after start of the test,
15–35% w/w is released about 30 minutes after start of the test,
20–40% w/w is released about 1 hour after start of the test,
25–50% w/w is released about 2 hours after start of the test,
30–55% w/w is released about 3 hours after start of the test,
40–75% w/w is released about 4 hours after start of the test,
50–74% w/w is released about 6 hours after start of the test,
60–85% w/w is released about 7 hours after start of the test,
70–95% w/w is released about 8 hours after start of the test,
80–100% w/w is released about 10 hours after start of the test, and
90–110% w/w is released about 12 hours after start of the test.

21. The kit according to claim 13, wherein the release pattern of midodrine from the controlled release composition when tested using an in vitro dissolution test is as follows (±30% w/w of the values stated below):
- about 25% w/w is released about 30 minutes after start of the test,
- about 35% w/w is released about 1 hour after start of the test,
- about 39% w/w is released about 2 hours after start of the test,
- about 47% w/w is released about 3 hours after start of the test,
- about 53% w/w is released about 4 hours after start of the test,
- about 66% w/w is released about 6 hours after start of the test,
- about 75% w/w is released about 7 hours after start of the test,
- about 80% w/w is released about 8 hours after start of the test,
- about 90% w/w is released about 10 hours after start of the test, and
- about 100% w/w is released about 12 hours after start of the test.

22. The kit according to claim 13, wherein the release pattern of midodrine from the controlled release composition when tested using an in vitro dissolution test is as follows (±30% w/w of the values stated below):
- about 20% w/w is released about 30 minutes after start of the test,
- about 20% w/w is released about 1 hour after start of the test,
- about 20% w/w is released about 2 hours after start of the test,
- about 20% w/w is released about 3 hours after start of the test,
- about 25% w/w is released about 4 hours after start of the test,
- about 45% w/w is released about 6 hours after start of the test,
- about 75% w/w is released about 7 hours after start of the test,
- about 90% w/w is released about 8 hours after start of the test,
- about 95% w/w is released about 10 hours after start of the test, and
- about 100% w/w is released about 12 hours after start of the test.

23. The kit according to any one of claims 1, 4, 5 and 9, wherein the second rise in release rate from the controlled release composition takes place 5–9 hours after start of the dissolution test.

24. The kit according to claim 23, wherein the second rise in release rate from the controlled release composition takes place about 6.5–9 hours after start of the dissolution test simulating the time it takes to reach the colon after oral administration.

25. The kit according to claim 13, wherein the release rate of midodrine from the controlled release composition when tested using an in vitro dissolution test is as follows (±10–40% of the values stated below):
- about 15–40%/hour about 30 min after start of the test 15–40%/hour),
- about 4–15%/hour about 1 hour after start of the test
- about 2–10%/hour about 2 hours after start of the test,
- about 2–10%/hour about 3 hours after start of the test,
- about 2–15%/hour about 4 hours after start of the test,
- about 2–30% about 6 hours after start of the test,
- about 2–15%/hour about 8 hours after start of the test,
- about 0–10%/hour about 10 hours after start of the test, and
- about 0–10%/hour about 12 hours after start of the test.

26. The kit according to claim 13, wherein the $W_{50}$ of midodrine, defined as corresponding to the time the plasma concentration curve is >50% of the $C_{max}$ value, from the controlled release composition is from about 1 to about 9 hours.

27. The kit according to any one of claims 1, 4, 5 and 9, wherein the $W_{50}$ of desglymidodrine (defined as corresponding to the time the plasma concentration curve is or is above 50% of the $C_{max}$ value) from the controlled release composition is from about 5 to about 12 hours.

28. The kit according to any one of claims 1, 4, 5 and 9, wherein $T_{max}$ for the controlled release composition is increased with a factor of at least 2 when compared with a plain Gutron® tablet administered in the same dose and where $T_{max}$ is determined from a plasma concentration versus time curve and the plasma concentration reflects the sum concentration in nmol/l of midodrine and desglymidodrine.

29. The kit according to any one of claims 1, 4, 5 and 9, wherein MRT (mean residence time) for the controlled release composition is increased with a factor of at least 1.5 when compared with a plain Gutron® tablet administered in the same dose and where MRT is determined from a plasma concentration versus time curve and the plasma concentration reflects the sum concentration in nmol/l of midodrine and desglymidodrine.

30. The kit according to any one of claims 1, 4, 5 and 9, wherein $W_{50}$ is increased with a factor of at least 2 when compared with a plain Gutron® tablet administered in the same dose and where $W_{50}$ is determined from a plasma concentration versus time curve and the plasma concentration reflects the sum concentration in nmol/l of midodrine and desglymidodrine after administration of the controlled release composition.

31. The kit according to any one of claims 1, 4, 5 and 9, wherein $W_{75}$ (C>75% $C_{max}$) is increased with a factor of at least 1.5 when compared with a plain Gutron® tablet administered in the same dose and where $W_{75}$ (C>75% $C_{max}$) is determined from a plasma concentration versus time curve and the plasma concentration reflects the sum concentration in nmol/l of midodrine and desglymidodrine after administration of the controlled release composition.

32. The kit according to any one of claims 1, 4, 5 and 9, wherein the MRT for midodrine from the controlled release composition is at least about 1.5 hours.

33. The kit according to any one of claims 1, 4, 5 and 9, wherein the MRT for desglymidodrine from the controlled release composition is at least about 6 hours.

34. The kit according to any one of claims 1, 4, 5 and 9, wherein midodrine is present in the form of (±)-2-amino-N-(β-hydroxy-2,5-dimethoxyphenethyl)acetamide, (+)-2-amino-N-(β-hydroxy-2,5-dimethoxyphenethyl)acetamide, (−)-2-amino-N-(β-hydroxy-2,5-dimethoxyphenethyl)acetamide or mixtures thereof.

35. The kit according to any one of claims 1, 4, 5 and 9, wherein midodrine is present in the racemic form (RS), in the enantiomeric form (R), in the enantiomeric form (S) or in mixtures thereof.

36. The kit according to claim 34, wherein at least 90% w/w of midodrine is present in the therapeutically active enantiomeric form.

37. The kit according to claim 36, wherein the therapeutically active enantiomeric form of midodrine is (−)-2-amino-N-(β-hydroxy-2,5-dimethoxyphenethyl)acetamide or the (R) form of midodrine.

38. The kit according to any one of claims 1, 4, 5 and 9 containing the active metabolite desglymidodrine (ST 1059), wherein desglymidodrine is present in the form of (±)-α-(aminomethyl)-2,5-dimethoxy-benzenemethanol (±ST 1059), (+)-α-(aminomethyl)-2,5-dimethoxy-benzenemethanol (+ST 1059), (−)-α-(aminomethyl)-2,5-dimethoxy-benzenemethanol (−ST 1059), or mixtures thereof.

39. The kit according to claim 38, wherein desglymidodrine is present in the racemic form (RS), in the enantiomeric form (R), in the enantiomeric form (S) or in mixtures thereof.

40. The kit according to claim 38, wherein at least 90% w/w of desglymidodrine is present in the therapeutically active enantiomeric form.

41. The kit according to claim 40, wherein the therapeutically active enantiomeric form of desglymidodrine is (−)-α-(aminomethyl)-2,5-dimethoxy-benzenemethanol (−ST 1059) or the (R) form of desglymidodrine ((R) ST 1059).

42. The kit according to any one of claims 1, 4, 5 and 9, wherein midodrine and/or desglymidodrine are present in the form of a pharmaceutically acceptable salt which is a salt formed between midodrine and/or desglymidodrine and an inorganic acid selected from the group consisting of a hydrochloride, a hydrobromide, a hydroiodide, a nitrate, a nitrite, a $H_3PO_3$ salt, a $H_3PO_4$ salt, a $H_2SO_3$ salt, a sulfate and a $H_2SO_5$ salt.

43. The kit according to any one of claims 1, 4, 5 and 9, wherein midodrine and/or desglymidodrine are present in the form of a pharmaceutically acceptable salt which is a salt formed between midodrine and/or desglymidodrine and an organic acid such as organic acids like e.g. $H_2CO_3$, acetic acid, $C_2H_5COOH$, $C_3H_7COOH$, $C_4H_9COOH$, $(COOH)_2$, $CH_2(COOH)_2$, $C_2H_5(COOH)_2$, $C_3H_6(COOH)_2$, $C_4H_8(COOH)_2$, $C_5H_{10}(COOH)_2$, fumaric acid, maleic acid, lactic acid, citric ac tartaric acid, ascorbic acid, benzoic acid, salicylic acid and phthalic acid.

44. The kit according to any one of claims 1, 4, 5 and 9, wherein at least one of the controlled release and the relatively fast release composition is in liquid form.

45. The kit according to any one of claims 1, 4, 5 and 9, wherein at least one of the controlled release and the relatively fast release composition is in the form of a solid dosage form.

46. The kit according to claim 45, wherein at least one of the controlled release and the relatively fast release composition is in the form of tablets, capsules, sachets, solid dispersion, crystals and the like.

47. The kit according to claim 46, wherein the controlled release composition comprises at least two parts such as at least a first and a second part, each part contains midodrine and/or, if present, desglymidodrine and the first part being adapted to release midodrine and/or, if present, desglymidodrine, in a controlled manner during the first 0–14 hours after oral intake and the second part being adapted to release midodrine and/or, if present, desglymidodrine, starting at least 6 hours after oral intake.

48. The kit according to claim 47, wherein at least one of the at least two parts is present in the composition in the form of a multiplicity of individual units.

49. The kit according to claim 48, wherein the individual units are pellets or minitablets.

50. The kit according to claim 49, wherein the two parts are in admixture.

51. The kit according to claim 48, wherein the kit comprises a multiple unit dosage form.

52. The kit according to claim 51, wherein the kit is in a multiple unit dosage form, wherein at least one of the at least two parts comprising at least two different types of pellets, the first type of pellets corresponding to a first fraction and the second type of pellets corresponding to a second fraction.

53. The kit according to claim 50, wherein the at least two parts of the composition comprise at least two different types of pellets, the first type of pellets corresponding to the first part and the second type of pellets corresponding to the second part.

54. The kit according to claim 50 wherein the kit is in the form of a multiple unit dosage form comprising at least two different types of minitablets, the first type of minitablets corresponding to the first part and the second type of minitablets corresponding to the second part.

55. The kit according to claim 50 in the form of a multiple unit dosage form, wherein the first or the second part is in the form of minitablets.

56. The kit according to claim 50, wherein the first or the second part is in the form of pellets.

57. The kit according to claim 47, wherein the at least two fractions is present in a tablet.

58. The kit according to claim 57, wherein the tablet is a multilayer tablet and the at least first and the second part are each comprised in a layer in the tablet.

59. The kit according to claim 47 further comprising a third part adapted to release midodrine and, if present, desglymidodrine relatively fast from the composition.

60. The kit according to claim 47 further comprising a fourth part adapted to release midodrine and/or desglymidodrine from the composition 6–10 hours after oral intake.

61. The kit according to claim 47 further comprising a fourth part adapted to release midodrine and/or desglymidodrine from the composition in the colon after oral intake.

62. The kit according to claim 60 or 61, wherein the third and/or, if present, the fourth part comprise pellets or minitablets or are a layer in or on a tablet.

63. The kit according to claim 47, wherein the first part has a release kinetic corresponding to a zero or a first order release, a mixture of zero and first order release, or any other order of release.

64. The kit according to claim 47 wherein the second part has a release kinetic corresponding to a zero or a first order release, a mixture of zero and first order release.

65. The kit according to claim 59, wherein the third fraction has a release kinetic, which corresponds to that of a plain release tablet.

66. The kit according to any one of claims 1, 4, 5 and 9, wherein at least one of the controlled release and the relative fast release composition comprises one or more further active drug substances.

67. The kit according to any one of claims 1, 4, 5 and 9, wherein the relatively fast onset composition or part of the kit results in a peak or shoulder plasma concentration within 90 minutes upon administration of the relatively fast onset composition.

68. The kit according to any one of claims 1, 4, 5 and 9, wherein the relatively fast onset composition is a nasal composition.

69. The kit according to claim 68, wherein the nasal composition comprises polyethyleneglycol and/or glycofurol as a nasal vehicle.

70. The kit according to claim 69, wherein the polyethyleneglycol is PEG 200 and/or PEG 300.

71. The kit according to any one of claims 1, 4, 5 and 9, wherein the relatively fast onset composition is in the form of a liposomal composition.

72. The kit according to any one of claims 1, 4, 5 and 9, wherein the relatively fast onset composition is in the form of a tablet which is a melt tablet or sublingual tablet.

73. The kit according to any one of claims 1, 4, 5 and 9, wherein the relatively fast onset composition is a buccal, oral, or rectal composition.

74. The pharmaceutical kit according to any one of claims 1, 4, 5 and 9, wherein the midodrine and/or desglymidodrine in relatively fast onset composition is present in an amount of from 0.2 mg to 10 mg.

75. The pharmaceutical kit according to claim 1, wherein the therapeutically effective plasma concentration of desglymidodrine is maintained for at least about 10 hours.

76. The pharmaceutical kit according to claim 3, wherein the steady release from the controlled release composition is maintained for at least about 3 hours.

77. The pharmaceutical kit according to claim 4, wherein the release pattern of midodrine and/or desglymidodrine from the composition when tested using an in vitro dissolution test is as follows (±25% w/w of the values stated below):
   about 25% w/w is released about 30 min after start of the test,
   about 35% w/w is released about 1 hour after start of the test,
   about 39% w/w is released about 2 hours after start of the test,
   about 47% w/w is released about 3 hours after start of the test,
   about 53–56% such as, e.g., about 53% w/w is released about 4 hours after start of the test,
   about 66–72% such as, e.g., about 66% w/w is released about 6 hours after start of the test,
   about 80–85% w/w is released about 8 hours after start of the test,
   about 93% w/w is released about 10 hours after start of the test, and
   about 100% w/w is released about 12 hours after start of the test.

78. The pharmaceutical kit according to claim 5, wherein the release pattern of midodrine and/or desglymidodrine from the composition when tested using an in vitro dissolution test is as follows (±20% w/w of the values stated below):
   about 28% w/w is released about 30 minutes after start of the test,
   about 35% w/w is released about 1 hour after start of the test,
   about 41% w/w is released about 2 hours after start of the test,
   about 45% w/w is released about 3 hours after start of the test,
   about 55% w/w is released about 4 hours after start of the test,
   about 70w/w is released about 6 hours after start of the test,
   about 78% w/w is released about 7 hours after start of the test,
   about 90% w/w is released about 8 hours after start of the test,
   about 95% w/w is released about 10 hours after start of the test, and
   about 100% w/w is released about 12 hours after start of the test.

79. The kit according to claim 6, wherein a therapeutically effective plasma concentration of desglymidodrine is maintained for at least about 10 hours.

80. The kit according to claim 5, wherein the steady release period ii) from the controlled release composition is maintained for at least 3 hours.

81. The pharmaceutical kit according to claim 9, wherein a therapeutically effective plasma concentration of desglymidodrine is maintained for at least about 10 hours.

82. The kit according to claim 11, wherein the plasma concentration of desglymidodrine from the controlled release composition is maintained at a therapeutically active level for about 6–14 hours.

83. The kit according to claim 11, wherein the plasma concentration of desglymidodrine from the controlled release composition is maintained at a relatively constant level for about 6–14 hours.

84. A kit according to claim 12, wherein the relatively constant level n is ±50% and wherein n is the plasma concentration in ng/ml and monitored in healthy persons.

85. A kit according to claim 15, wherein the plasma concentration of midodrine from the controlled release composition after oral administration is maintained at a relatively constant level for at least about 0.7 hours.

86. A kit according to claim 16, wherein the relatively constant level m is ±50% such as, e.g. m±40%, and wherein m is the plasma concentration in ng/ml and monitored in healthy persons.

87. A kit according to claim 21, wherein the release pattern of midodrine from the controlled release composition when tested using an in vitro dissolution test is as follows (±20% w/w of the values stated below):
   about 25% w/w is released about 30 min after start of the test,
   about 35% w/w is released about 1 hour after start of the test,
   about 39% w/w is released about 2 hours after start of the test,
   about 47% w/w is released about 3 hours after start of the test,
   about 53% w/w is released about 4 hours after start of the test,
   about 66 w/w is released about 6 hours after start of the test,
   about 75% w/w is released about 7 hours after start of the test,
   about 80% w/w is released about 8 hours after start of the test,
   about 90% w/w is released about 10 hours after start of the test, and
   about 100% w/w is released about 12 hours after start of the test.

88. A kit according to claim 22, wherein the release pattern of midodrine from the controlled release composition when tested using an in vitro dissolution test is as follows (±20% w/w of the values stated below):
   about 20% w/w is released about 30 min after start of the test,
   about 20% w/w is released about 1 hour after start of the test,
   about 20% w/w is released about 2 hours after start of the test, about 20% w/w is released about 3 hours after start of the test, about 25% w/w is released about 4 hours after start of the test, about 45 w/w is released about 6 hours after start of the test, about 75% w/w is released about 7 hours after start of the test, about 90% w/w is released about 8 hours after start of the test, about 95% w/w is released about 10 hours after start of the test, about 100% w/w is released about 12 hours after start of the test.

89. A kit according to claim 23, wherein the second rise in release rate from the controlled release composition takes place about 6–8 hours after start of the dissolution test.

90. A kit according to claim 25, wherein the release rate of midodrine from the controlled release composition when tested using an in vitro dissolution is as follows (±10–30% of the values stated below):

about 15–40%/hour about 30 minutes after start of the test, about 4–15%/hour about 1 hour after start of the test, about 2–10%/hour about 2 hours after start of the test, about 2–10%/hour about 3 hours after start of the test, about 2–15%/hour about 4 hours after start of the test, about 2–30%/hour about 6 hours after start of the test, about 2–15%/hour about 8 hours after start of the test, about 0–10%/hour about 10 hours after start of the test, about 0–10%/hour about 12 hours after start of the test.

91. A kit according to claim 26, wherein the $W_{50}$ of midodrine, defined as corresponding to the time the plasma concentration curve is or is above 50% of the $C_{max}$ value, from the controlled release composition is from about 1.3 to about 8 hours such.

92. A kit according to claim 27, wherein the $W_{50}$ of desglymidodrine, defined as corresponding to the time the plasma concentration curve is or is above 50% of the $C_{max}$ value, from the controlled release composition is from about 6 to about 11 hours.

93. A kit according to claim 29, wherein MRT (mean residence time) for the controlled release composition is increased by a factor of at least 2 when compared with a plain Gutron® tablet administered at the same dose and where MRT is determined from a plasma concentration versus time curve and the plasma concentration reflects the sum concentration in nmol/l of midodrine and desglymidodrine.

94. A kit according to claim 30, wherein $W_{50}$ is increased by a factor of at least 2.5 when compared with a plain Gutron® tablet administered in the same dose and where $W_{50}$ is determined from a plasma concentration versus time curve and the plasma concentration reflects the sum concentration in nmol/l of midodrine and desglymidodrine after administration of the controlled release composition.

95. A kit according to claim 31, wherein $W_{75}$ (C>75% $C_{max}$) is increased by a factor of at least 2 when compared with a plain Gutron® tablet administered in the same dose and where $W_{75}$ (C>75% $C_{max}$) is determined from a plasma concentration versus time curve and the plasma concentration reflects the sum concentration in nmol/l of midodrine and desglymidodrine after administration of the controlled release composition.

96. A kit according to claim 32, wherein the MRT for midodrine from the controlled release composition is at least about 2 hours.

97. A kit according to claim 33, wherein the MRT for desglymidodrine from the controlled release composition is at least about 7 hours.

98. A kit according to claim 36, wherein at least 95% w/w of midodrine is present in the therapeutically active enantiomeric form.

99. A kit according to claim 40, wherein at least 95% w/w of desglymidodrine is present in the therapeutically active enantiomeric form.

100. A kit according to claim 46, wherein the controlled release composition comprises at least a first and a second part, each part containing midodrine and/or, if present, desglymidodrine, the first part being adapted to release midodrine and/or, if present, desglymidodrine, in a controlled manner during the first 0–11 hours after oral intake and the second part being adapted to release midodrine and/or, if present, desglymidodrine, starting at least 6 hours after oral intake.

101. A kit according to claim 62, wherein the first part has a release kinetic corresponding to a 1½, second, third or fourth order release.

102. A kit according to claim 63, wherein the second part has a release kinetic corresponding to a 1½, second, third or fourth order release.

103. A kit according to claim 64, wherein the relatively fast onset composition or part of the kit results in a peak or shoulder plasma concentration within 60 minutes of administration of the relatively fast onset composition.

104. A pharmaceutical kit according to claim 73, wherein the midodrine and/or desglymidodrine in relatively fast onset composition is present in an amount of from 0.5 mg to 7.5 mg.

* * * * *